United States Patent [19]
Ahmad et al.

[11] Patent Number: 6,048,877
[45] Date of Patent: Apr. 11, 2000

[54] TETRALONE DERIVATIVES AS ANTIARRHYTHMIC AGENTS

[75] Inventors: Saleem Ahmad, Wall; Philip D. Stein, Pennington; Francis N. Ferrara, Martinsville, all of N.J.; Karnail S. Atwal, Newtown, Pa.

[73] Assignee: Bristol-Myers Squibb Company, Princeton, N.J.

[21] Appl. No.: 09/009,812

[22] Filed: Jan. 20, 1998

Related U.S. Application Data

[60] Provisional application No. 60/038,917, Feb. 21, 1997.

[51] Int. Cl.$^7$ ........................ A61K 31/445; C07D 211/32
[52] U.S. Cl. ........................ 514/319; 514/229.5; 514/247; 514/255; 514/278; 514/325; 514/326; 514/357; 514/408; 514/409; 514/411; 514/423; 514/595; 514/617; 514/623; 514/682; 514/684; 544/359; 544/361; 544/368; 544/380; 546/15; 546/16; 546/79; 546/203; 546/205; 546/285; 548/407; 548/427; 548/528; 548/530; 548/579; 564/47; 564/173; 564/180; 568/326; 568/328; 568/330
[58] Field of Search ...................... 544/359, 361, 544/368, 380; 546/15, 16, 79, 203, 205, 285; 548/407, 427, 528, 530, 579; 564/47, 173, 180; 568/326, 328, 330; 514/229.5, 247, 255, 278, 319, 325, 326, 357, 408, 409, 411, 423, 595, 617, 623, 682, 684

[56] References Cited

U.S. PATENT DOCUMENTS

| | | | |
|---|---|---|---|
| 4,785,006 | 11/1988 | Worthington et al. | 514/319 |
| 5,439,914 | 8/1995 | Claremon et al. | 514/278 |
| 5,847,159 | 12/1998 | Kai et al. | 514/408 |

FOREIGN PATENT DOCUMENTS

| | | |
|---|---|---|
| 259782 | 3/1987 | European Pat. Off. |
| 92/11240 | 7/1992 | WIPO . |
| WO93/04061 | 3/1993 | WIPO . |
| WO95/14471 | 6/1995 | WIPO . |
| WO96/05839 | 2/1996 | WIPO . |

OTHER PUBLICATIONS

Bhattacharya et al. CA 100:156040, 1984.
Zelle et al. CA 126:74618, 1996.
Kai et al. CA 126:47121, 1996.
Shrivastavas et al. CA 125:10328, 1996.
Mitrenga et al. CA 123:25145, 1995.
Gueremy et al. CA 115:232233, 1991.
Defraine et al: CA 107:96452, 1986.
IBM CA 106:175963, 1986.
Worthington et al. CA 106:115236, 1986.
Kanao et al. CA 103:178258, 1985.
Cross et al. CA 99:105247, 1983.
Kulkarni et al. CA 97:109663, 1982.
Welch et al. CA 88:115083, 1978.
Welch et al. CA 87:67028, 1977.
Brown et al. CA 75:88829, 1971.
Schoenenberger et al. CA 72:65748, 1969.
Setnikar et al. "Cardiovascular and other pharmacologic . . . ." CA 66:54082, 1966.
Hernestam et al. "Treating cardiac arrhythmia . . . " CA 87:90726, 1976.
Parke et al. "Cis–2,6–dimethyl–. . ." CA 87:84839, 1976.
Petersen et al. "Experimental anti–arrhythmic . . . " CA 89:209056, 1978.
Chan "2–substituted tetralin derivatives . . . " CA 107:228448, 1987.
Chan et al. "A partially rigid butyrophenone . . . " CA 108:94178, 1986.
Loza et al. "Antiserotoninergic activity of 2–aminoethyl–benzocyclanones . . . " CA 119:85437, 1993.
Kato et al. "Preparation of 2–aminoalkyltetralines . . . " CA 129:216428, 1998.

(List continued on next page.)

*Primary Examiner*—Ceila Chang
*Attorney, Agent, or Firm*—Burton Rodney

[57] ABSTRACT

Tetralone derivatives of the formula

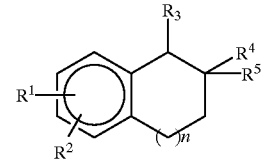

I where
  $R^1$ is halo, alkyl, alkenyl, alkynyl, cycloalkyl, aryl, (aryl)alkenyl, (aryl)alkynyl, alkoxy, O-alkenyl, O-aryl, O-alkyl(heterocyclo), COO-alkyl,alkanoyl, CO-amino, CO-substituted amino, alkyl-CO-amino, alkyl-CO-substituted amino, NHCO-alkyl, NHCO-aryl, NHCO-alkyl(heterocyclo), N(alkyl)CO-alkyl, N(alkyl)CO-aryl, N(alkyl)CO-heterocyclo, N(alkyl)CO-alkyl(heterocyclo);
  $R^2$ is hydrogen, alkyl, halo, aryl, alkoxy, amino, substituted amino;
  $R^3$ is oxo, hydroxy, alkoxy, O—COalkyl, —O—COaryl, —O—COheterocyclo, NOH, NO-alkyl, N-amino, N-substituted amino, N-NHCONHalkyl, N-NHSO$_2$alkyl, N-NHSO$_2$aryl, amino, substituted amino, NHCO-alkyl, NHCO-aryl, NHCO-heterocyclo, spiroheterocyclo;
  $R^4$ is hydrogen, alkyl, alkyl(COalkyl), alkyl(COOalkyl); or
  $R^3$ and $R^4$ taken together with the atoms to which they are attached form a five- to seven-membered ring which can contain up to three heteroatoms selected from oxygen, nitrogen and sulfur;
  $R^5$ is hydrogen, alkyl, alkenyl, alkyl(heterocyclo), alkyl-NHCO(alkyl), alkyl-NHCO(aryl), alkyl-NHCO(heterocyclo), alkyl-NHCO(alkylheterocyclo); and
  n is an integer of 0 to 2. These compounds have been found to be useful in the treatment of arrhythmia.

18 Claims, No Drawings

OTHER PUBLICATIONS

Selnick, H.G. et al, "Class III Antiarrhythmic Activity in vivo by Selective Blockade of the Slowly Activating Cardiac Delayed Rectifier Potassium Current $I_{Ks}$ by (R)–2–(2,4–Trifluoromethyl)–N–[2–oxo–5–phenyl–1– (2,2,2– trifluoroethyl)–2,3–dihydro–1H–benzo[e][1,4]diazepin–3–yl]acetamide", J. Med. Chem., 40(24), 3865–3868, 1997.

Nair, L.A. et al, "Emerging Class III Antiarrhythmic Agents: Mechanism of Action and Proarrhythmic Potential", Cardiovascular Drugs and Therapy 1997; 11:149–167.

TETRALONE DERIVATIVES AS ANTIARRHYTHMIC AGENTS

This application claimed benefit of U.S. Provisional Application 60/038,917 filed Feb. 21, 1997.

BRIEF DESCRIPTION OF THE INVENTION

This invention is concerned with compounds of the formula $$I$$

where
- $R^1$ is halo, alkyl, alkenyl, alkynyl, O-alkyl(aryl), CONH-alkyl, CONH-alkyl(aryl), CONHalkyl(cycloalkyl) cycloalkyl, aryl, (aryl)alkenyl, (aryl)alkynyl, alkoxy, O-alkenyl, O-aryl, O-alkyl(heterocyclo), COO-alkyl, alkanoyl, CO-amino, CO-substituted amino, alkyl-CO-amino, alkyl-CO-substituted amino, NHCO-alkyl, NHCO-aryl, NHCO-alkyl(heterocyclo), N(alkyl)CO-alkyl, N(alkyl)CO-aryl, N(alkyl)CO-heterocyclo, N(alkyl)CO-alkyl(heterocyclo);
- $R^2$ is hydrogen, alkyl, halo, aryl, alkoxy, amino, substituted amino;
- $R^3$ is oxo, hydroxy, alkoxy, O—COalkyl, —O—COaryl, —O—COheterocyclo, NOH, NO-alkyl, N-amino, N-substituted amino, N-NHCONHalkyl, N-NHSO$_2$alkyl, N-NHSO$_2$aryl, amino, substituted amino, NHCO-alkyl, NHCO-aryl, NHCO-heterocyclo, spiroheterocyclo;
- $R^4$ is hydrogen, alkyl, alkyl(COalkyl), alkyl(COOalkyl); or
- $R^3$ and $R^4$ taken together with the atoms to which they are attached form a five- to seven-membered ring which can contain up to three hetero atoms selected from oxygen, nitrogen and sulfur;
- $R^5$ is hydrogen, alkyl, alkenyl, alkyl(heterocyclo, alkyl-NHCO(alkyl), alkyl-NHCO(aryl), alkyl-NHCO(heterocyclo), alkyl-NHCO(alkylheterocyclo or alkyl(substituted amino)); and
- n is an integer of 0 to 2.

These compounds are useful in the treatment of arrhythmia. The invention is also concerned with pharmaceutical compositions comprising one or more of the novel compounds as an active antiarrhythmic agent either alone or in combination with other cardiovascular agents such as a B-blocker or other antiarrhythmic agent; and a method of treating arrhythmia by administration of one of the novel compounds or compositions thereof to a patient in need of such treatment.

DETAILED DESCRIPTION OF THE INVENTION

Definition of Terms

Listed below are definitions of various terms used to describe the compounds of the instant invention. These definitions apply to the terms as they are used throughout the specification (unless they are otherwise limited in specific instances) either individually or as part of a larger group.

The term "alkyl" refers to both straight and branched chain groups having 1 to 8 carbon atoms, preferably 1 to 5 carbons, such as methyl, ethyl, propyl, butyl, pentyl, hexyl, heptyl, octyl, the various branched chain isomers thereof, such as isopropyl, t-butyl, isobutyl, isohexyl, 4,4-dimethylpentyl, 2,2,4-trimethylpentyl and the like; as well as such groups substituted by, one or more substituents such as halo, alkoxy, amino, substituted amino, aryl, cycloalkyl, hydroxy, alkanoylamino, arylcarbonylamino, nitro, cyano, thiol, alkylthio and the like.

The term "alkoxy" refers to alkyl-O-.

The term "alkylthio" refers alkyl-S-.

The term "alkenyl" refers to any of the above alkyl groups further containing at least one carbon to carbon double bond.

The term "alkynyl" refers to any of the above alkyl groups further containing at least one carbon to carbon triple bond.

The term "alkanoyl" refers to alkyl-C(O)—.

The term "cycloalkyl" refers to saturated cyclic hydrocarbon groups containing 3 to 8 ring carbons optionally substituted with one or more substituents such as alkyl or hydroxy.

The term "halogen" or "halo" refers to chlorine, bromine, iodine and fluorine.

The term "aryl" refers to monocyclic or bicyclic aromatic hydrocarbon groups having 6 to 12 carbon atoms in the ring portion, such as phenyl, 1-naphthyl, 2-naphthyl, phenanthrene or dihydrophenanthrene; or such groups substituted with one or more substituents such as alkyl, alkylthio, alkoxy, halo, nitro, cyano, hydroxy, amino, substituted amino, phenyl, —C(O)-phenyl, substituted phenyl, —C(O)—substituted amino, heterocycle, carboxylic acid or carboxylic ester.

The term "aryl" also includes those groups listed above fused to a five- or six-membered ring which optionally contains an oxygen, sulfur or nitrogen atom. The five- or six-membered ring may further optionally be substituted with for example, alkyl or -phenyl-CF$_3$.

The term "heterocyclo" or "hetero" refers to fully saturated or unsaturated rings of five or six atoms containing one or two oxygen and/or sulfur atoms and/or one to four nitrogen atoms provided that the total number of hetero atoms in the ring is four or less. Exemplary monocyclic heterocyclo groups include 2- and 3-thienyl, 2- and 3-furyl, 2-, 3- and 4-pyridyl and imidazolyl.

The term heterocyclo or hetero also includes bicyclic rings wherein the five- or six-membered ring containing oxygen and/or sulfur and/or nitrogen atoms as defined above is fused to a benzene ring and the bicyclic ring is attached by way of an available atom.

Exemplary bicyclic hetero groups include 4-, 5-, 6- or 7-indolyl, 4-, 5-, 6- or 7-isoindolyl, 5-, 6-, 7- or 8-quinolinyl, 5-, 6-, 7- or 8-isoquinolinyl, 4-, 5-, 6- or 7-benzothiazolyl, 4-, 5-, 6- or 7-benzoxazolyl, 4-, 5-, 6- or 7-benzimidazolyl, 4-, 5-, 6- or 7-benzoxadiazolyl and 4-, 5-, 6- or 7-benzofuranzanyl.

The term heterocyclo or hetero also includes such monocyclic and bicyclic rings wherein an available atom is substituted by one or more substituents such as alkyl, aryl, alkylthio, alkoxy, halo, nitro, keto, cyano, hydroxy, azo, oxo, thiazo, amino, substituted amino, carboxylic acid, carboxylic ester, or alkoxy further substituted with a carboxylic acid or a five- to eight-membered ring optionally containing 1 to 4 heteroatoms selected from oxygen, nitrogen and sulfur, optionally substituted by groups such as alkyl or halogen.

The term "substituted amino" refers to a group of the formula —NZ$^2$Z$^3$ wherein Z$^2$ is hydrogen, alkyl, cycloalkyl, aryl, morpholinylalkyl, heterocyclo or (heterocyclo)alkyl and $Z^3$ is hydrogen, alkyl, cycloalkyl or aryl further substituted with a carboxylic acid or carboxylic ester, provided that when $Z^2$ is hydrogen, then $Z^3$ is other than hydrogen; or $Z^2$ and $Z^3$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, aryl or hydroxy.

Throughout the specification, groups and substituents thereof are chosen to provide stable moieties and compounds.

The compounds of formula I form salts which are also within the scope of this invention. Pharmaceutically acceptable (i.e., non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts may be obtained, for example, by exchanging the carboxylic acid protons, if they contain a carboxylic acid, in compound I with the desired ion in a medium in which the salt precipitates or in an aqueous medium followed by evaporation. Other salts can be formed as known to those having ordinary skill in the art.

The compounds of formula I may form salts with a variety of organic and inorganic acids. Such salts include those formed with hydrogen chloride, hydrogen bromide, methanesulfonic acid, sulfuric acid, acetic acid, trifluoroacetic acid, maleic acid, benzenesulfonic acid, toluenesulfonic acid and various others (e.g., nitrates, phosphates, borates, tartrates, citrates, succinates, benzoates, ascorbates, salicylates and the like). Such salts may be formed by reacting compound I in an equivalent amount of the acid in a medium in which the salt precipitates or in an aqueous medium followed by evaporation.

In addition, zwitterions ("inner salts") may be formed.

A compound of the formula I may also have prodrug forms. Any compound that will be converted in vivo to provide the bioactive agent (i.e., the compound of formula I) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985);

b) *Methods in Enzymology*, Vol. 42, 309–396, edited by K. Widder et al. (Academic Press, 1985);

c) *A Textbook of Drug Design and Development*, edited by Krogsgaard-Larsen and H. Bundgaard, Chapter 5, "Design and Application of Prodrugs," by H. Bundgaard, 113–191 (1991);

d) *Advanced Drug Delivery Reviews*, H. Bundgaard, 8, 1–38 (1992);

e) *Journal of Pharmaceutical Sciences*, H. Bundgaard et al., 77, 285 (1988); and f) *Chem Pharm Bull*, N. Kakeya et al., 32, 692 (1984).

It should further be understood that solvates (e.g., hydrates) of the compounds of formula I are also within the scope of the present invention. Methods of solvation are generally known in the art.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in diastereomeric forms or in mixtures thereof. The below described processes can utilize racemates, enantiomers or diastereomers as starting materials. When diastereomeric products are prepared, they can be separated by conventional methods for example, chromatographic or fractional crystallization.

Use and Utility

The compounds of formula I are useful in the treatment of arrhythmia. More specifically, the compounds of the present invention have the pharmacological properties required for the antiarrhythmic agents of Class III.

Class III agents increase myocardial refractoriness via a prolongation of cardiac action potential duration. Theoretically, prolongation of the cardiac action potential can be achieved by enhancing inward currents (i.e. $Na^+$ or $Ca^{2+}$ currents; hereinafter $I_{Na}$ and $I_{Ca}$ respectively) or by reducing outward repolarizing potassium ($K^+$) currents. The delayed rectifier ($I_K$)$K^+$ current is the main outward current involved in the overall repolarization process during the action potential plateau, whereas the transient outward ($I_{to}$) and inward rectifier ($I_{K1}$)$K^+$ current are responsible for the rapid initial and terminal phases of repolarization, respectively. Cellular electrophysiologic studies have demonstrated that $I_K$ consists of two pharmacologically and kinetically distinct $K^+$ current subtypes, $I_{Kr}$ (rapidly activating and deactivating) and $I_{Ks}$ (slowly activating and deactivating).

Most Class III agents that are known to be in development predominantly block $I_{Kr}$. These agents have a potential liability in that they have an enhanced risk of proarrhythmia at slow heart rates. The compounds of the present invention prolong the mycocardial action potential in vitro without a significant depression of the Vmax and with the prolongation of Qtc-interval in anesthetized dogs. In addition the compounds of the present invention selectively block $I_{Ks}$. The preferred compounds of the present invention are those which have selectivity of $I_{Ks}:I_{Kr}$ greater than or equal to 5.

The compounds of the present invention are effective in treating and preventing all types of arrhythmias including ventricular and atrial (supraventricular) arrhythmias. The compounds of the present invention are especially useful to control reentrant arrhythmias and prevent sudden death due to the ventricular fibrillation.

In the novel method of this invention of treating arrhythmia, a novel compound or pharmaceutically acceptable salt thereof, is administered in an amount ranging from about 0.0001 to about 20 mg per kg of body weight per day, preferably from about 0.001 to about 10 mg per kg of body weight per day in a single dose or in 2 to 4 divided doses.

The novel compounds of this invention can be administered as the sole active ingredient or in combination with other antiarrhythmic agents or other cardiovascular agents.

The compounds, or pharmaceutically acceptable salts thereof, of the present invention, in the described dosages, are administered orally, intraperitoneally, subcutaneously, intramuscularly, transdermally, sublingually or intravenously. They are preferably administered orally, for example in the form of tablets, troches, capsules, elixirs, suspensions, syrups, wafers, chewing gum, or the like prepared by art recognized procedures. The amount of active compound in such therapeutically useful compositions or preparations is such that a suitable dosage will be obtained.

Preferrd Moieties

The preferred compounds of the present invention are those compounds of formula I where:

$R^1$ is O-alkyl(aryl), CONH-alkyl, CONH-alkyl(aryl), CONH-alkyl(cycloalkyl);
$R^2$ is hydrogen;
$R^3$ is oxo, hydroxy, alkoxy or NOH;
$R^4$ is hydrogen or alkyl;
$R^5$ is alkyl, alkyl(substituted amino); and
n is an integer of 0 to 2.

Process of Preparation

The compounds of the instant invention be obtained by methods exemplified by the following descriptions.

Compounds of formula Ia (which are compounds of formula I where $R^3$ is oxo and $R^5$ is is alkyl(substituted amino)) and Ib (which are compounds of formula I where $R^3$ is hydroxy and $R^5$ is alkyl(substituted amino)) can be prepared according to Scheme 1.

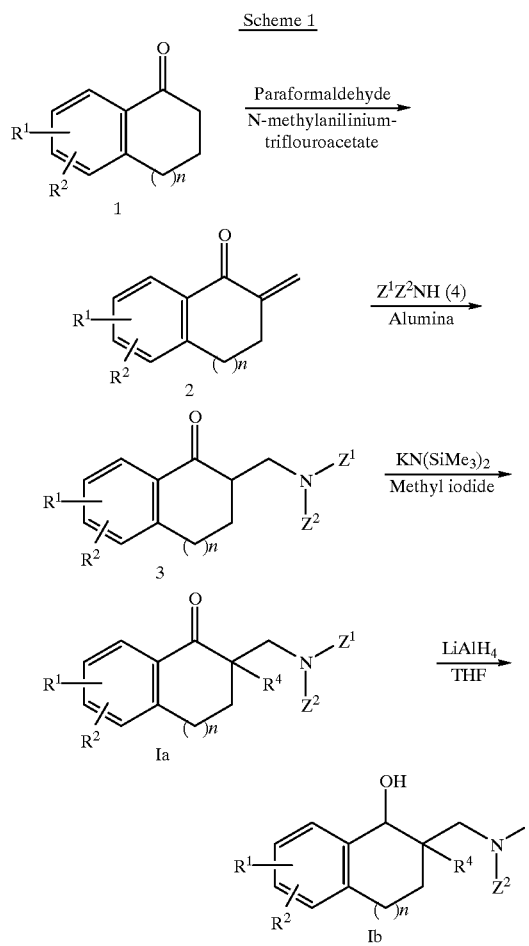

The ketone of formula 1 is reacted with paraformaldehyde in the presence of N-methylanilinium trifluoroacetate to yield compounds of formula 2 which undergoes the Michael addition with an amine of formula 4 to provide compounds of formula 3. Compounds of formula can be alkylated ($R^4X$, base) to provide compounds of formula Ia which can be further reduced to compounds of formula Ib.

Compounds of formula 1 and 4 are commercially available or they can be prepared by modification of the methods known in the literature.

Compounds of formula Ic (which are compounds of formula I where $R^3$ is hydroxy and $R^4$ is hydrogen and $R^5$ is alkyl(substituted amino)) can be prepared according to Scheme 2.

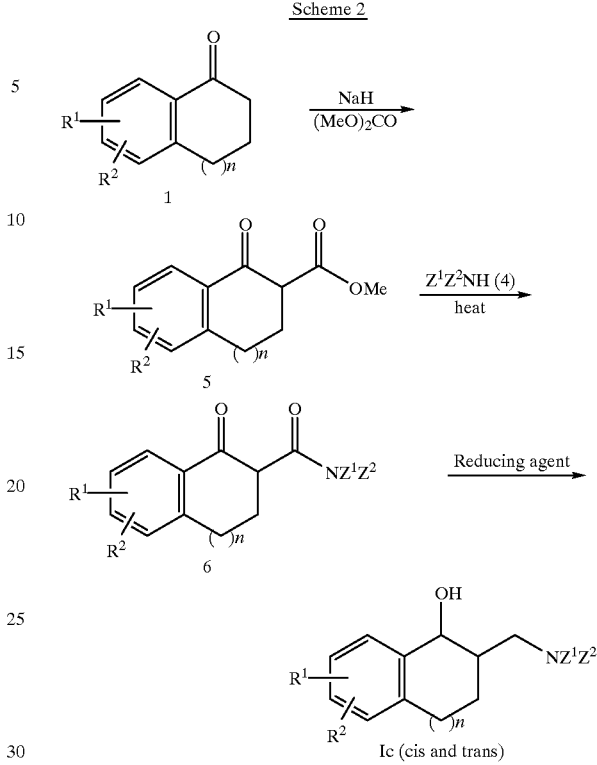

The ketone of formula 1 is acylated with dimethylcarbonate and sodium hydride to give compounds of formula 5 which is condensed with an amine of formula 4 to provide compounds of formula 6. Reduction of 6 with a reducing agent (e.g., lithiumaluminum hydride) provides compounds of formula Ic.

Compounds of formula Id-g can be prepared according to Scheme 3.

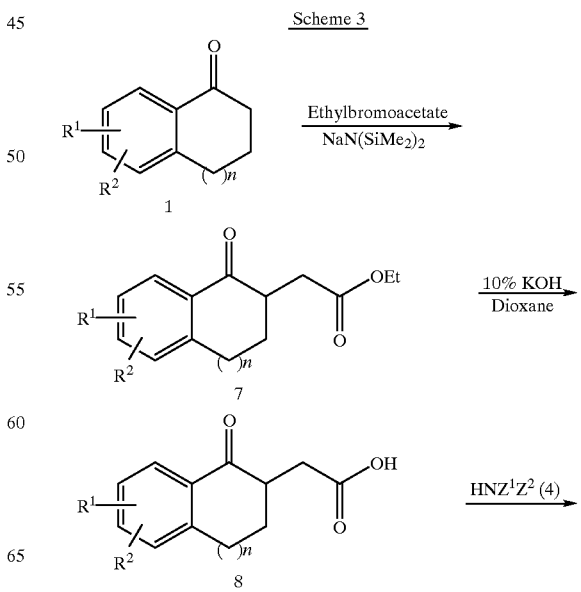

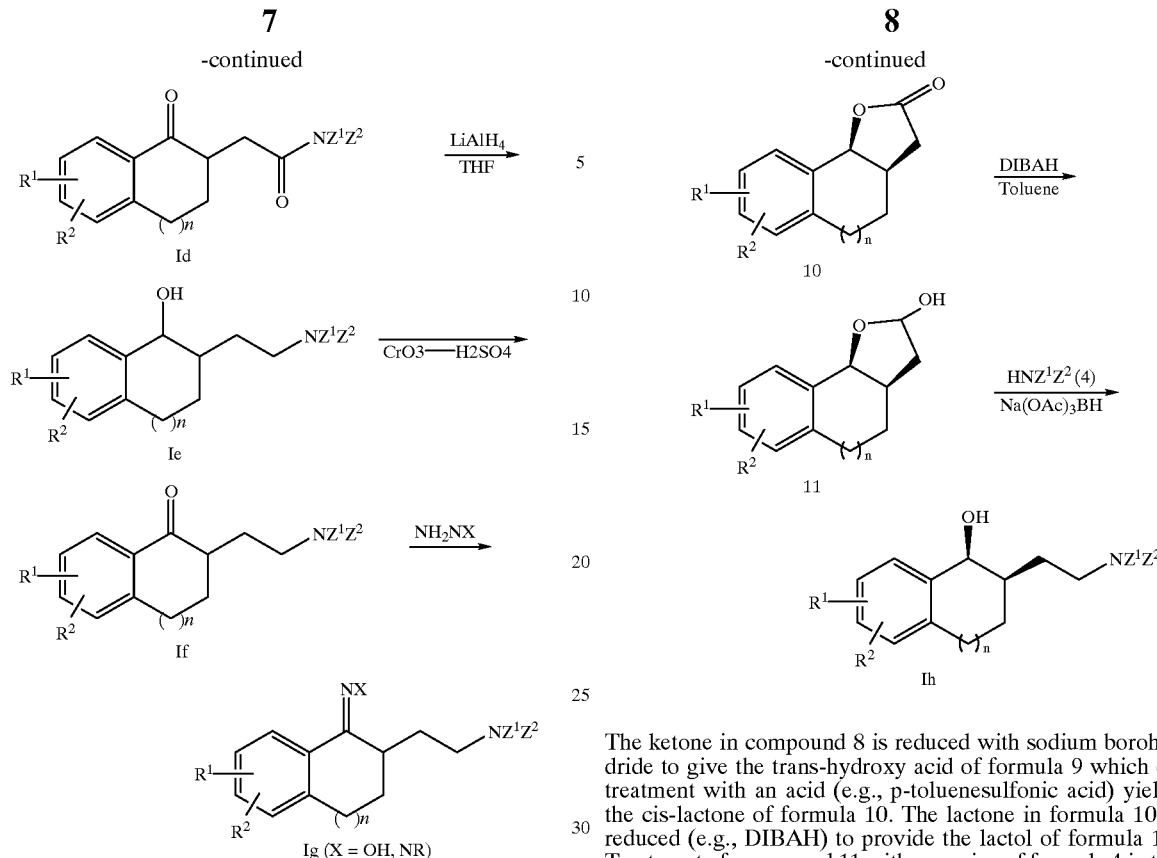

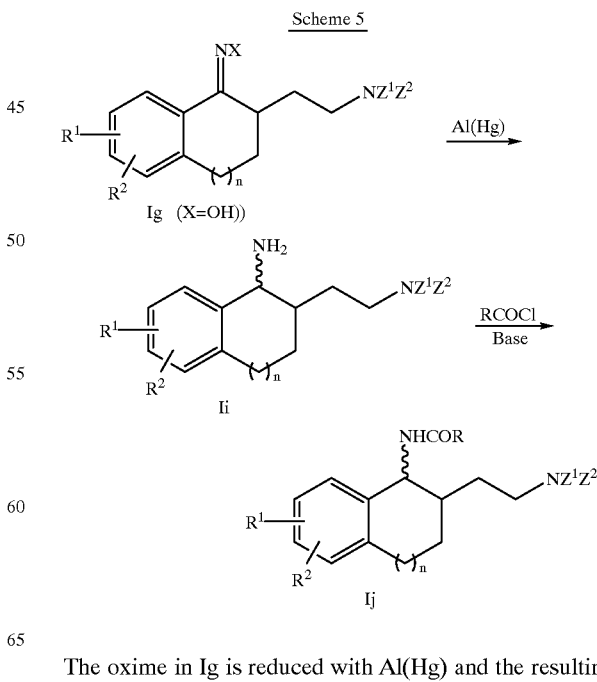

The ketone in compound 8 is reduced with sodium borohydride to give the trans-hydroxy acid of formula 9 which on treatment with an acid (e.g., p-toluenesulfonic acid) yields the cis-lactone of formula 10. The lactone in formula 10 is reduced (e.g., DIBAH) to provide the lactol of formula 11. Treatment of compound 11 with an amine of formula 4 in the presence of a reducing agent (e.g., sodium triacetoxyborohydride, sodium cyanoborohydride) provides the desired compounds of formula Ih.

Compounds of formula 8 are described in Scheme 3 and compounds of formula 4 are commercially available or they can be prepared by modification of the methods known in the literature.

Compounds of formula Ii and Ij can be prepared according to Scheme 5.

The ketone of formula 1 is alkylated with methyl bromoacetate and a base to provide compounds of formula 7. The ester in 7 is saponified to give the acid of formula 8 which on coupling with an amine 4 ($Z^1Z^2NH$) provides amides of formula Id. Compounds of formula Id are reduced with lithiumaluminum hydride to yield amino alcohols of formula Ie. The oxidation of the alcohol with the Jones reagent provides compounds of formula If which can be further converted to compounds of formula Ig on treatment with hydroxyl amine and hydrazine or derivatives thereof.

Compounds of formula Ih (cis-alcohol) can be prepared from compounds of formula 1 as described in Scheme 4.

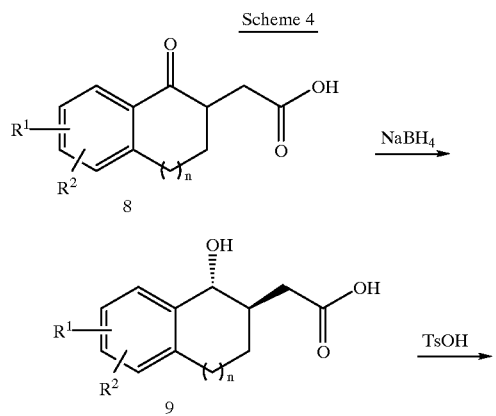

The oxime in Ig is reduced with Al(Hg) and the resulting amine Ii is derivatized with an appropriate reagent (ROCl)

to provide the requisite compounds of formula Ij. Compounds of formula Ig are described in Scheme 3 and compounds of formula RCOCl are commercially available or they can be readily prepared by methods known in the literature.

The spiro heterocyclic ring containing compounds of formula Ik can be prepared from the corresponding ketones of formula If by treatment with potassium cyanide and ammonium carbonate as shown in Scheme 6.

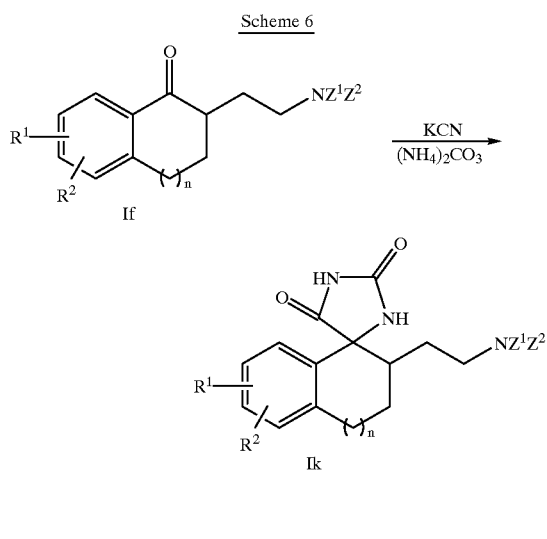

Compounds of formula In can be prepared as described below in Scheme 7.

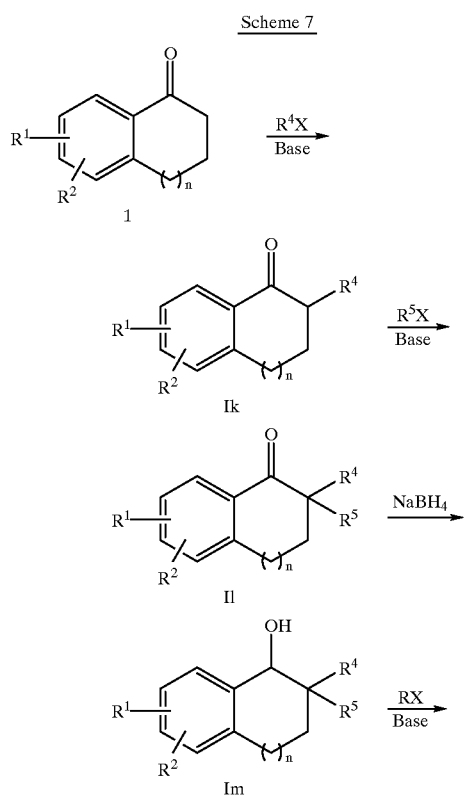

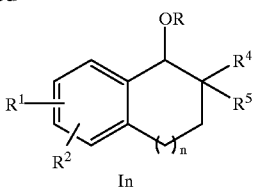

Compounds of formula Il can be prepared from compounds of formula 1 by successive alkylation with approproate alkylating agents in the presence of a base such as sodium hydride. The compounds of formula Im can be reduced with a reducing agent (e.g., sodium borohydride) to the alcohol of formula Im which can be further alkylated to provide the desired compounds of formula In.

Compounds of formula 1 are commercially available or they can be prepared by methods known in the literature. The alkylating agents of formula $R^4X$, $R^5X$ and RX are commercially available or can be readily obtained by methods known in the literature.

Compounds of formula Io wherein $R^1$ is acid or a derivative thereof can be prepared from compounds of formula 1 wherein $R^1$ is hydroxy according to Scheme 8.

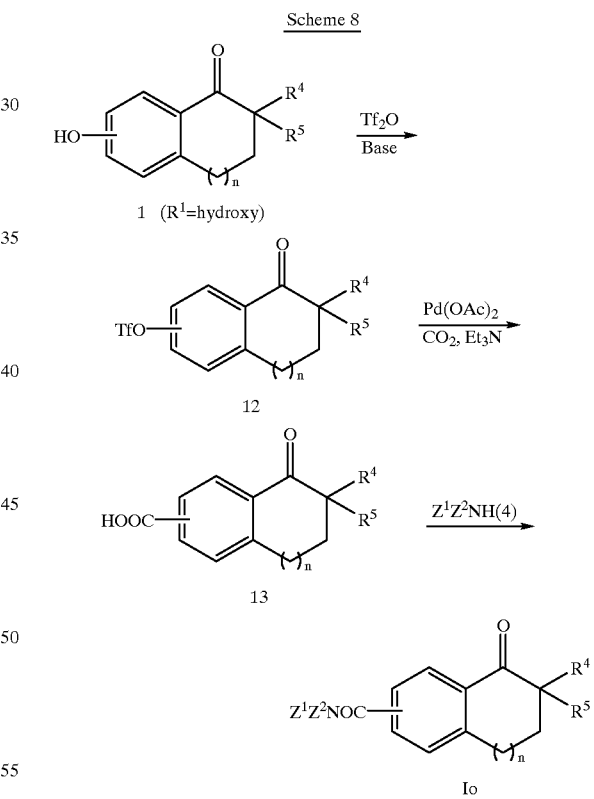

The hydroxy group in 1 is converted to a triflate 12 by treatment with triflic anhydride and a base (e.g., pyridine). The triflate in 12 can be converted to a carboxylic acid of formula 13 in the presence of a palladium catalyst. The carboxylic acid 13 can be converted to its derivatives (e.g., amide Io) by standard methods described in the literature.

EXAMPLES

The following examples and preparations describe the manner and process of making and using the invention and

Example 1

3,4-Dihydro-6-methoxy-2-[(4-phenyl-1-piperidinyl) methyl]-1(2H)-naphthalenone, hydrochloride

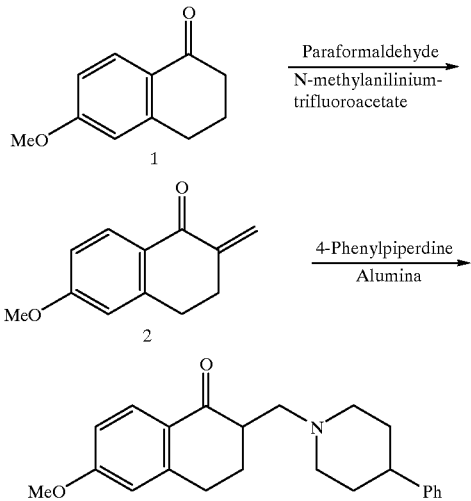

A. Compound 2:

A mixture of 6-methoxytetralone (29.24 g, 165.9 mmol), paraformaldehyde (22.4 g, 746.6 mmol) and N-methylanilinium trifluoroactate (55 g, 248.9 mmol) in 250 mL THF was refluxed for 4 hours and allowed to come to room temperature. To this was added ether (250 mL) with stirring and the mixture was decanted to remove the gummy precipitate. The supernent was washed with sat. $NaHCO_3$, the oganic layer was dried ($MgSO_4$) concentrated. The residue was redissolved in ether, filtered through celite and concentrated to afford compound 2 as a thick yellow oil.

B. 3,4-Dihydro-6-methoxy-2-[(4-phenyl-1-piperidinyl)-methyl]-1(2H)-naphthalenone, hydrochloride To a mixture of the title A compound (2.2 g, 12.11 mmol), 4-phenylpiperidine(1.95 g, 12.11 mmol) and alumina (4.56 g) in 300 mL toluene was added water (0.219 mL) and the mixture was stirred at room temperature for 3.5 hours. The reaction mixture was then filtered, the residue washed with ethyl acetate and the combined filtrate was concentrated. The residue was dissolved in dichloromethane, acidified with 4 N HCl in dioxane, concentrated and the residue triturated sequentially with ethyl acetate and acetonitrile to afford the title compound (4.2 g, 90%) as a white solid.

mp (°C.) 176–177. Anal. for: $C_{23}H_{27}NO_2 \cdot HCl$: Calc'd: C, 71.58; H, 7.31; N, 3.63. Found: C, 72.08; H, 7.21; N, 3.64.

Example 2

3,4-Dihydro-6methoxy-2-[(4-phenyl-1-piperidinyl) methyl]-1(2H)-naphthalenone, hydrochloride

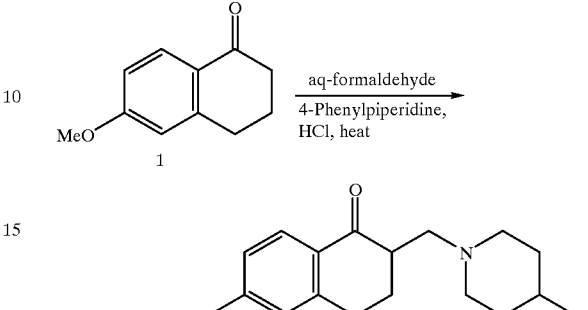

Concentrated hydrochloric acid (4.9 mL) was added to a solution of 4-phenylpiperidine (9.38 g, 58.2 mmol) in isopropanol (60 mL) at 10–15° C. followed by the sequential addition of 6-methoxy-1-tetralone (9.76 g, 55.4 mmol), 37% aqueous formaldehyde (5.72 g) and 60 mL isopropanol. The mixture was refluxed for 1 hour, diluted with toluene, concentrated and the residue recrystallized sequentially from acetone and ethanol to afford the title compound as a white solid (5 g), mp 177–8° C.

Using methodology analogous to that described for the title compounds of Examples 1 and 2, the compounds of Examples 3 to 12 were prepared:

Example 3

3,4-Dihydro-6-methoxy-2-[(2-phenyl-1-piperidinyl) methyl]-1(2H)-naphthalenone, monohydrochloride

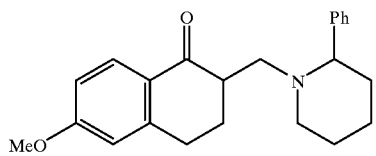

mp (°C.) 110–115. Anal. for: $C_{23}H_{27}NO_2$

Example 4

3,4-Dihydro-6-methoxy-2-[(3-phenyl-1-piperidinyl) methyl]-1(2H)-naphthalenone, monohydrochloride

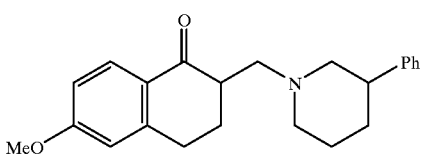

mp (°C.) 75–80. Anal. for: $C_{23}H_{27}NO_2 \cdot 1.1\ H_2O$:

Example 5

3,4-Dihydro-5-methoxy-2-[(4-phenyl-1-piperidinyl)methyl]-1(2H)-naphthalenone, monohydrochloride

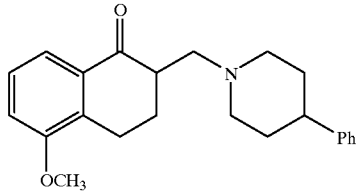

mp (°C.) 186–190. Anal. for: $C_{23}H_{27}NO_2 \cdot HCl \cdot 0.39\ H_2O$:

Example 6

6-Ethyl-3,4-dihydro-2-[(4-phenyl-1-piperidinyl)methyl]-1(2H)-naphthalenone, monohydrochloride

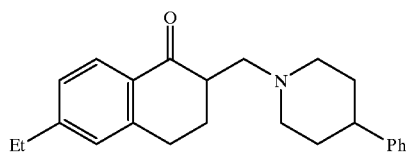

mp (°C.) 177–180. Anal. for: $C_{24}H_{29}NO \cdot HCl$:

Example 7

3,4-Dihydro-6-(phenylmethoxy)-2-(1-piperidinylmethyl)-1(2H)-naphthalenone, monohydrochloride

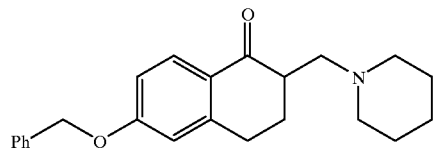

mp (°C.) 189–191. Anal. for: $C_{23}H_{27}NO_2$:

Example 8

3,4-Dihydro-6-(phenylmethoxy)-2-[(4-phenyl-1-piperidinyl)-methyl]-1(2H)-naphthalenone, monohydrochloride

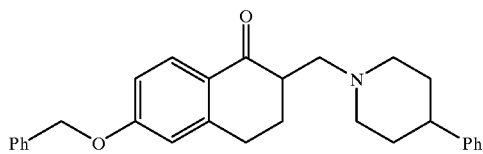

mp (°C.) 197–200. Anal. for: $C_{29}H_{31}NO_2 \cdot HCl$: Calc'd: C, 75.38; H, 6.98; N, 3.03. Found: C, 75.38; H, 7.03; N, 3.03.

Example 9

3,4-Dihydro-6-(2-phenylethoxy)-2-(1-piperidinylmethyl)-1(2H)-naphthalenone, monohydrochloride

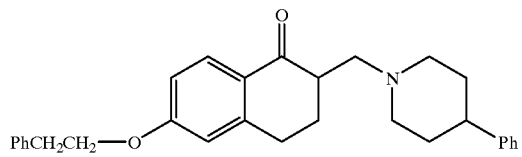

mp (°C.) 78–182. Anal. for: $C_{30}H_{33}NO_2 \cdot HCl$:

Example 10

3,4-Dihydro-6-phenoxy-2-[(4-phenyl-1-piperidinyl)methyl]-1(2H)-naphthalenone, monohydrochloride

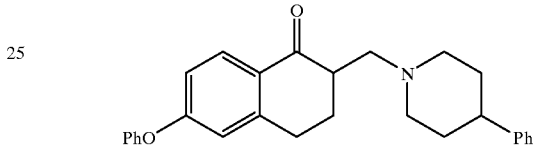

mp (°C.) 183–184. Anal. for: $C_{28}H_{29}NO_2 \cdot HCl \cdot 0.54 H_2O$:

Example 11

3,4-Dihydro-6phenyl-2-[(4-phenyl-1-piperidinyl)methyl]-1(2H)-naphthalenone, monohydrochloride

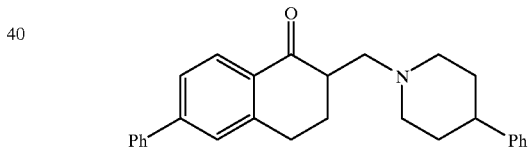

mp (°C.) 179–180. Anal. for: $C_{28}H_{29}NO \cdot HCl \cdot 0.42 H_2O$: Calc'd: C, 76.52; H, 7.07; N, 3.19. Found: C, 76.15; H, 7.04; N, 3.56.

Example 12

2,3-Dihydro-5-methoxy-2-[(4-phenyl-1-piperidinyl)methyl]-1H-inden-1-one, monohydrochloride

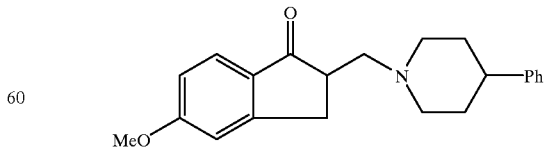

mp (°C.) 164–166. Anal. for: $C_{22}H_{25}NO_2 \cdot HCl \cdot 0.32 H_2O$: Calc'd: C, 69.95; H, 7.11; N, 3.71; Cl, 9.39. Found: C, 70.14; H, 6.99; N, 3.52; Cl, 9.61.

Example 13

3,4-Dihydro-6methoxy-2-methyl-2-[(4-phenyl-1-piperidinyl)methyl]-1(2H)-naphthalenone, monohydrochloride

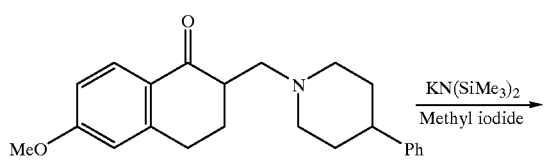

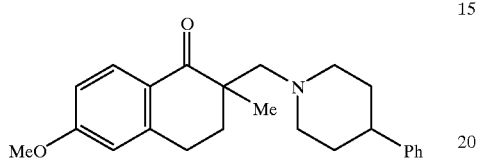

To a solution of the title compound of Example 1 (379 mg, 1.084 mmol, free base) in THF (10 mL) at −78° C. under nitrogen with stirring was added a solution of KN(SiMe$_3$)$_2$ (0.5 M in toluene, 2.39 mL, 1.19 mmol). The reaction mixture was stirred at −78° C. for 5 minutes followed by the addition of methyl iodide (0.223 mL, 3.58 mmol). The mixture was stirred at −78° C. for another 15 minutes, then kept at −16° C. for 0.5 hours followed by the addition of Et$_3$N (0.832 mL, 5.96 mmol). The mixture was quenched with saturated sodium bicarbonate and extracted with ethyl acetate. The organic layer was washed with brine, dried over magnesium sulfate and concentrated to afford a thick gummy residue. This was converted to its hydrochloride by treatment with hydrochloric to afford the title compound as a white solid, mp 185–186° C.

Using methodology analogous to that described for the title compound of Example 13, the compounds of Examples 14 to 20 were prepared:

Example 14

3,4-Dihydro-6-methoxy-2-methyl-2-[(2-phenyl-1-piperidinyl)-methyl]-1(2H)-naphthalenone, isomer A, monohydrochloride

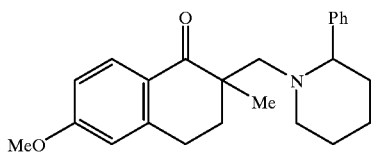

mp (°C.) 178–180. Anal. for: C$_{24}$H$_{29}$NO$_2$.HCl.0.14H$_2$O: Calc'd: C, 71.61; H, 7.58; N, 3.48. Found: C, 71.78; H, 7.30; N, 3.31.

Example 15 (isomer A)

3,4-Dihydro-6-methoxy-2-methyl-2-[(3-phenyl-1-piperidinyl)-methyl]-1(2H)-naphthalenone, isomer A, monohydrochloride

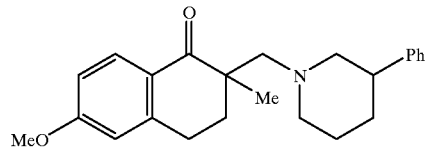

mp (°C.) 192–195. Anal. for: C$_{24}$H$_{29}$NO$_2$.HCl:

Example 16 (isomer B)

3,4-Dihydro-6-methoxy-2-methyl-2-[(3-phenyl-1-piperidinyl)-methyl]-1(2H)-naphthalenone, isomer B, monohydrochloride

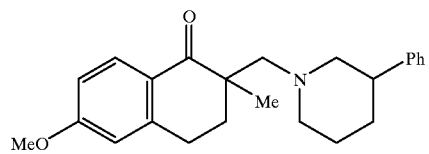

mp (°C.) 180–182. Anal. for: C$_{24}$H$_{29}$NO$_2$.HCl.0.35H$_2$O: Calc'd: C, 70.94; H, 7.62; N, 3.45. Found: C, 70.96; H, 7.56; N, 3.43.

Example 17

3,4-Dihydro-5-methoxy-2-methyl-2-[(4-phenyl-1-piperidinyl)-methyl]-1(2H)-naphthalenone, monohydrochloride

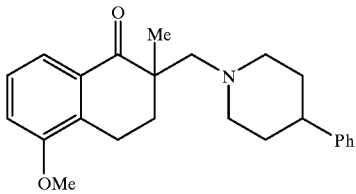

mp (°C.) 190–193. Anal. for: C$_{24}$H$_{29}$NO$_2$.HCl.0.21H$_2$O: Calc'd: C, 71.41; H7.59; N, 3.47. Found: C, 71.53; H, 7.57; N, 3.35.

Example 18

3,4-Dihydro-2-methyl-6-phenoxy-2-[(4-phenyl-1-piperidinyl)-methyl]-1(2H)-naphthalenone, monohydrochloride

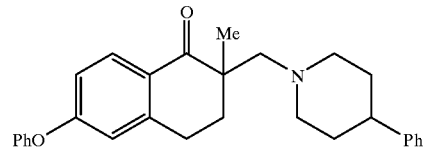

mp (°C.) 193–194. Anal. for: C$_{28}$H$_{29}$NO$_2$.HCl.0.16H$_2$O: Calc'd: C, 74.92; H, 7.01; N, 3.01. Found: C, 75.01; H, 6.96; N, 2.92.

Example 19

3,4-Dihydro-2-methyl-6-phenyl-2-[(4-phenyl-1-piperidinyl)-methyl]-1(2H)-naphthalenone, monohydrochloride

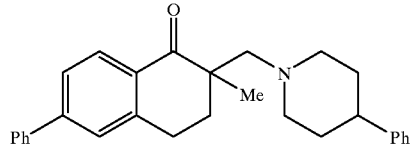

mp (°C.) 189–190. Anal. for: $C_{29}H_{31}NO \cdot HCl \cdot 0.3\ H_2O$: Calc'd: C, 77.15; H, 7.28; N, 3.10. Found: C, 77.16; H, 7.16; N, 3.09.

Example 20

1,2,3,4-Tetrahydro-6-methoxy-1-oxo-2-[2-(4-phenyl-1-piperidinyl)ethyl]-2-naphthaleneacetic acid, methyl ester, monohydrochloride

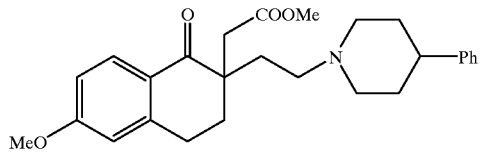

mp (°C.) 175–176. Anal. for: $C_{27}H_{33}NO_4 \cdot HCl \cdot 0.25 H_2O$: Calc'd: C, 68.05; H, 7.30; N, 2.94. Found: C, 68.04; H, 7.29; N, 2.95.

Example 21 trans- and cis-1,2,3,4-Tetrahydro-6-methoxy-2-[(4-phenyl-1-piperidinyl)methyl]-1-naphthalenol, monohydrochloride

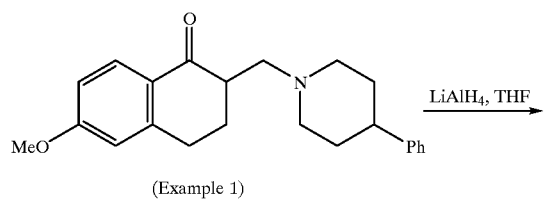

To a solution of the title compound of Example 1 (0.55 g, 1.57 mmol) in THF (10 mL) was added at 0° C. under nitrogen with stirring a 1 M solution of lithiumaluminium hydride in THF (2.36 mL, 2.36 mmol). The mixture was allowed to come to room temperature, cooled to 0° C. followed by the sequential addition of 1 mL 10% NaOH solution, MgSO$_4$ and ethyl acetate. The mixture was filtered, the filtrate was concentrated and the residue subjected to preparative HPLC (silica gel/hexane-isopropylalcohol-Et$_3$N 99:1:0.2 to 90:10:0.2 gradient) affording the faster eluting trans isomer as the major product. This was converted to its hydrochloride by treatment with HCl to afford the title compound (trans isomer) as a white solid (385 mg), mp 225–227° C. (decomposition).

The slower moving isomer was similarly converted to its hydrochloride to afford the cis compound as a white solid, mp 169–170° C.

Using methodology analogous to that described for the title compound of Example 21, the compounds of Examples 22 and 23 were prepared:

Example 22

1,2,3,4-Tetrahydro-6-methoxy-2-methyl-2-[(4-phenyl-1-piperidinyl)methyl]-1-naphthalenol, isomer A

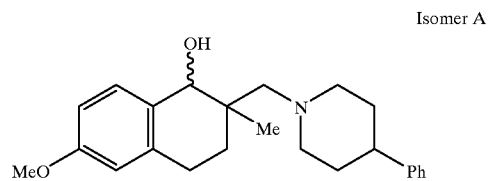

mp (°C.) 160–161. Anal. for: $C_{24}H_{31}NO_2$: Calc'd: C, 78.87; H, 8.55; N, 3.83. Found: C, 78.62; H, 8.73; N, 3.74.

Example 23

1,2,3,4-Tetrahydro-6-methoxy-2-methyl-2-[(4-phenyl-1-piperidinyl)methyl]-1-naphthalenol, isomer B, monohydrochloride

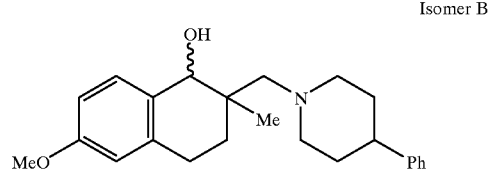

mp (°C.) 165–167. Anal. for: $C_{24}H_{31}NO_2 \cdot HCl \cdot 0.24 H_2O$: Calc'd: C, 70.95; H, 8.06; N, 3.45. Found: C, 70.96; H, 8.06; N, 3.36.

Example 24

(1S)-1,2,3,4-Tetrahydro-1-oxo-N-(1-phenylethyl)-6-(phenylmethoxy)-2-naphthalencarboxamide

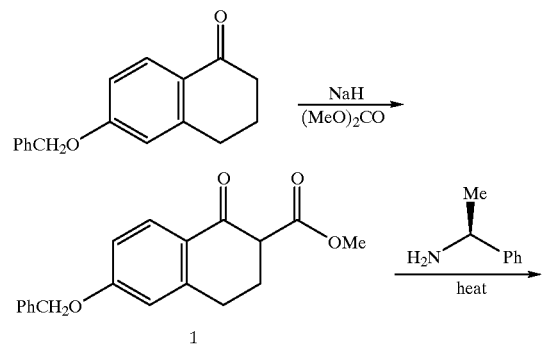

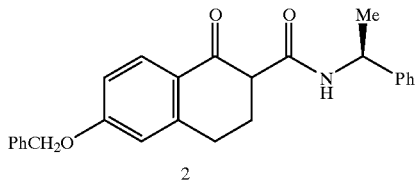

2

A. Compound 1:

A solution of 6-benzyloxy-1-tetralone (12.6 g, 50 mmol) in THF (50 mL) was added over 1 hour to a refluxing mixture of dimethyl carbonate (10.5 mL, 125 mmol) and 60% NaH (ether washed, 7 g, 175 mmol) in THF (75 mL). The recation mixture was refluxed for 14 hours, cooled to room temperature and carefully added to a stirred solution of acetic acid (25 mL) in ether (200 mL). The mixture was washed with water, the organic layer dried over $MgSO_4$ and concentrated to afford an off-white solid (compound 1).

B. (1S)-1,2,3,4-Tetrahydro-1-oxo-N-(1-phenylethyl)-6-(phenylmethoxy)-2-naphthalencarboxamide A mixture of the title A compound (1.44 g, 4.65 mmol) and (S)-α-methylbenzyamine (0.599 mL, 4.65 mmol) in toluene (15 mL) was heated under reflux for 14 hours, concentrated and the crude product was recrystallized from MeOH. The resulting product was heated under reflux for 30 minutes in toluene and concentrated to afford the title compound as an off-white solid.

Anal. for: $C_{26}H_{25}NO_3 \cdot 0.17H_2O$: Calc'd: C, 77.58; H, 6.35; N, 3.48. Found: C, 77.57; H, 5.81; N, 3.40.

Using methodology analogous to that descnbed for the title compound of Example 24, the compounds of Examples 25 to 29 were prepared:

Example 25

(1R)-1,2,3,4-Tetrahydro-1-oxo-N-(1-phenylethyl)-6-(phenylmethoxy)-2-naphthalencarboxamide

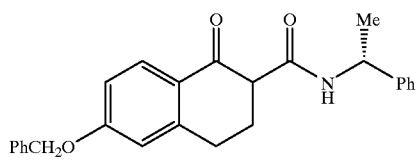

Anal. for: $C_{26}H_{25}NO_3 \cdot 0.22H_2O$: Calc'd: C, 77.40; H, 6.36; N, 3.47. Found: C, 77.42; H, 6.16; N, 3.31.

Example 26

1-[[1,2,3,4-Tetrahydro-1-oxo-6-(phenylmethoxy)-2-naphthalenyl]carbonyl]-4-phenylpiperidine

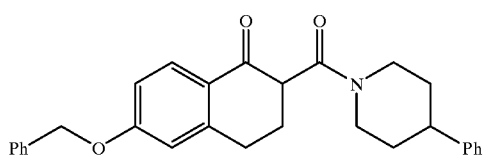

$C_{29}H_{29}NO_3$: m/e=439.

Example 27

(1R)-6-([1,1'-Biphenyl]-2-ylmethoxy)-1,2,3,4-tetrahydro-1-oxo-N-(1-phenylethyl)-2-naphthalenecarboxamide, 1:1 diastereomer mixture

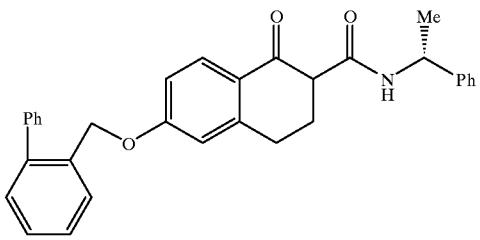

$C_{32}H_{29}NO_3$: m/e=475

Example 28

(1S)-6-([1,1'-Biphenyl]-2-ylmethoxy)-1,2,3,4-tetrahydro-1-oxo-N-(1-phenylethyl)-2-naphthalenecarboxamide, 1:1 diastereomer mixture

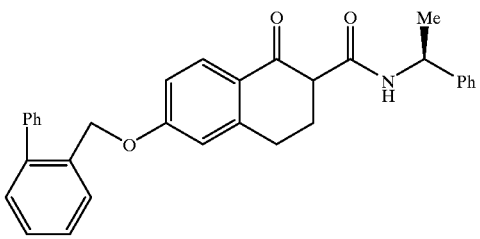

$C_{32}H_{29}NO_3$: m/e=475.

Example 29

1-[[6-([1,1'-Biphenyl]-2-ylmethoxy)-1,2,3,4-tetrahydro-1-oxo-2-naphthalenyl]carbonyl]-4-phenylpiperidine

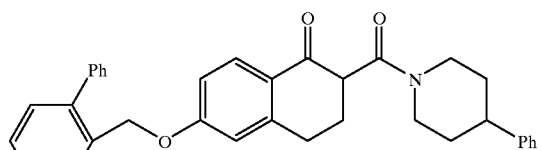

$C_{35}H_{33}NO_3$: m/e=515.

Example 30 trans-1,2,3,4-Tetrahydro-2-[[[(S)-1-phenylethyl]amino]methyl]-6-(phenylmethoxy)-1-naphthalenol, monohydrochloride

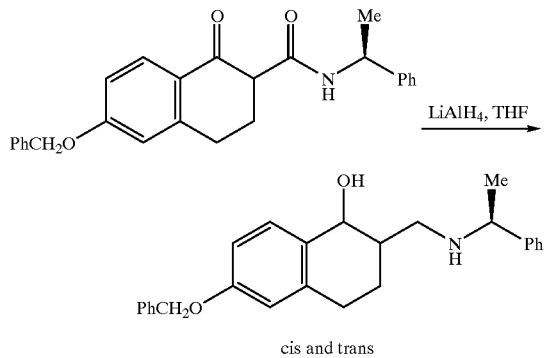

cis and trans

This compound was prepared from the title compound of Example 24 by lithiumaluminium hydride reduction in a manner similar to that described for the synthesis the title compound of Example 21. Purification of the crude product by silica gel chromatography (hexane-isopropyl alcohol-Et$_3$N 99:1:0.2 to 70:30:0.2) and isolation of the faster moving trans isomers afforded the title compound (white solid) as a 1:1 mixture of the two trans isomers.

Using methodology analogous to that described for the title compound of Example 30, compounds of Examples 31 to 34 were prepared:

Example 31 cis-6-([1,1'-Biphenyl]-2-yl)-1,2,3,4-tetrahydro-2-[[[(S)-1-phenylethyl]amino]methyl]-1-naphthalenol

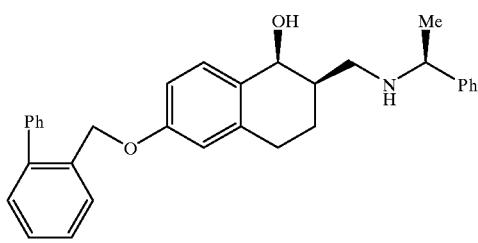

$C_{32}H_{33}NO_2$: m/e=463.

Example 32 trans-6-([1,1'-Biphenyl]-2-yl)-1,2,3,4-tetrahydro-2-[[[(S)-1-phenylethyl]amino]methyl]-1-naphthalenol, single isomer A

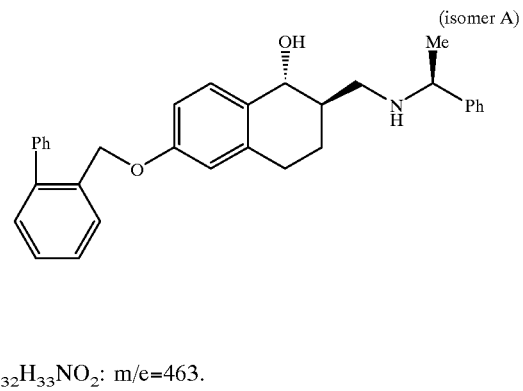

$C_{32}H_{33}NO_2$: m/e=463.

Example 33 trans-6-([1,1'-Biphenyl]-2-yl)-1,2,3,4-tetrahydro-2-[[[(S)-1-phenylethyl]amino]methyl]-1-naphthalenol, isomer B

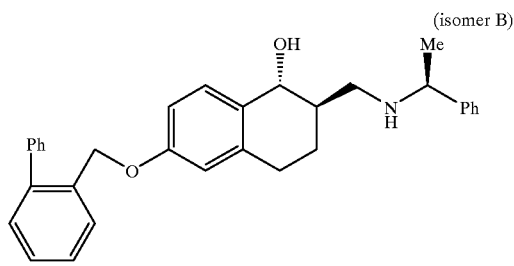

$C_{32}H_{33}NO_2$: m/e=463.

Example 34 cis-6-([1,1'-Biphenyl]-2-ylmethoxy)-1,2,3,4-tetrahydro-2-[(4-phenyl-1-piperidinyl)]methyl]-1-naphthalenol

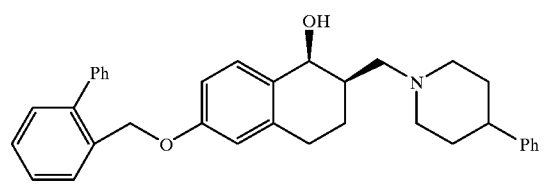

$C_{35}H_{37}NO_2$: m/e=475.

Example 35

3,4-Dihydro-6-methoxy-2-[2-oxo-2-(4-phenyl-1-pipexidinyl)ethyl]-1(2H)-naphthalenone

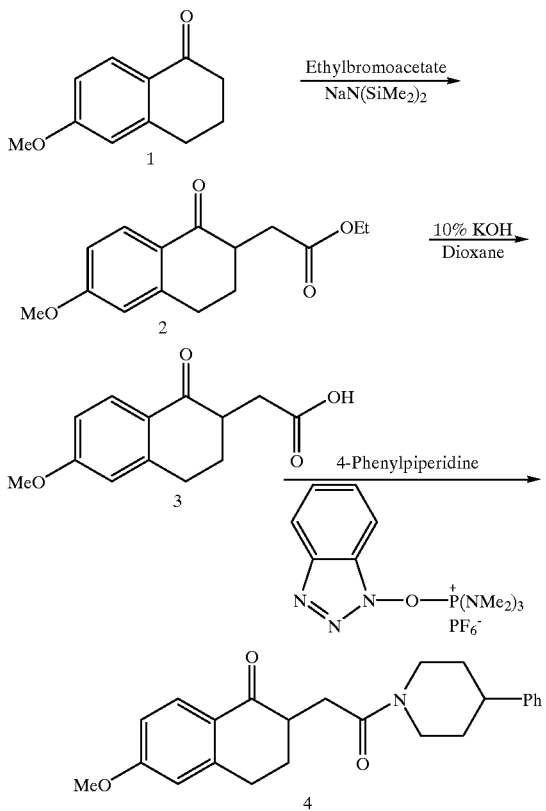

A. Compound 2:

To a solution of 6-methoxy-1-tetralone (1.76 g, 10 mmol) in THF (25 mL) was added at −78° C. under nitrogen with stirring a 1M THF solution of sodium hexamethyldisilazide (11 mL, 11 mmol) and the resulting mixture was stirred at 0° C. for 5 minutes. The reaction mixture was cooled to −78° C., then added ethyl bromoacetate (1.22 mL, 11 mmol) and stirred at room temperature for 14 hours. The reaction mixture was diluted with ethyl acetate, washed with sodium bicarbonate, dried (MgSO$_4$) and concentrated to afford compound 2 (1.75 g) as a brown gummy solid.

B. Compound 3:

To the title A compound (1.75 g) in dioxane (25 mL) was added 10% KOH (25 mL) and the reaction mixture was stirred at room temperature for 5 hours. The reaction mixture was diluted with water, washed with ether. The aqueous layer was acidified with 10% sulfuric acid and extracted with ethyl acetate. The ethyl actate extract was dried (MgSO$_4$), concentrated and the residue recrystallized from acetone to afford compound 3 (1.45 g) as an orange crystalline solid.

C. Compound 4:

To a solution of the title B compound (1.4 g, 5.98 mmol) in dry DMF (10 mL) was added squentially benzotriazole-1-yloxytris (dimethylamino)phosphonium hexafluorophosphate reagent (2.91 g, 6.58 mmol), N-methylmorpholine (0.723 mL, 6.58 mmol) and 4-phenylpiperidine (0.963 g, 5.98 mmol) and the reaction mixture was stirred at room temperature for 14 hours. The mixture was diluted with ethylacetate, washed sequentially with saturated sodium bicarbonate, dilute hydrochloric acid and saturated NaHCO$_3$. The organic layer was dried over MgSO$_4$, concentrated, and the residue subjected to flash chromatography (silica gel/hexane-EtOAc 9:1 to 1:1 gradient) to afford compound 4 as a white solid, mp 114–115° C.

Using methodology analogous to that described for the title compound of Example 35, the compounds of Examples 36 to 54 were prepared:

Example 36

1-Phenyl-4-[[1,2,3,4-tetrahydro-1-oxo-6-(phenylmethoxy)-2-naphthalenyl]acetyl]piperazine

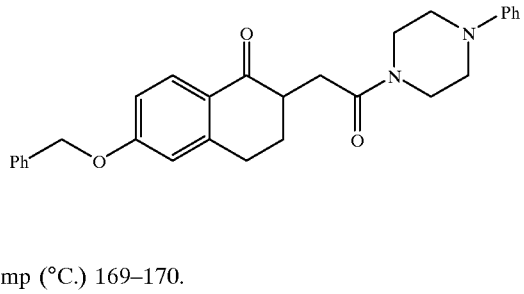

mp (°C.) 169–170.

Example 37

1,2,3,4-Tetrahydro-1-oxo-6-(phenylmethoxy)-N-[2-(2-pyridinyl)ethyl]-2-naphthaleneacetamide

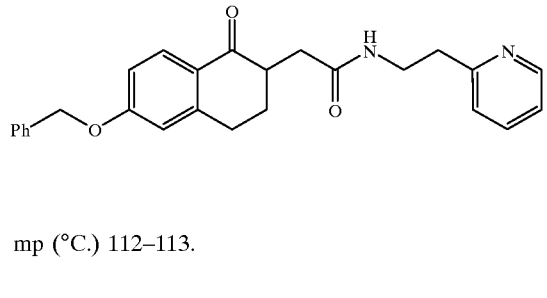

mp (°C.) 112–113.

Example 38

1,2,3,4-Tetrahydro-N,N-bis(2-methylpropyl)-1-oxo-6-(phenylmethoxy)-2-naphthaleneacetamide

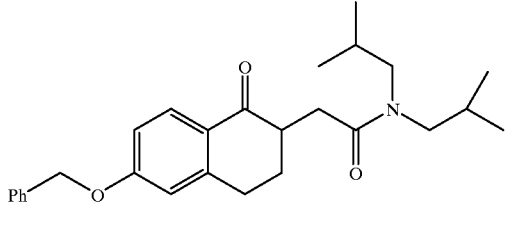

mp (°C.) 89–90.

Example 39

1-[[1,2,3,4-Tetrahydro-1-oxo-6-(phenylmethoxy)-2-naphthalenyl]acetyl]piperidine

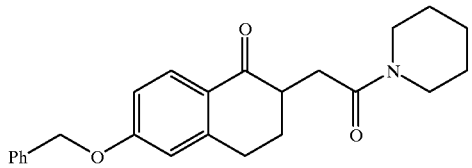

mp (°C.) 125–126.

Example 40

N-(2,3-Dihydro-1H-inden-2-yl)-1,2,3,4-tetrahydro-1-oxo-6-(phenylmethoxy)-2-naphthaleneacetamide

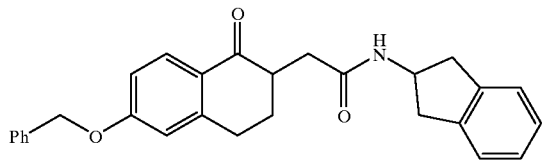

mp (°C.) 162–163.

Example 41

1-Methyl-4-[[1,2,3,4-tetrahydro-1-oxo-6-(phenylmethoxy)-2-naphthalenyl]acetyl]piperazine

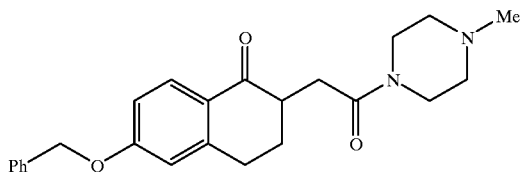

mp (°C.) 140–141.

Example 42

1,2,3,4-Tetrahydro-1-oxo-6-(phenylmethoxy)-N-(phenylmethyl)-2-naphthaleneacetamide

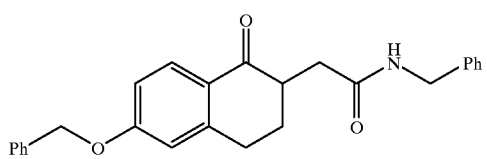

mp (°C.) 133–134.

Example 43

1,2,3,4-Tetrahydro-1-oxo-N-methyl-6-(phenylmethoxy)-N-(phenylmethyl)-2-naphthaleneacetamide

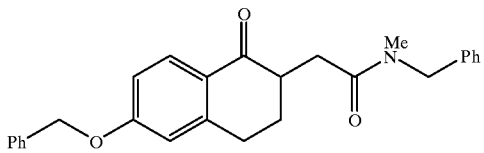

mp (°C.) 100–101.

Example 44

(1S)-1,2,3,4-Tetrahydro-1-oxo-6-(phenylmethoxy)-N-(1-phenylethyl)-2-naphthaleneacetamide

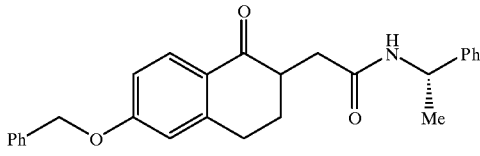

mp (°C.) 135–137.

Example 45

(1R)-1,2,3,4-Tetrahydro-1-oxo-6-(phenylmethoxy)-N-(1-phenylethyl)-2-naphthaleneacetamide

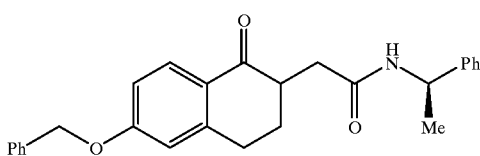

mp (°C.) 125–126.

Example 46

N-(3,3-Dimethylbutyl)-1,2,3,4-tetrahydro-1-oxo-6-(phenylmethoxy)-2-naphthaleneacetamide

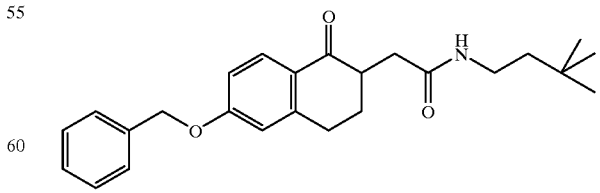

mp (°C.) 93–94. Anal. for: $C_{25}H_{31}NO_3 \cdot 0.144\ H_2$: Calc'd: C, 77.80; H, 7.96; N, 3.54. Found: C, 75.80; H, 7.92; N, 3.36.

Example 47

N-[[1,2,3,4-Tetrahydro-1-oxo-6-(phenylmethoxy)-2-naphthalenyl]acetyl]-L-valine, 1,1-dimethylethyl ester

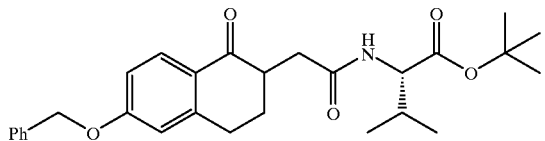

m/e=465.

Example 48

N-[[1,2,3,4-Tetrahydro-1-oxo-6-(phenylmethoxy)-2-naphthalenyl]acetyl]-L-leucine, phenylmethyl ester

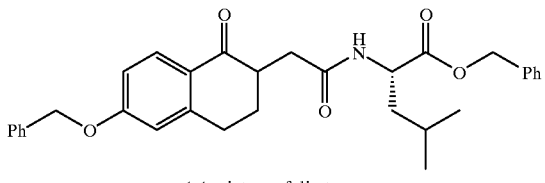

ca. 1:1 mixture of diastereomers m/e=513.

Example 49

N2-[[1,2,3,4-Tetrahydro-1-oxo-6-(phenylmethoxy)-2-naphthalenyl]acetyl]-L-phenylalaninamide

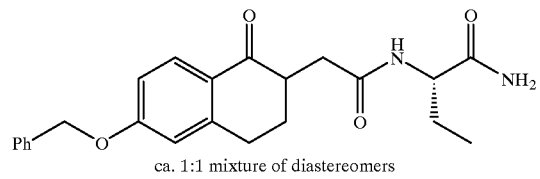

ca. 1:1 mixture of diastereomers mp (°C.) 134–135.

Example 50

N-[[1,2,3,4-Tetrahydro-1-oxo-6-(phenylmethoxy)-2-naphthalenyl]acetyl]-L-valine, ethyl ester

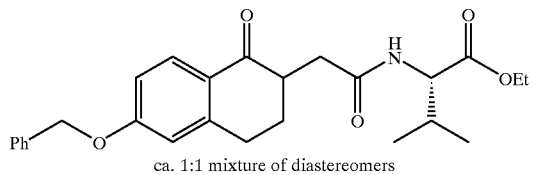

ca. 1:1 mixture of diastereomers mp (°C.) 84–85.

Example 51

N-[[1,2,3,4-Tetrahydro-1-oxo-6-(phenylmethoxy)-2-naphthalenyl]acetyl]-L-leucine, methyl ester

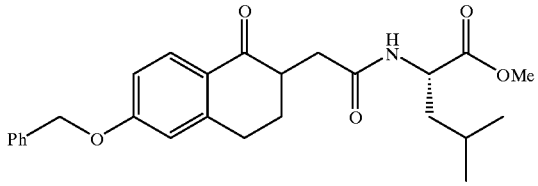

ca. 1:1 mixture of diastereomers m/e=437.

Example 52

N-[[1,2,3,4-Tetrahydro-1-oxo-6-(phenylmethoxy)-2-naphthalenyl]acetyl]-L-phenylalanine, methyl ester

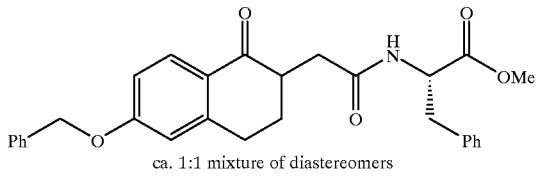

ca. 1:1 mixture of diastereomers mp (°C.) 112–113.

Example 53

N-[[1,2,3,4-Tetrahydro-1-oxo-6-(phenylmethoxy)-2-naphthalenyl]acetyl]-L-valine, methyl ester

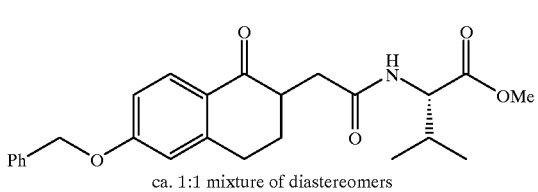

ca. 1:1 mixture of diastereomers mp (°C.) 93–94.

Example 54

N-[[1,2,3,4-Tetrahydro-1-oxo-6-(phenylmethoxy)-2-naphthalenyl]acetyl]-L-serine, phenylmethyl ester

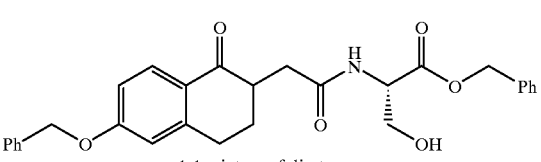

ca. 1:1 mixture of diastereomers mp (°C.) 118–119.

Example 55

1,2,3,4-Tetrahydro-6methoxy-2-(2-(4-phenyl-1-piperidinenyl)-ethyl]-1(2H)-naphthalenol, monohydrochloride

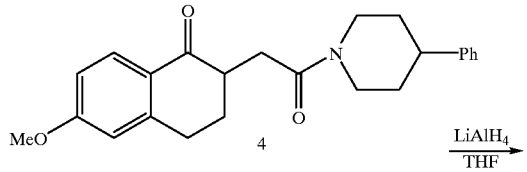

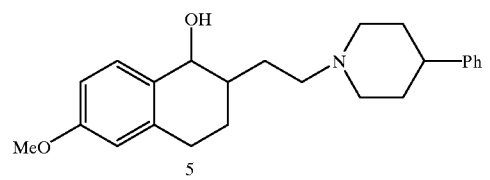

To a solution of the title C compound of Example 35 (1.2 g, 3.18 mmol) in THF (30 mL) was added at −78° C. under nitrogen with stirring a 1M THF solution of lithiumaluminum hydride (9.54 mL, 9.54 mmol). The mixture was stirred at room temperature for 12 hours, quenched by adding 3 mL 10% NaOH and dried over $MgSO_4$. The solids were removed by filtration, the filtrate concentrated and the residue dissolved in ethyl acetate. The solution was filtered through silica gel and the purified product subjected to prep. HPLC (silica/hexane-EtOAc 75:25 to 25:75 gradient) to afford three fractions; fraction 1 (650 mg, pure trans product), fraction 2 (300 mg, ca. 3:1 trans:cis mixture) and fraction 3 (105 mg, 1:1 trans:cis). Fraction 3 was converted to its HCl salt to afford the title compound as a white solid (1:1 mixture of cis:trans alcohols.

mp (°C.) 205–207. Anal. for: $C_{24}H_{31}NO_2 \cdot HCl \cdot 0.26H_2O$: Calc'd: C, 70.88; H, 8.06; N, 3.44. Found: C, 70.92; H, 7.93; N, 3.40.

Example 56 cis-6-([1,1'-Biphenyl]-2-ylmethoxy)-1,2,3,4-tetrahydro-2-[2-(4-phenyl-1-piperidinyl)ethyl]-1-naphthalenol, [R(R*,R*)]-2,3-dihydroxybutanedioate (1:1)

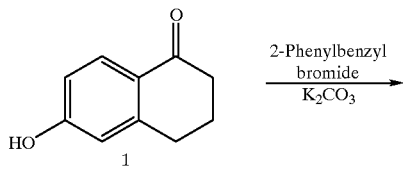

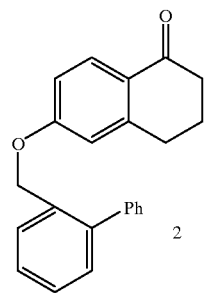

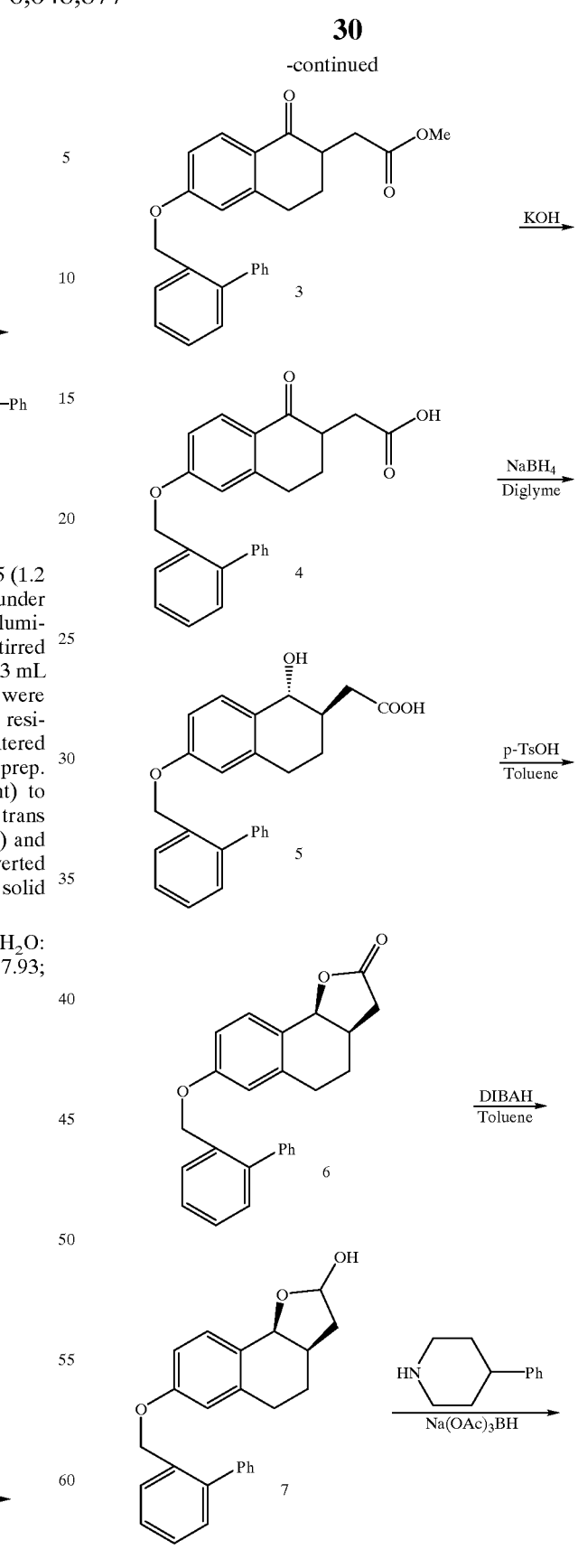

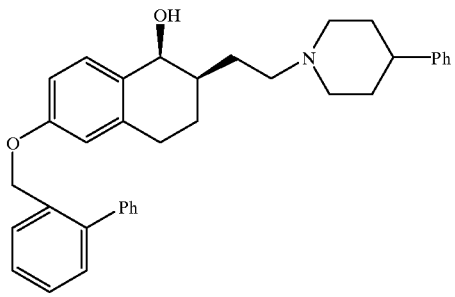

A. Compound 4:

The title compound was prepared from compound 1 by the same procedure as described for the title B compound of Example 35.

B. Compound 5:

To a solution of the keto acid 4 (10 g, 25.8 mmol) in THF (100 mL) was added dropwise to a solution of NaBH$_4$ in diglyme (0.5M, 103.1 mL, 51.6 mmol) at −78° C. The mixture was allowed to come to room temperature and stirred for 30 minutes. The mixture was cooled to 0° C., quenched to pH 4.0 by adding 0.1N HCl, extracted with EtOAc, the organic layer dried over MgSO$_4$ and concentrated to approximately 75 mL. The resulting clear solution containing compound 5 was diluted with 100 mL toluene, then added p-toluenesulfonic acid momohydrate (100 mg) and refluxed using a Daen-Stark trap for 1.5 hours. The mixture was diluted with EtOAc, washed with sat. NaHCO$_3$, dried over MgSO$_4$, concentrated and the residue recrystallized from EtOAc to afford compound 6 (6.5 g, 68%) as a grey solid.

C. Compound 7:

To a solution of the lactone 6 (5 g, 13.6 mmol) in toluene (150 mL) was added at −78° C. a solution of DIBAL in toluene (1M, 17.7 mL, 17.7 mmol) with stirring under nitrogen. The mixture was stirred at −78° C. for 5 minutes, allowed to come to 0° C. and stirred for 5 minutes, cooled to −78° C. and transferred via a cannula to a stirred (−78° C.) mixture of methylene chloride-methanol (95:5). The resulting mixture was allowed to come to room temperature, washed sequentially with 0.1 N HCl and Sat. NaHCO$_3$, the organic layer was dried over MgSO$_4$ and concentrated to afford compound 7 as a gummy white residue (5 g, 55%).

D. cis-6-([1,1'-Biphenyl]-2-ylmethoxy)-1,2,3,4-tetrahydro-2-[2-(4-phenyl-1-piperidinyl)ethyl]-1-naphthalenol, [R-(R*, R*)]-2,3-dihydroxybutanedioate (1:1)

To a solution of compound 7 (0.185 g, 0.5 mmol) and 4-phenylpiperidine (72.5 mg, 0.45 mmol) in 2 mL DMF was added acetic acid (0.029 mL, 0.5 mmol), the mixture was stirred at room temperature for 30 minutes followed by the addition of Na(OAc)$_3$BH (159 mg, 0.75 mmol). The mixture was stirred at room temperature for 12 hours, diluted with methylene chloride and washed with saturated NaHCO$_3$. The organic layer was dried over MgSO$_4$ and concentrated. The residue was filtered through silica gel using EtOAc to afford the title compound ((208 mg, 80%, free base) as a pale gummy solid. This material was converted to its (1:1) tartaric acid salt to give a white solid, m/e=516.

Using methodology analogous to that described for the title compound of Example 56, the compounds of Examples 57 to 73 were prepared:

Example 57 trans-1,2,3,4-Tetrahydro-6-(phenylmethoxy)-2-[2-(4-phenyl-1-piperidinyl)ethyl]-1-naphthalenol

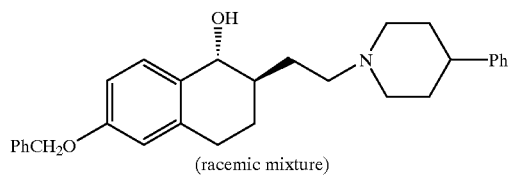

(racemic mixture)

mp (°C.) 120–121. Anal. for: $C_{30}H_{35}NO_2$: Calc'd: C, 81.59; H, 7.99; N, 3.16. Found: C, 81.50; H, 8.03; N, 3.09.

Example 58 trans-1,2,3,4-Tetrahydro-6-phenyl-2-[2-(4-phenyl-1-piperidinyl)ethyl]-1-naphthalenol

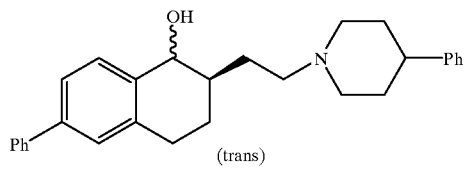

(trans)

mp (°C.) 140–141. Anal. for: $C_{29}H_{33}NO.0.08\ H_2O$: Calc'd: : C, 84.35; H, 8.09; N, 3.39. Found: C, 84.55; H, 7.79; N, 3.20.

Example 59 trans-1,2,3,4-Tetrahydro-6-phenoxy-2-[2-(4-phenyl-1-piperidinyl)ethyl]-1-naphthalenol

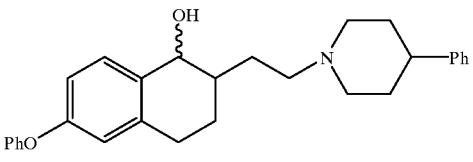

mp (°C.) 140–141. Anal. for: $C_{29}H_{33}NO_2.0.09\ H_2O$: Calc'd: : C, 81.14; H, 7.79; N, 3.26. Found: C, 81.24; H, 7.67; N, 3.17.

Example 60 trans-2-[2-[Bis(2-methylpropyl)amino]ethyl]-1,2,3, 4-tetrahydro-6-(phenylmethoxy)-1-naphthalenol

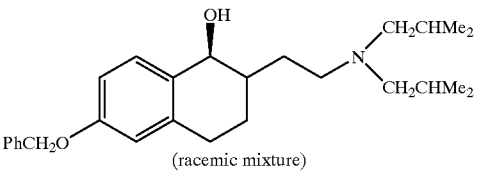

(racemic mixture)

$C_{27}H_{39}NO_2$: m/e=408.

Example 61 trans-1,2,3,4-Tetrahydro-6-(phenylmethoxy)-2-[2-(1-piperidiinyl)ethyl]-1-naphthalenol

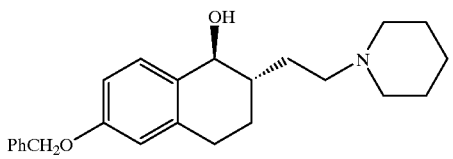

mp (°C.) 88–89. Anal. for: $C_{24}H_{32}NO_2 \cdot 0.27H_2O$: Calc'd: C, 77.83; H, 8.58; N, 3.78. Found:: C, 77.82; H, 8.34; N, 3.58.

Example 62 trans-1,2,3,4-Tetrahydro-6-(phenylmethoxy)-2-[2-[methyl(phenylmethyl)amino]ethyl]-1-naphthalenol

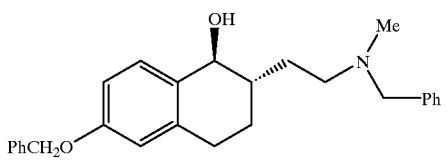

$C_{27}H_{31}NO_2$: m/e=400.

Example 63 trans-1,2,3,4-Tetrahydro-6-(phenylmethoxy)-2-[2-(4-phenyl-1-piperidinyl)ethyl]-1-naphthalenob enantiomer A

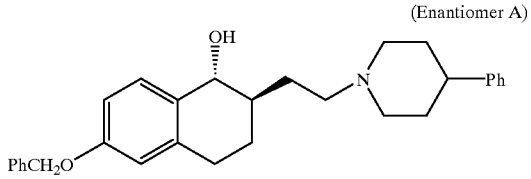

$C_{30}H_{35}NO_2$: m/e=440.

Example 64 trans-1,2,3,4-Tetrahydro-6-(phenylmethoxy)-2-[2-(4-phenyl-1-piperidinyl)ethyl]-1-naphthalenol, enantiomer B

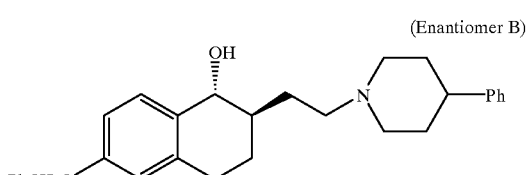

$C_{30}H_{35}NO_2$: m/e=440.

Example 65 trans-1,2,3,4-Tetrahydro-6-(phenylmethoxy)-2-[2-[[(S)-1-phenylethyl]amino]-1-naphthalenol, isomer B

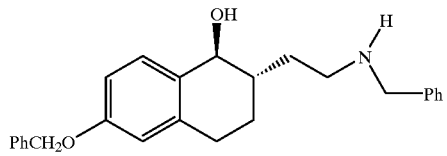

$C_{26}H_{29}NO_2$: m/e=388.

Example 66 cis-6-([1,1'-Biphenyl]-2-ylmethoxy)-1,2,3,4-tetrahydro-2-[2-[[(S)-1-phenylethyl]amino]ethyl]-1-naphthalenol, [R-(R*,R*)]-2,3-dihydroxybutanedioate (1:1)

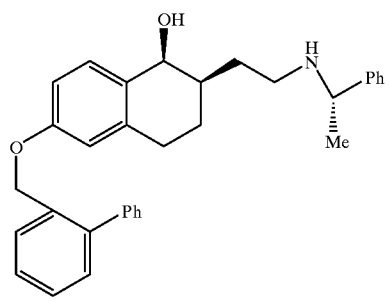

(1:1) mixture of diastereomers $C_{33}H_{35}NO_2 \cdot$tartarate (1:1) salt: m/e=476.

Example 67 cis-6-([1,1'-Biphenyl]-2-ylmethoxy)-1,2,3,4-tetrahydro-2-[2-[[(R)-1-phenylethyl]amino]ethyl]-1-naphthalenol, [R,(R*,R*)]-2,3-dihydroxybutanedioate (1:1)

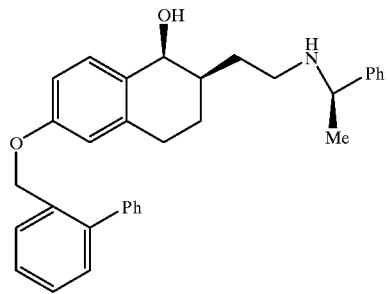

(1:1) mixture of diastereomers $C_{33}H_{35}NO_2 \cdot$tartarate (1:1) salt: m/e=476.

Example 68 trans-1,2,3,4-Tetrahydro-6-(phenylmethoxy)-2-[2-[[(R)-1-phenylethyl]amino]-1-naphthalenol, isomer A, L-tartrate (1:1)

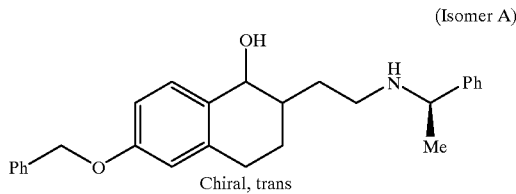
(Isomer A)

$C_{33}H_{35}NO_2$·tartarate (1:1) salt: m/e=476; αD=+44.3° (c=0.5 $CH_2Cl_2$).

Example 69 trans-1,2,3,4-Tetrahydro-6-(phenylmethoxy)-2-[2-[[(R)-1-phenylethyl]amino]-1-naphthalenol, isomer B

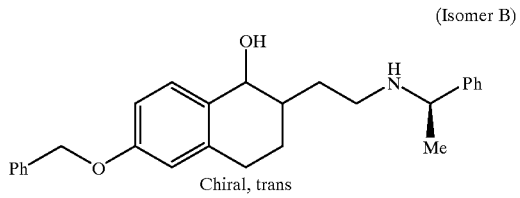
(Isomer B)

$C_{33}H_{35}N_2$·tartarate (1:1) salt: m/e=476; αD=−68° (c=0.5 $CH_2Cl_2$).

Example 70 trans-1,2,3,4-Tetrahydro-6-(phenylmethoxy)-2-[2-[[(S)-1-phenylethyl]amino]-1-naphthalenol, isomer A, L-tartrate (1:1)

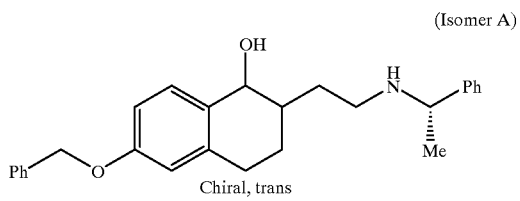
(Isomer A)

$C_{33}H_{35}NO_2$·tartarate (1:1) salt: m/e=476; αD=−44° (c=0.5 $CH_2Cl_2$).

Example 71 trans-1,2,3,4-Tetrahydro-6-(phenylmethoxy)-2-[2-[[(S)-1-phenylethyl]amino]-1-naphthalenol, isomer B

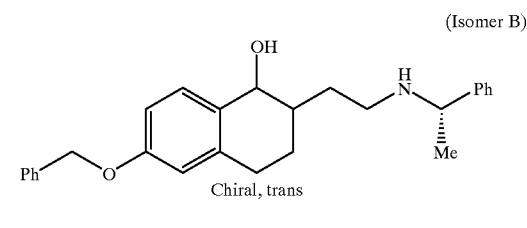
(Isomer B)

mp (°C.) 98–99.

$C_{33}H_{35}NO_2$·tartarate (1:1) salt: m/e=476; αD=−71° (c=0.5 $CH_2Cl_2$),

Example 72 trans-6-([1,1'-Biphenyl]-2-ylmethoxy)-1,2,3,4-tetrahydro-2-[2-[[(S)-1-phenylethyl]amino]ethyl]-1-naphthalenol, diastereomer A

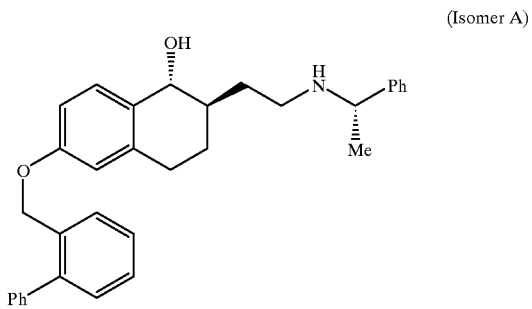
(Isomer A)

$C_{33}H_{35}NO_2$: m/e=476.

Example 73 trans-6-([1,1'-Biphenyl]-2-ylmethoxy)-1,2,3,4-tetrahydro-2-[2-[[(S)-1-phenylethyl]amino]ethyl]-1-naphthalenol, diastereomer B

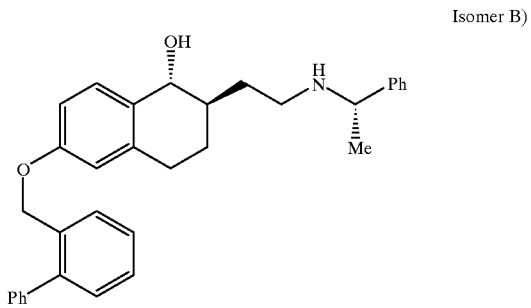
Isomer B)

$C_{33}H_{35}NO_2$: m/e=476.

Example 74

3,4-Dihydro-6-methoxy-2-[2-(4-phenyl-1-piperidinyl)ethyl]-1(2H)naphthalenone, monohydrochloride

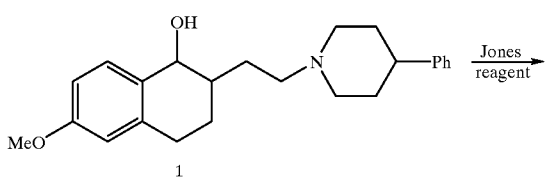

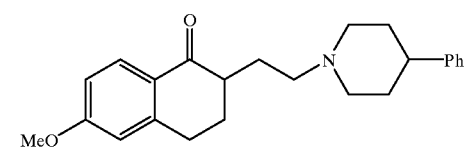

To a solution of the title compound of Example 55 (0.3 g) in 1:1 methylene chloride-acetone (10 mL) was added the Jones reagent (0.5 mL) at 0° C. C with stirring. The mixture was stirred at room temperature for 5 minutes, diluted with methylene chloride, washed with saturated sodium bicarbonate. The organic layer was dried over $MgSO_4$ and concentrated. The residue was purified by passing through Florisil® eluting with ethyl acetate to give the product as an off-white solid (160 mg). This was treated with hydrochloric and triturated with ether to afford the title compound as a white solid (161 mg, 54%), mp 250–251° C. (decomposition).

Using methodology analogous to that described for the title compound of Example 74, the compounds of Examples 75 to 77 were prepared:

Example 75

3,4-Dihydro-6-(phenylmethoxy)-2-[2-(4-phenyl-1-piperidinyl)ethyl]-1(2H)naphthalenone, monohydrochloride

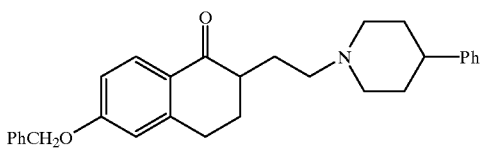

mp (°C.) 195–198. Anal. for: $C_{30}H_{33}NO_2.HCl.0.25H_2O$: Calc'd: C, 74.98; H, 7.24; N, 2.91. Found: C, 74.97; H, 7.18; N, 2.92.

Example 76

3,4Dihydro-6-phenoxy-2-[2-(4-phenyl-1-piperidinyl)ethyl]-1(2H)naphthalenone, monohydrochloride

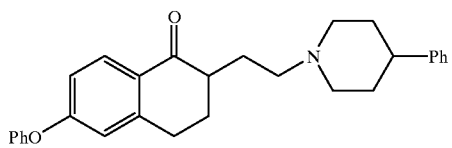

mp (°C.) 223–224. Anal. for: $C_{29}H_{31}NO_2.HCl.0.05H_2O$: Calc'd: C, 75.23; H, 6.99; N3.03. Found: C, 75.24; H, 7.00; N, 3.02.

Example 77

3,4-Dihydro-6-phenyl-2-[2-(4-phenyl-1-piperidinyl)ethyl]-1(2H)naphthalenone, monohydrochloride

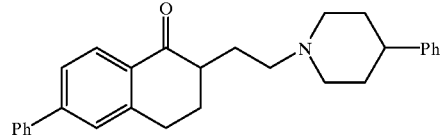

mp (°C.) 237–238. Anal. for: $C_{29}H_{31}NO.HCl.1.1H_2O$: Calc'd: C, 74.74; H, 7.40; N, 3.01. Found: C, 74.75; H, 7.24; N, 3.00.

Example 78

3,4Dihydro-2-[2-(4-phenyl-1-piperidinyl)ethyl]-6-(4-pyridinylmethoxy)010(2H)-naphthalenone, dihydrochloride

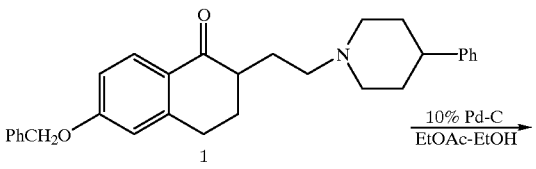

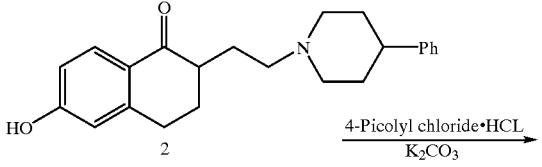

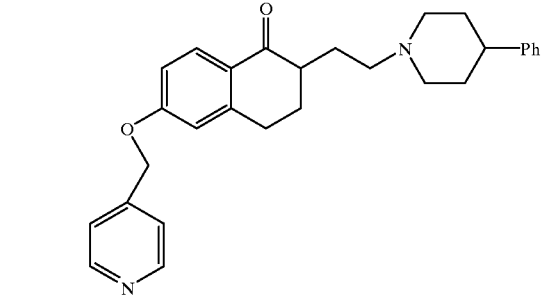

A. Compound 2:

A solution of compound 1 (600 mg, 1.36 mmol) in a 4:1 mixture of ethanol/ethyl acetate solution (24 mL) was stirred with 10% Pd-C (120 mg) at room temperature under $H_2$ (balloon) for 2 hours. The reaction mixture was filetered through a Celite pad and evaporated to dryness in vacuo. The residue was triturated with hexanes to afford compound 2 as a light tan solid (416 mg, 1.19 mmol, 88% yield), m.p. 175–177° C.

B. 3.4-Dihydro-2-[2-(4-phenyl-1-piperdinyl)ethyl]-6-(4-pyridinylmethoxy)-1-(2H)-naphthalenone, dihydrochloride To a stirring solution of compound 2 (86 mg, 0.24 mmol) in dry DMF (3 mL) at 0° C. was added pulverized potassium carbonate (170 mg, 1.23 mmol), tetrabutyl-ammonium iodide (9 mg, 0.025 mmol) and 4 -picolylchloride hydrochloride (93 mg, 0.57 mmol). The reaction mixture was stirred for 18 hours at room temperature. The reaction mixture was diluted with ethyl acetate and washed with distilled water. The organic layer was separated and the aqueous layer was backwashed with more ethyl acetate (twice). The combined organic layers were dried (MgSO$_4$) and concentrated in vacuo to yield a residue which was triturated with diethyl ether to give a brown residue. It was taken up in dichloromethane at 0° C. and treated with 4N HCl in dioxane (0.15 mL, 0.61 mmol) to yield a suspension. The suspension was concentrated in vacuo and the solid was triturated from ether to afford the title compound (93 mg, 0.18 mmol, 74% yield) as a light brown solid.

mp (°C.) 211–213. Anal. for: C$_{29}$H$_{34}$N$_2$O$_2$Cl$_2$.1.73 H$_2$O: Calc'd: C, 63.94; H, 6.93; N, 5.14. Found: C, 63.94; H, 6.63; N, 5.05.

Example 79

3,4-Dihydro-6-(2-phenylethyl)-2-[2-(4-phenyl-1-piperidinyl)-ethyl]-1(2H)naphthalenone

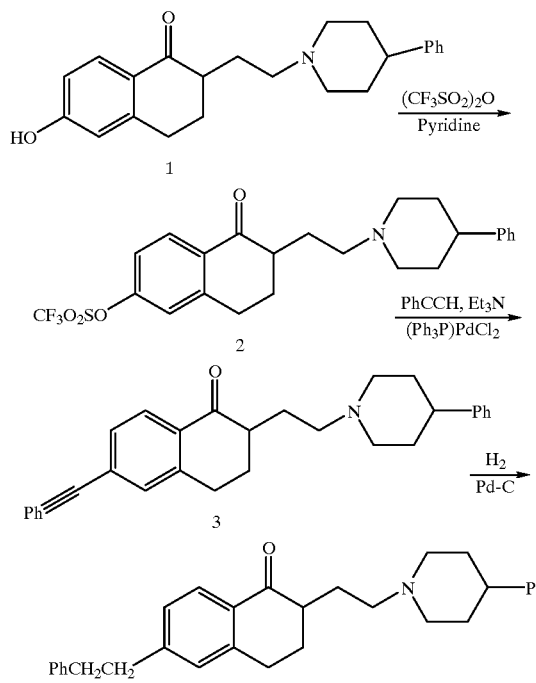

A. Compound 2:

A stirring solution of compound 1 (prepared from the title compound of Example 75 by simple hydrogenation) (400 mg, 1.14 mmol) and pyridine (645 mL, 7.98 mmol) in methylene chloride (8 mL) was cooled to 0° C. Trifluoromethanesulfonic anhydride (288 mL, 1.71 mmol) was added and the resulting solution continued to stir under Argon at 0° C. for 50 minutes. The reaction mixture was diluted with methylene chloride and sequentially washed with saturated NaHCO$_3$ solution and water. The organic phase was dried (MgSO$_4$) and concentrated in vacuo to yield a gummy residue (550 mg, 99%).

B. Compound 3:

To a solution of compound 2 (220 mg, 0.46 mmol) in dry DMF was added phenylacetylene (93 mg, 0.91 mmol) and triethylamine (274 mL, 1.97 mmol). The resulting solution was stirred under Argon for 1 minute at room temperature. Bis(triphenylphosphine)Pd(II) chloride (32 mg, 0.046 mmol) was added, and the mixture was heated to 90° C. for 20 hours. The reaction mixture was cooled to room temperature, diluted with ethyl acetate, and washed with water. The organic phase was dried (MgSO$_4$), filtered and concentrated in vacuo to yield as a dark brown residue which was purified by preparative HPLC to give compound 3 (50 mg, 25%) as a yellow solid.

mp (°C.) 137–138. Anal. for: C$_{31}$H$_{31}$NO.0.33 H$_2$O: Calc'd: C, 84.70; H, 7.26; N, 3.19. Found: C, 84.70; H, 7.09; N, 3.10.

C. 3,4-Dihydro-6-(2-phenylethyl)-2-[2-(4-phenyl-1-piperidinyl)ethyl]-1(2H)-naphthalenone Compound 3 (100 mg, 0.23 mmol) was dissolved in a mixture of 4:1 ethanol/ethyl acetate solution (25 mL) and stirred with 10% Pd on carbon (20 mg) at room temperature and under a hydrogen gas (balloon) for 18 hours. The reaction mixture was filtered through a Celite pad and evaporated to dryness. The residue was triturated with hexanes to afford the title compound as a yellow solid (103 mg, 99.9%).

mp (°C.) 93–95. Anal. for: C$_{31}$H$_{35}$NO.1.052 H$_2$O: Calc'd: C, 81.55; H, 8.19; N, 3.07. Found: C, 81.55; H, 8.04; N, 3.14.

Example 80

6-[(1,1'-Biphenyl]-2-ylmethoxy)-3,4-dihydro-2-[2-(1-piperidinyl)ethyl]-1(2H)-naphthalenone, monohydrochloride

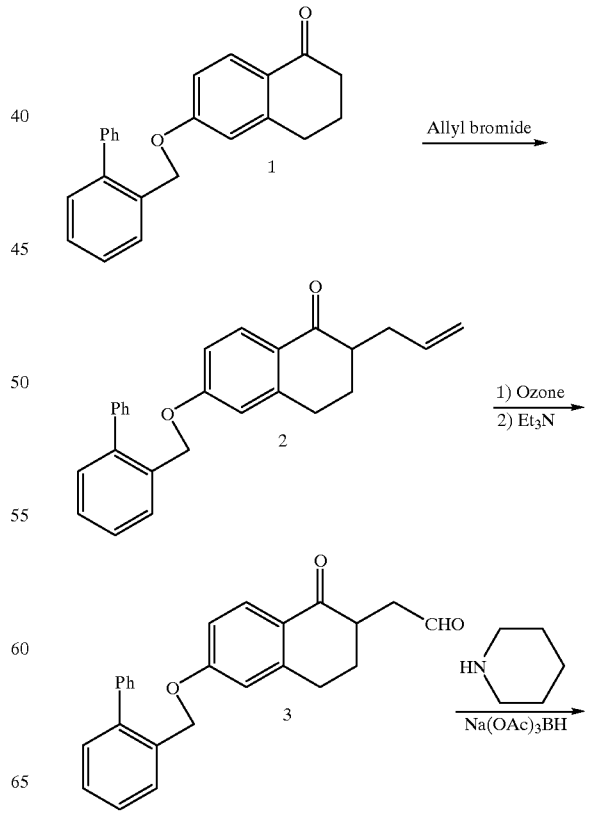

-continued

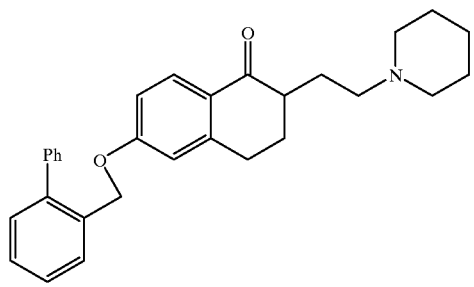

The title compound was prepared from 1 by the same procedure as described for the preparation of title C compound of Example 138a.

Using methodology analogous to that described for the title compound of Example 80, the compounds of Examples 81 to 123 were prepared:

Example 81

3,4-Dihydro-6-(2-methylpropoxy)-2-[2-oxo-2-(4phenyl-1-piperidinyl)ethyl]-1(2H)-naphthalenone

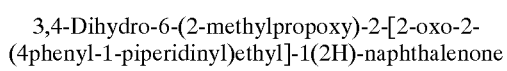

mp (°C.) 81–82. $C_{27}H_{35}NO_2$:

Example 82

3,4-Dihydro-2-[2-(4-phenyl-1-piperidinyl)ethyl]-6-(4-pyridinyhmethoxy)-1(2H)-naphthalenone, dihydrochloride

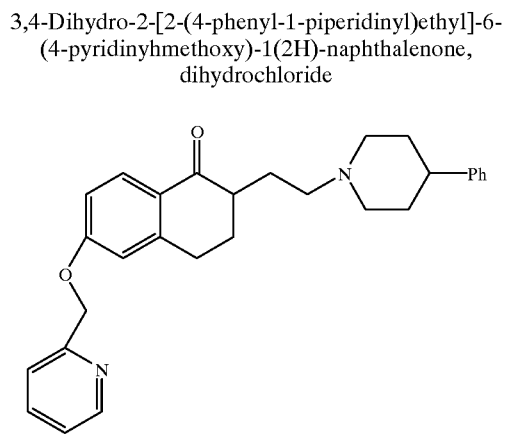

mp (°C.) 200–201. Anal. for: $C_{29}H_{32}N_2O_2 \cdot 2HCl \cdot 1.5\, H_2O$: Calc'd: C, 64.44; H, 6.90; N, 5.18. Found: C, 64.10; H, 6.70; N, 5.11.

Example 83

3,4Dihydro-2-[2-(4-phenyl-1-piperidinyl)ethyl]-6-(3-pyridinylmethoxy)-1(2H)-naphthalenone, dihydrochloride

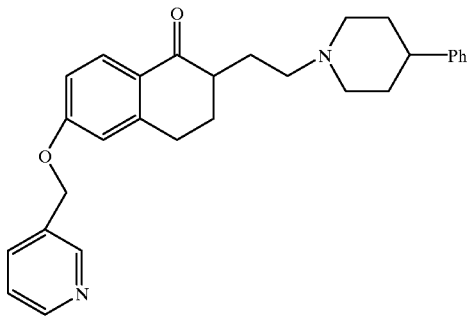

mp (°C.) 200–201. Anal. for: $C_{29}H_{32}N_2O_2 \cdot 2HCl \cdot 2.0\, H_2O$: Calc'd: C, 63.49; H, 6.96; N, 5.11. Found: C, 63.19; H, 6.78; N, 5.17.

Example 84

3,4-Dihydro-6-[(3-methylphenyl)methoxy]-2-[2-(4phenyl-1-piperidinyl)ethyl]-1(2H)-naphthalenone

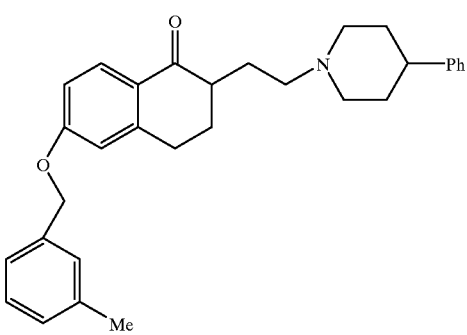

mp (°C.) 116–118. $C_{31}H_{35}NO_2$:

Example 85

6[(4-Chlorophenyl)methoxy]-3,4-dihydro-2-[2-(4-phenyl-1-piperidinyl)ethyl]-1(2H)-naphthalenone

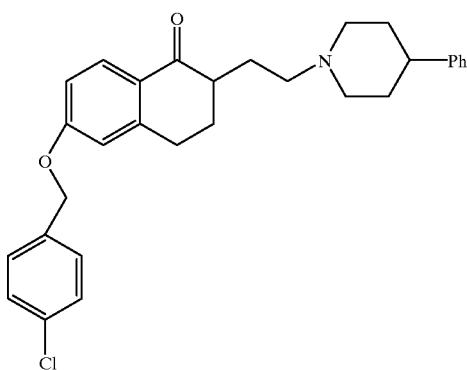

mp (°C.) 139–140. Anal. for: $C_{30}H_{31}NO_2 \cdot HCl \cdot 0.07\, H_2O$: Calc'd: C, 71.81; H, 6.82; N, 2.95. Found: C, 75.81; H, 6.58; N, 2.88.

Example 86

3,4-Dihydro-6[(4-methylphenyl)methoxy]-2-[2-(4-phenyl-1-piperidinyl)ethyl]-1(2H)-naphthalenone

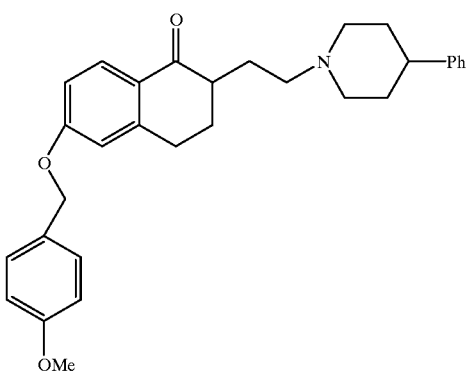

mp (°C.) 163–164. Anal. for: $C_{31}H_{35}NO_3 \cdot 0.33\ H_2O$ Calc'd: C, 78.29; H, 7.56; N, 2.95. Found: C, 78.30; H, 7.44; N, 2.77.

Example 87

6-[(2-Chlorophenyl)methoxy]-3,4-dihydro-2-[2-(4-phenyl-1-piperidinyl)ethyl]-1(2H)-naphthalenone

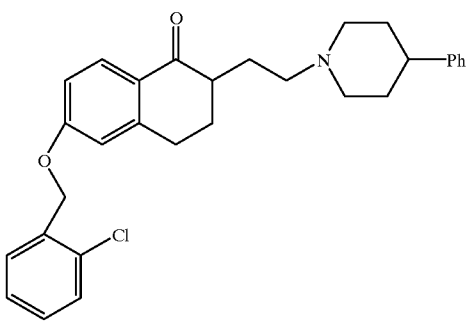

Anal. for: $C_{30}H_{31}NO_2 \cdot HCl$: Calc'd: C, 76.01; H, 6.80; N, 2.95. Found: C, 76.06; H, 6.81; N, 2.85.

Example 88

6-[(3-Chlorophenyl)methoxy]-3,4-dihydro-2-[2-(4-phenyl-1-piperidinyl)ethyl]-1(2H)-naphthalenone

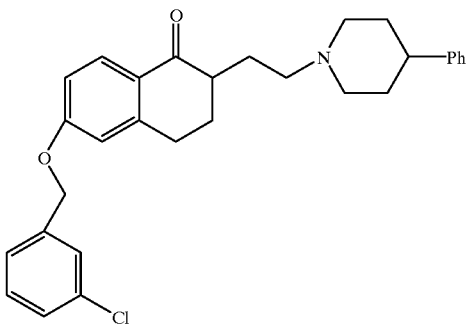

Anal. for: $C_{30}H_{32}NO_2Cl \cdot 0.013\ H_2O$. Calc'd: C, 75.97; H, 6.81; N, 2.95. Found: C, 75.97; H, 6.78; N, 2.93.

Example 89

3,4-Dihydro-6-[[4-(1-methyletyl)phenyl]methoxy]-2-[2-(4-phenyl-1-piperidinyl)ethyl]-1(2H)-naphthalenone

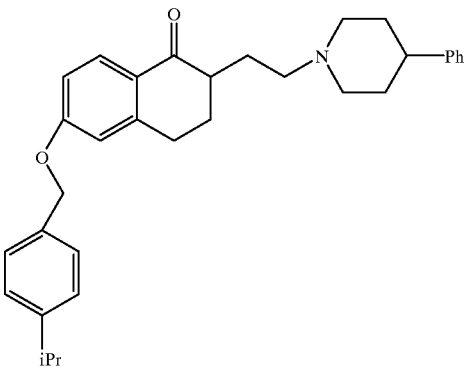

mp (°C.) 103–104. Anal. for: $C_{33}H_{39}NO_2 \cdot 0.16H_2O$: Calc'd: C, 81.81; H, 8.18; N, 2.89. Found: C, 81.81; H, 8.11; N, 2.87.

Example 90

4-[[5,6,7,8Tetrahydro-5-oxo-6-[2-(4-phenyl-1-piperidinyl)ethyl]-2-naphthalenyl]oxy]methyl]benzonitrile

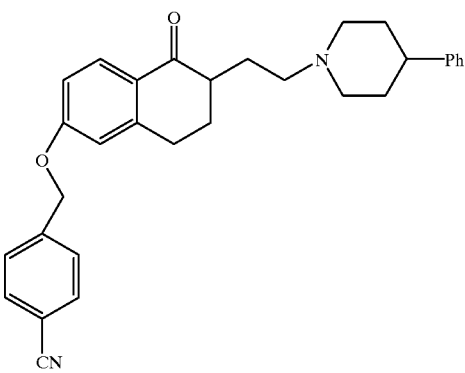

mp (°C.) 145–146. Anal. for: $C_{31}H_{32}N_2O_2 \cdot 0.01\ H_2O$: Calc'd: C, 80.11; H, 6.94; N, 6.03. Found: C, 80.11; H, 6.94; N, 5.97.

Example 91

3,4-Dihydro-5-(phenylmethoxy)-2-[2-(4-phenyl-1-piperidinyl)-ethyl-1(2H)naphthalenone, trifluoroacetate (1:1)

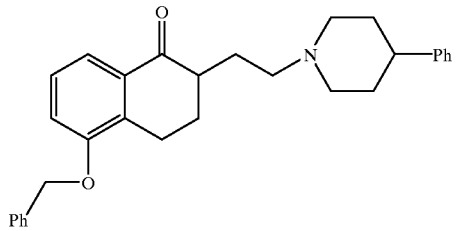

$C_{30}H_{33}NO_2 \cdot CF_3COOH$: m/e=401.

Example 92

3,4-Dihydro-6-(phenylmethoxy)-2-[2-(4-phenyl-1-piperidinyl)-ethyl]-1(²H)naphthalenone

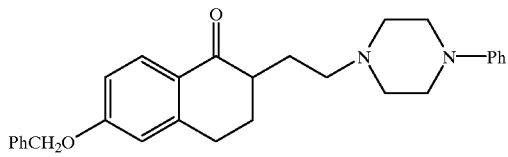

mp (°C.) 124–125. Anal. for: $C_{29}H_{32}N_2O_2$: Calc'd: C, 79.06; H, 7.32; N, 6.36. Found: C, 79.01; H, 7.27; N, 6.05.

Example 93

3,4-Dihydro-6-(phenylmethoxy)-2-[2-(2-phenyl-1-piperidinyl)-ethyl]-1(2H)naphthalenone, isomer A

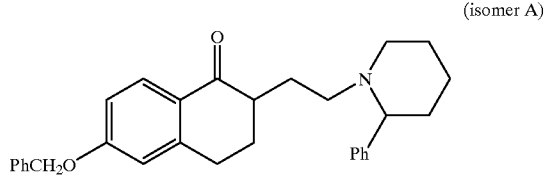

mp (°C.) 105–106. Anal. for: $C_{30}H_{33}NO_2$:

Example 94

3,4Dihydro-6-(phenylmethoxy)-2-[2-(2-phenyl-1-piperidinyl)-ethyl]-1(2H)naphthalenone, isomer B

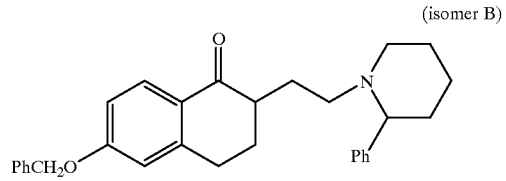

mp (°C.) 94–95. Anal. for: $C_{30}H_{33}NO_2$:

Example 94a 3,4-Dihydro-6-[(1-phenyl-1H-imidazol-2-yl)methoxy]-2-[2-(4-phenyl-1-piperidinyl)ethyl]-1(2H)-naphthalenone

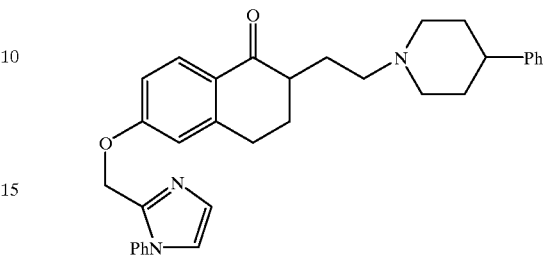

$C_{33}H_{35}N_3O_2$: m/e=505.

Example 95

3,4-Dihydro-2-[(4-phenyl-1-piperidinyl)ethyl]-6-(2,2,2-trifluoroethoxy)-1(2H)-naphthalenone, monohydrochloride

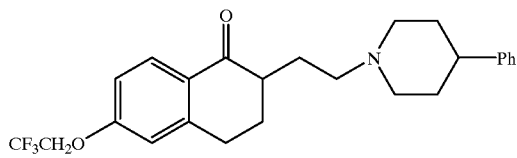

mp (°C.) 223–225. Anal. for: $C_{25}H_{28}NO_2F_3 \cdot HCl$: Calc'd: C, 64.17; H, 6.25; N, 2.99. Found: C, 64.43; H, 6.19; N, 2.85.

Example 96

3,4-Dihydro-6-[(3-nitrophenyl)methoxy]-2-[2-(4-phenyl-1-piperidinyl)ethyl]-1(2H)-naphthalenone

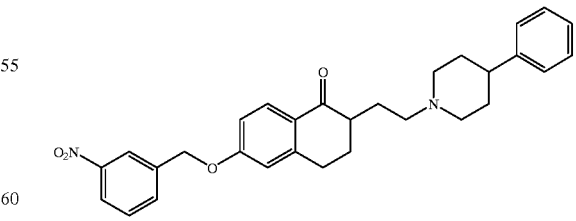

mp (°C.) 114–115. Anal. for: $C_{30}H_{32}N_2O_4 \cdot 0.11\ H_2O$: Calc'd: C, 74.05; H, 6.67; N, 5.76. Found: C, 74.05; H, 6.63; N, 5.90.

Example 97

3,4-Dihydro-6-[(2-methoxyphenyl)methoxy]-2-[2-(4-phenyl-1-piperidinyl)ethyl]-1(2H)-naphthalenone

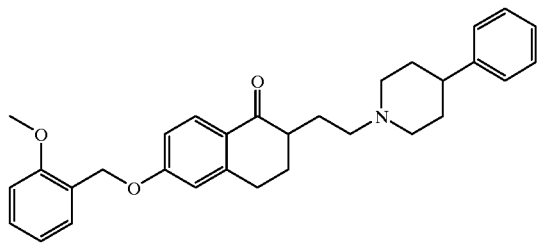

mp (°C.) 119–120. Anal. for: $C_{31}H_{35}NO_3 \cdot 0.02\ H_2O$: Calc'd: C, 79.22; H, 7.52; N, 2.98. Found: C, 79.22; H, 7.39; N, 2.77.

Example 98

3,4-Dihydro-6-[(2-nitrophenyl)methoxy]-2-[2-(4-phenyl-1-piperidinyl)ethyl]-1(2H)naphthalenone

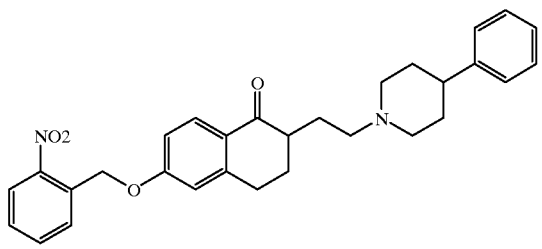

mp (°C.) 118–119. Anal. for: $C_{30}H_{32}N_2O_4 \cdot 0.66\ H_2O$: Calc'd: C, 73.87; H, 6.69; N, 5.74. Found: C, 73.87; H, 6.76; N, 5.45.

Example 99

6-([1,1'-Biphenyl]-4-ylmethoxy)-3,4-dihydro-2-[2-(4-phenyl-1-piperidinyl)ethyl]-1(2H)-naphthalenone

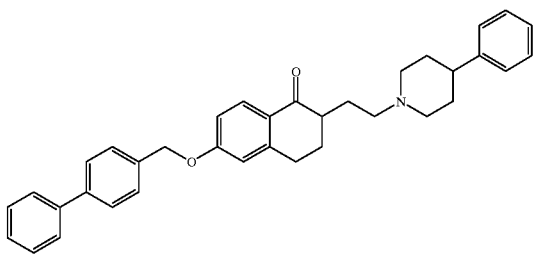

mp (°C.) 173–174. Anal. for: $C_{36}H_{37}NO_2 \cdot 0.22\ H_2O$: Calc'd: C, 83.21; H, 7.26; N, 2.70. Found: C, 83.20; H, 7.05; N, 2.74.

Example 100

6-([1,1'-Biphenyl]-2-ylmethoxy)-3,4-dihydro-2-[2-(4-phenyl-1-piperidinyl)ethyl]-1(2H)-naphthalenone

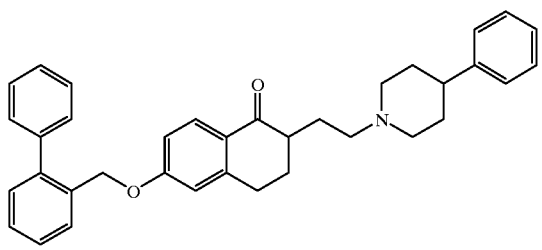

mp (°C.) 116–117. Anal. for: $C_{36}H_{37}NO_2 \cdot 0.30\ H_2O$: Calc'd: C, 82.98; H, 7.27; N, 2.69. Found:: C, 82.96; H, 7.12; N, 2.70.

Example 101

3,4-Dihydro-2-[2-(4-phenyl-1-piperidinyl)ethyl]-6-ethoxy-1(2H)naphthalenone

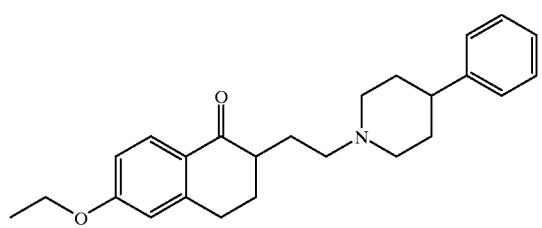

mp (°C.) 85–86. Anal. for: $C_{25}H_{31}NO_2 \cdot 0.00\ H_2O$: Calc'd: C, 79.54; H, 8.28; N, 3.71. Found: C, 79.56; H, 8.20; N, 3.60.

Example 102

3,4-Dihydro-6-[(2-methylphenyl)methoxy]-2-[2-(4-phenyl-1-piperidinyl)ethyl]-1(2H)-naphthalenone

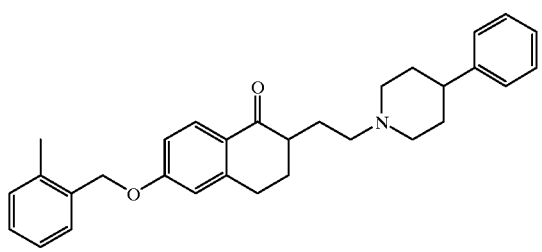

mp (°C.) 103–104. Anal. for: $C_{31}H_{35}NO_2 \cdot 0.027\ H_2O$: Calc'd: C, 81.99; H, 7.78; N, 3.08. Found: : C, 81.99; H, 7.69; N, 3.03.

Example 103

2-[[5,6,7,8-Tetrahydro-5-oxo-6-[2-(4-phenyl-1-piperidinyl)ethyl]-2-naphthalenyl]oxy]methyl]benzonitrile

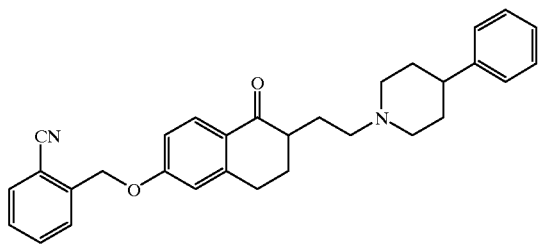

mp (°C.) 110–111. Anal. for: $C_{31}H_{32}N_2O_2 \cdot 0.187\ H_2O$: Calc'd: C, 79.56; H, 6.97; N, 5.99. Found: C, 79.56; H, 6.81; N, 5.94.

Example 104

4-[[5,6,7,8-Tetrahydro-5-oxo-6-[2-(4-phenyl-1-piperidinyl)ethyl]-2-naphthalenyl]oxy]methyl]benzoic acid, methyl ester

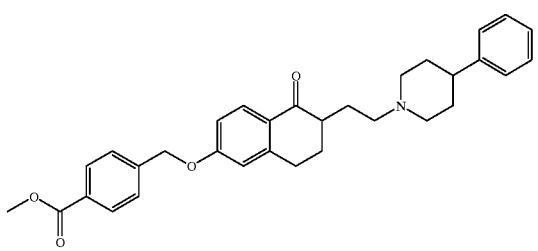

mp (°C.) 160–161. Anal. for: $C_{32}H_{35}NO_4 \cdot 0.01\ H_2O$: Calc'd: C, 77.21; H, 7.09; N, 2.81. Found: C, 77.21; H, 7.08; N, 2.78.

Example 105

3-[[5,6,7,8-Tetrahydro-5-oxo-6-[2-(4-phenyl-1-piper-idinyl)ethyl]-2-naphthalenyl]oxy]methyl]benzonitrile

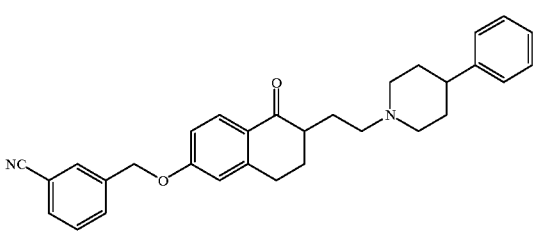

mp (°C.) 124–125. Anal. for: $C_{31}H_{32}N_2O_2 \cdot 0.15\ H_2O$: Cal'd: C, 79.68; H, 6.97; N, 5.99. Found: C, 79.68; H, 6.60; N, 5.95.

Example 106

3,4-Dihydro-6-[(4-nitrophenyl)methoxy]-2-[2-(4phenyl-1-piperidinyl)ethyl]-1(2H)-naphthalenone

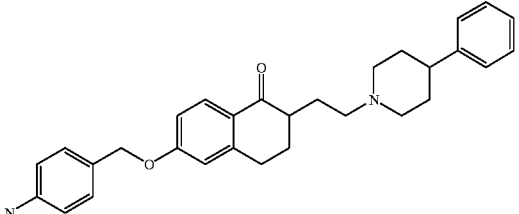

mp (°C.) 163–164. MS: $(M+H)^+$ 485. Anal. for: $C_{30}H_{32}N_2O_4 \cdot 0.325\ H_2O$: Calc'd: C, 73.47; H, 6.71; N, 5.71. Found: C, 73.47; H, 6.47; N, 5.91.

Example 107

3,4-Dihydro-6[(4-methylphenyl)methoxy]-2-[2-(4phenyl-1-piperidinyl)ethyl]-1(2H)-naphthalenone

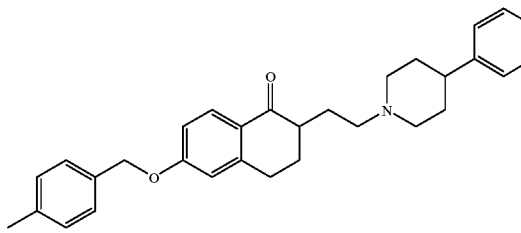

mp (°C.) 129–131. Anal. for: $C_{31}H_{35}NO_2 \cdot 0.697\ H_2O$: Calc'd: C, 79.87; H, 7.87; N, 3.00. Found: C, 79.87; H, 7.71; N, 2.90.

Example 108

3,4-Dihydro-6-[(3-methoxyphenyl)methoxy]-2-[2-(4phenyl-1-piperidinyl)ethyl]-1(2H)-naphthalenone

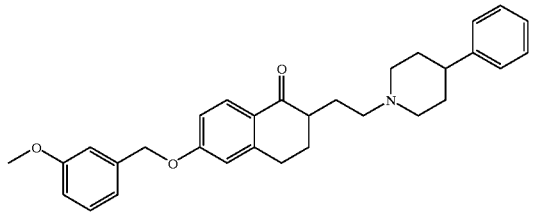

Anal. for: $C_{31}H_{35}NO_3 \cdot 0.225\ H_2O$: Calc'd: C, 78.61; H, 7.54; N, 2.96. Found: C, 78.61; H, 7.45; N, 3.22.

Example 109

3,4Dihydro-2-[2-(4-phenyl-1-piperidinyl)ethyl]-6-propoxy-1(2H)naphthalenone

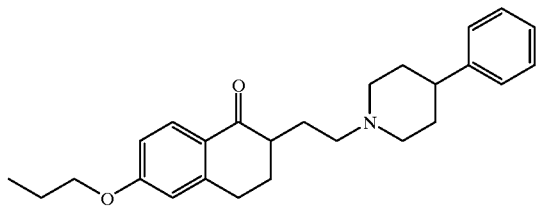

mp (°C.) 79–80. Anal. for: $C_{26}H_{33}NO_2 \cdot 0.077\ H_2O$: Calc'd: C, 79.47; H, 8.50; N, 3.56. Found: C, 79.47; H, 8.55; N, 3.50.

Example 110

3,4-Dihydro-6-(1-methylethoxy)-2-[2-(4-phenyl-1-piper-idinyl)ethyl]-1(2H)naphthalenone

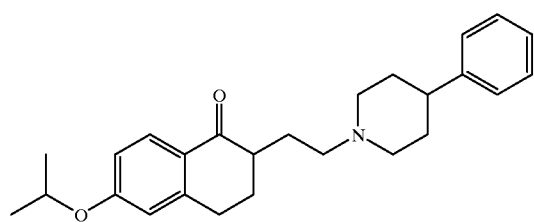

mp (°C.) 88–89. Anal. for: $C_{26}H_{33}NO_2 \cdot 0.235\ H_2O$: Calc'd: C, 78.90; H, 8.52; N, 3.54. Found: C, 78.90; H, 8.42; N, 3.42.

Example 111

3,4-Dihydro-2-[2-(4-phenyl-1-piperidinyl)ethyl]-6-[(2-propenyl)oxy]-1(2H)naphthalenone

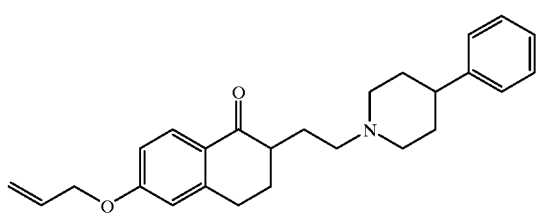

mp (°C.) 74–75. Anal. for: $C_{26}H_{31}NO_2 \cdot 0.197\ H_2O$: Calc'd: C, 79.44; H, 8.05; N, 3.56. Found: C, 79.44; H, 7.91; N, 3.44.

Example 112

3,4-Dihydro-6-(1-phenylethoxy)-2-[2-(4-phenyl-1-piper-idinyl)ethyl]-1(2H)naphthalenone, monohydrochloride

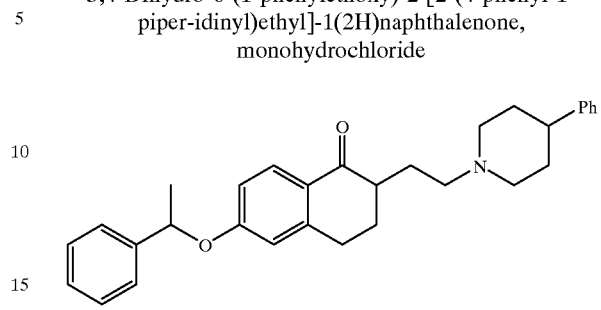

mp (°C.) 158–159. Anal. for: $C_{31}H_{36}NO_2Cl \cdot 0.49\ H_2O$ Calc'd: C, 74.63; H, 7.47; N, 2.81 Found: C, 74.63; H, 7.34; N, 2.84.

Example 113

6-(1H-Benzimidazol-2-ylmethoxy)-3,4-dihydro-2-[2-(4-phenyl-1-piperidinyl)ethyl]-1(2H)-naphthalenone, dihydrochloride

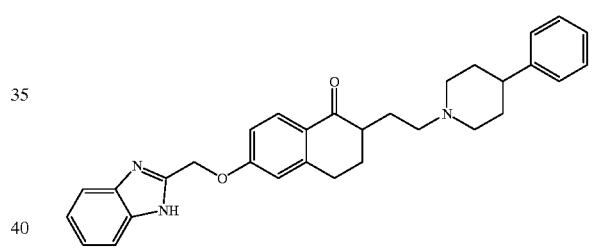

mp (°C.) 160–162.

Example 114

6-([1,1'-Biphenyl]-3-ylmethoxy)-3,4-dihydro-2-[2-(4-phenyl-1-piperidinyl)ethyl]-1(2H)-naphthalenone

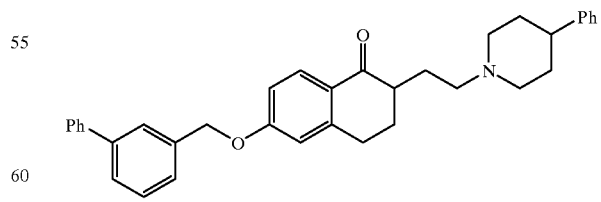

mp (°C.) 122–123. Anal. for: $C_{36}H_{37}NO_2 \cdot 0.185\ H_2O$: Calc'd: C, 83.31; H, 7.26; N, 2.70. Found: C, 83.31; H, 7.29; N, 2.59.

Example 114a 6-(Cyclopropylmethoxy)-3,4-dihydro-2-[2-(4-phenyl-1-piperidinyl)ethyl]-1(2H)-naphthalenone

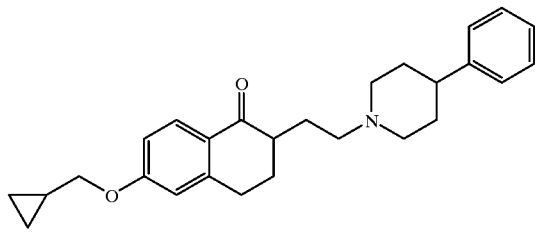

mp (°C.) 97–98. Anal. for: $C_{27}H_{33}NO_2.0.161\ H_2O$: Calc'd: C, 79.78; H, 8.26; N, 3.45. Found: C, 79.78; H, 8.22; N, 3.38.

Example 115

6-([1,1'-Biphenyl]-2-ylmethoxy)-3,4-dihydro-2-[2-(1-piperidinyl)ethyl]-1(2H)-naphthalenone, monohydrochloride

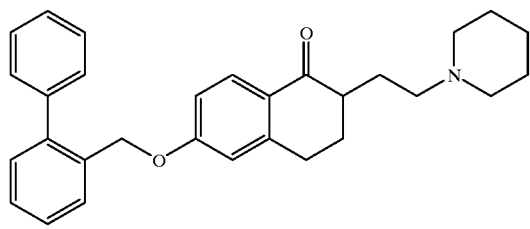

mp (°C.) 136–137. Anal. for: $C_{30}H_{34}NO_2Cl.1.31\ H_2O$: Calc'd: C, 72.12; H, 7.39; N, 2.80. Found: C, 72.11; H, 7.48; N, 2.72.

Example 116

1-[2-[1,2,3,4-Tetrahydro-1-oxo-6-(phenylmethoxy)-2-naphthalenyl]ethyl]-L-proline, 1,1-dimethylethyl ester

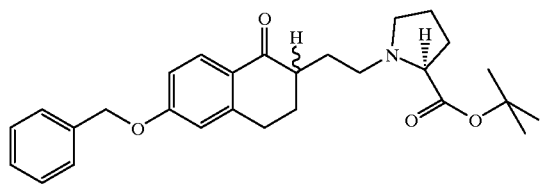

mp (°C.) 62–63. Anal. for: $C_{28}H_{35}NO_4.0.008\ H_2O$: Calc'd: C, 74.56; H, 7.86; N, 3.11. Found: C, 74.56; H, 7.88; N, 3.10.

Example 117

2-[2-[Cyclohexyl(1-methylethyl)amino]ethyl]-3,4-dihydro-6-(phenylmethoxy)-1(2H)-naphthalenone

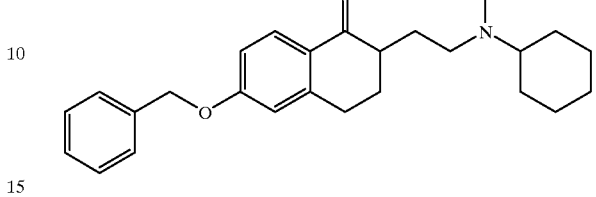

mp (°C.) 73–74. Anal for: $C_{28}H_{37}NO_2.0.10\ H_2O$: Calc'd: C, 79.81; H, 8.90; N, 3.32. Found: C, 79.81; H, 8.83; N, 3.12.

Example 118

2-[2-(2-Ethyl-1-piperidinyl)ethyl]-3,4dihydro-6-(phenylmethoxy)-1(2H)naphthalenone

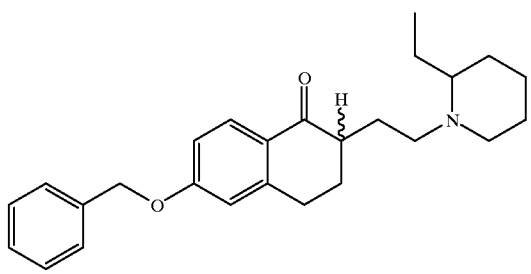

mp (°C.) 63–64° C. Anal. for: $C_{26}H_{33}NO_2$: Calc'd: C, 79.76; H, 8.49; N, 3.58. Found: C, 79.81; H, 8.50; N, 3.53.

Example 119

3,4-Dihydro-2-[2-[(S)-2-(methoxymethyl)-1-pyrrolidinyl]ethyl]-6-(phenylmethoxy)-1(2H)-naphthalenone, monohydrochloride

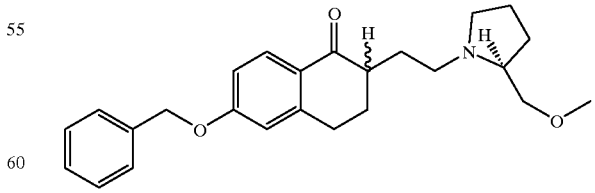

mp (°C.) 125–127. Anal. for: $C_{25}H_{32}NO_3Cl.0.383\ H_2O$: Calc'd: C, 68.73; H, 7.56; N, 3.21. Found: C, 68.73; H, 7.48; N, 2.90.

Example 120

1-[2-[1,2,3,4-Tetrahydro-1-oxo-6-(phenylmethoxy)-2-naphthalenyl]ethyl]-L-proline, phenylmethyl ester

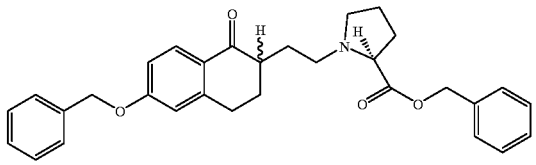

mp (°C.) 42–43. Anal. for: $C_{31}H_{34}NO_4Cl.H_2O$: Calc'd: C, 68.94; H, 6.76; N, 2.59. Found: C, 68.94; H, 6.41; N, 2.42.

Example 121

1-[2-[1,2,3,4-Tetrahydro-1-oxo-6-(phenylmethoxy)-2-naphthalenyl]ethyl]-L-prolinamide

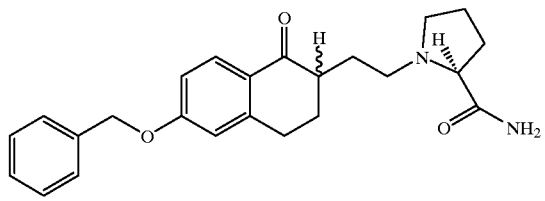

mp (°C.) 168–169. Anal. for: $C_{24}H_{28}N_2O_3.2.266H_2O$: Calc'd: C, 65.52; H, 7.57; N, 6.46. Found: C, 66,52; H, 6.90; N, 6.22.

Example 122

6-Ethoxy-3,4-dihydro-2-[2-(1-piperidinyl)ethyl]-1(2H)-naphthalenone, monohydrochloride

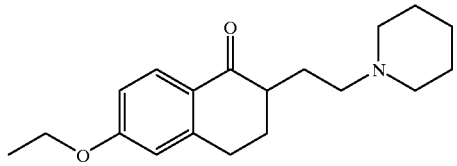

mp (°C.) 155–156. Anal. for: $C_{19}H_{28}NO_2Cl.0.292\ H_2O$: Calc'd: C, 66.50; H, 8.40; N, 4.08. Found: C, 66.50; H, 8.23; N, 3.99.

Example 123

2-[2-[Bis(1-methylethyl)amino]ethyl]-3,4-dihydro-6-(phenylmethoxy)-1(2H)-naphthalenone

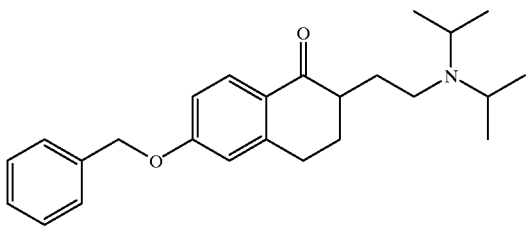

mp (°C.) 74–75. Anal. for: $C_{25}H_{33}NO_2.0.04\ H_2O$: Calc'd: C, 78.96; H, 8.77; N, 3.68. Found: C, 78.96; H, 8.78; N, 3.56.

Example 124

(Z)- and (E)-3,4-Dihydro-6-methoxy-2-methyl-2-[(4-phenyl-1-piperidinyl)methyl]-1(2H)-naphthalenone, oxine

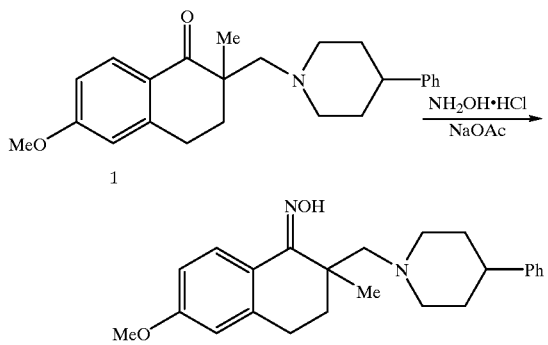

A mixture of compound 1 (title compound of Example 13) (2.33 g, 6.41 mmole), hydroxylamine hydrochloride (2.23 g, 32.0 mmole), and sodium acetate (1.89 g, 23.1 mmole) in ethanol (46 mL) was heated at 80° C. in a sealed pressure bottle. The solvent was removed and the residue was partitioned between iN sodium hydroxide solution and ethyl acetate. The organic layer was washed with saturated sodium chloride solution, dried over sodium sulfate and evaporated in vacuo to obtain 2.15 g of a tan solid. The crude product was purified by chromatography on silica gel eluting with hexane/ethyl acetate (7/3) containing 0.1% triethylamine to obtain 0.26 g (26%) of (Z)-3,4-dihydro-6-methoxy-2-methyl-2-[(4-phenyl-1-piperidinyl)methyl]-1(2H)-naphthalenone, oxime.

mp (°C.) 169–170. Anal. for: $C_{24}H_{30}N_2O_2.0.33H_2O$: Calc'd: for C, 74.96; H, 8.04; N, 7.29. Found: C, 75.07; H, 7.95; N, 7.18. and 1.0 g (41%) of (E)-3,4-dihydro-6-methoxy-2-methyl-2-[(4-phenyl-1-piperidinyl)methyl]-1(2H)-naphthalenone. mp (°C.) 174–176. Anal. for: $C_{24}H_{30}N_2O_2.0.23H_2O$: Calc'd: C, 75.32; H, 8.02; N, 7.32. Found: C, 75.38; H, 7.96; N, 7.26.

Using methodology analogous to that described for the title compound of Example 124, the compounds of Examples 125 to 133 were prepared:

Example 125

3,4-Dihydro-6-methoxy-2-[2-(4-phenyl-1-piperidinyl)ethyl]-1-(2H)naphthalenone, oxime, monohydrochloride

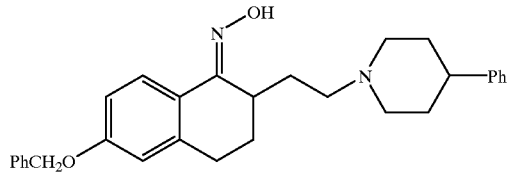

mp (°C.) 205–208. Anal. for: $C_{30}H_{34}N_2O_2 \cdot HCl \cdot 0.42H_2O$: Calc'd: C, 72.27; H, 7.24; N, 5.62. Found: C, 72.29, H, 7.24; N, 5.60.

Example 126

3,4-Dihydro-6-methoxy-2-[2-(4-phenyl-1-piperidinyl)ethyl]-1(2H)naphthalenone, oxime

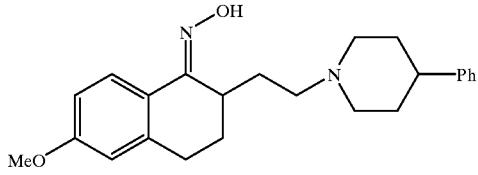

mp (°C.) 167–168. Anal. for: $C_{24}H_{30}N_2O_2 \cdot 0.79H_2O$: Calc'd: C, 73.39; H, 8.10; N, 7.13. Found: C, 73.47, H, 7.84; N, 7.05.

Example 127

3,4-Dihydro-6-methoxy-2-[2-(4-phenyl-1-piperidinyl)ethyl]-1(2H)naphthalenone hydrazone

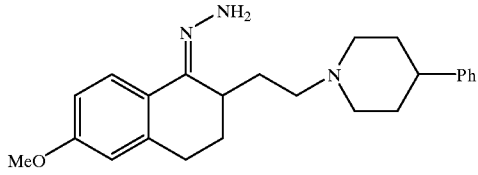

mp (°C.) 161–162. Anal. for: $C_{24}H_{31}N_3O \cdot 0.28H_2O$: Calc'd: C, 75.36; H, 8.31; N, 11.04. Found: C, 75.31; H, 8.21; N, 11.04.

Example 128

N-Methyl-2-[3,4-dihydro-6-methoxy-2-[2-(4-phenyl-1-piperidinyl)ethyl]-1(2H)-naphthalenylidene]-hydrazinecarboxamide

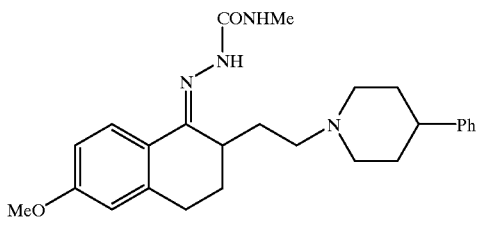

mp (°C.) 84–85. Anal. for: $C_{26}H_{34}N_4O_2 \cdot 0.68\ H_2O$: Calc'd: C, 69.88; H, 7.98; N, 12.54. Found: C, 69.81; H, 7.88; N, 11.90.

Example 129

(E)-6-([1,1'-Biphenyl]-2-ylmethoxy)-3,4-dihydro-2-[2-(4-phenyl-1-piperidinyl)ethyl]-1(2H)-naphthalenone, oxime

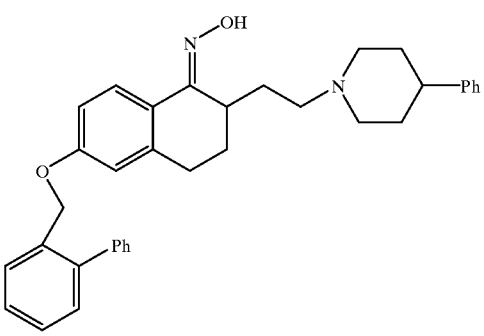

mp (°C.) 78–79. Anal. for: $C_{36}H_{38}N_2O_2 \cdot 0.27\ H_2O$: Calc'd: C, 80.74; H, 7.25; N, 5.23. Found: C, 80.74; H, 7.37; N, 4.84.

Example 130

(E)-6-([1,1'-Biphenyl]-2-ylmethoxy)-3,4-dihydro-2-[2-(1-piperidinyl)ethyl]-1(2H)-naphthalenone, oxime

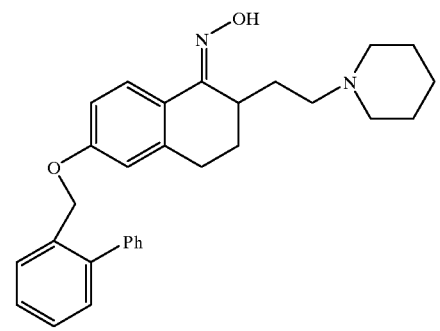

mp (°C.) 70–71. Anal. for: $C_{30}H_{34}N_2O_2 \cdot 1.3\ H_2O$: Calc'd: C, 75.41; H, 7.72; N, 5.86. Found: C, 75.41; H, 7.26; N, 5.71.

Example 131

(E)-6-Ethoxy-3,4-dihydro-2-[2-(4-phenyl-1-piperidinyl)ethyl]-1(2H)naphthalenone, oxime

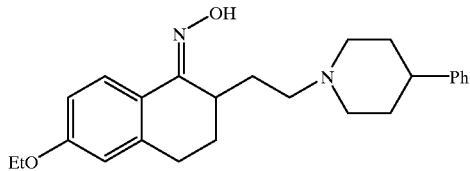

Anal. for: $C_{25}H_{32}N_2O_2 \cdot 0.21\ H_2O$: Calc'd: C, 75.75; H, 8.25; N, 7.07. Found: C, 75.75; H, 8.14; N, 6.74.

Example 132

(E)-3,4-Dihydro-2-methyl-6-(phenylmethoxy)-2-[(4-phenyl-1-piperidinyl)methyl]-1(2H)-naphthalenone, oxime

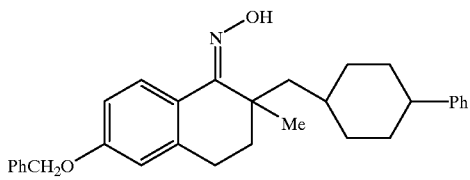

mp (°C.) 158–159. Anal. for: $C_{30}H_{34}N_2O_2 \cdot 0.02\ H_2O$: Calc'd: C, 79.20; H, 7.54; N, 6.16. Found: C, 79.20; H, 7.57; N, 5.96.

Example 133

(Z)-3,4-Dihydro-2-methyl-6-(phenylmethoxy)-2-[(4-phenyl-1-piperidinyl)methyl]-1(2H)-naphthalenone, oxime

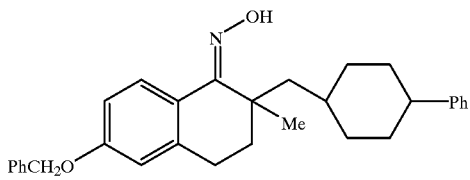

mp (°C.) 116–117. Anal. for: $C_{30}H_{34}N_2O_2 \cdot 0.02\ H_2O$: Calc'd: C, 79.20; H, 7.54; N, 6.16. Found: C, 79.19; H, 7.54; N, 5.98.

Example 134 trans-N-[1,2,3,4-tetrahydro-6-methoxy-2-methyl-2-[(4-phenyl-1-piperidinyl)methyl]-1-naphthalenyl]acetamide

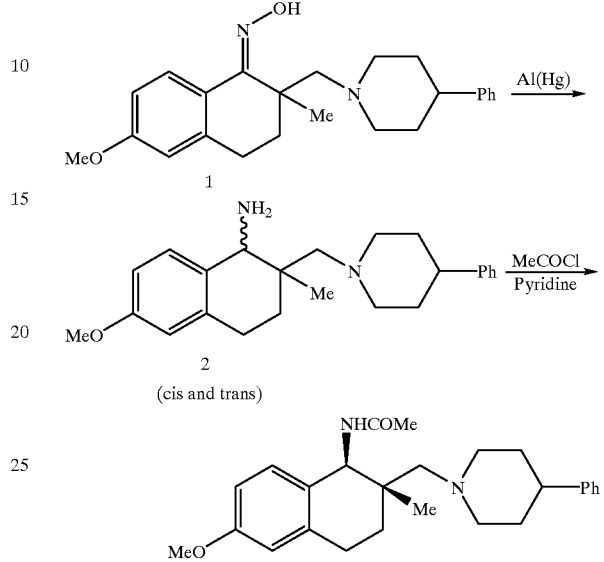

A. 1,2,3,4-Tetrahydro-6-methoxy-2-methyl-2-[(4-phenyl-1-piperidinyl)methyl]-1-naphthalenamine A suspension containing compound 1 (1.5 g, 3.96 mmol, title compound of Example 124) and excess Al(Hg) in tetrahydrofuran/water (40 mL, 90:10) was heated under reflux for 18 hours. The reaction mixture was cooled to room temperature, filtered and the filtrate was washed with brine and dried over anhydrous magnesium sulfate. The solvent was evaporated and the residue was purified by flash chromatography on silica gel (10% methanol in dichloromethane) to give two products which were converted to their hydrochloride salts by treatment with hydrochloric acid.

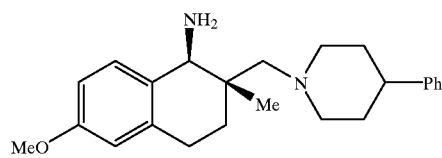

trans-isomer (543 mg, 37.6%). mp (°C.) 195–205 (decomposition). Anal. for: $C_{24}H_{32}N_2O \cdot 2HCl \cdot 0.9H_2O$: Calc'd: C, 63.49; H, 7.96; N, 6.17; Cl, 15.62. Found: C, 63.50; H, 7.94; N, 6.11; Cl. 15.29.

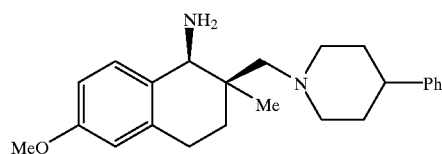

cis-isomer (543 mg, 37.6%). mp (°C.) 217–219 (decomposition). Anal. for: $C_{24}H_{32}N_2O \cdot HCl \cdot 0.9H_2O$: Calc'd: C,71.89; H, 8.29; N, 6.99 Found: C, 71.76; H,8.35; N, 6.99.

B. trans-N-[1,2,3,4-tetrahydro-6-methoxy-2-methyl-2-[(4-phenyl-1-piperidinyl)methyl]-1-naphthalenyl]-acetamide To a solution of compound 2 (trans isomer) 205 mg, 0.56 mmole) and pyridine (0.2 mL) in methylene chloride (2.0 mL) cooled to 0° C. was added acetyl chloride (48.6 mg). The reaction mixture was stirred at room temperature for two hours and partitioned between 1N sodium hydroxide solution and ethyl acetate. The organic fraction was washed with saturated sodium chloride solution and dried over sodium sulfate. The solvent was recovered in vacuo to obtain 203 mg of a white solid. The crude product was purified by crystallization from hexane/ethyl acetate to obtain the title compound (180 mg, 79) as a white solid.

mp (°C.) 186–188. Anal. for: $C_{26}H_{34}N_2O_2$: Calc'd: C, 76.81; H, 8.43; N, 6.89. Found: C, 76.68; H, 8.44; N, 6.88.

Example 135 cis-N-[1,2,3,4-tetrahydro-6-methoxy-2-methyl-2-[(4-phenyl-1-piperidinyl)methyl]-1-naphthalenyl]acetamide

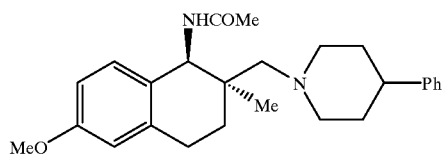

The title A compound of Example 134 (cis isomer, 153 mg, 0.42 mmol) was converted to the desired product in the same manner as described for the title compound of Example 133, part B. The product was purified by crystallization from isopropyl ether to obtain the title compound as a colorless solid (141 mg, 83%).

mp (°C.) 140–142. Anal. for: $C_{26}H_{34}N_2O_2$: Calc'd: C, 76.81; H, 8.43; N, 6.89. Found: C, 76.71; H, 8.52; N, 6.79.

Example 136

1',2',3',4'-Tetrahydro-6'-methoxy-2'-[2-(4-phenyl-1-piperidinyl)ethyl]spiro[imidazolidine4,1'(2'H)-naphthalene]-2,5-dione

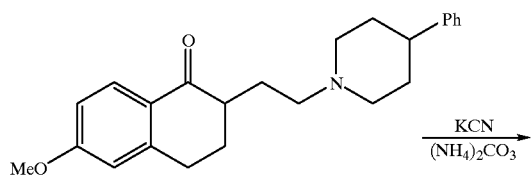

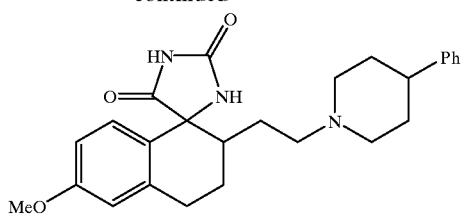

A mixture of compound 1 (free base, 0.95 g, 2.62 mmol, title compound of Example 74), potassium cyanide (0.596 g, 9.16 mmol) and ammonium carbonate (3.27 g, 34 mmol) in formamide (40 mL) was heated in a 50 mL sealed tube at 75° C. for 12 hours and then at 115–120° C. for 50 hours. The mixture was poured over cold aqueous solution of $NaHCO_3$, stirred for 10 minutes, filtered, and the solid product recrystallized repeatedly from hot DMF to give the title compound as a white solid (isomer A), mp 242–243° C. The mother liquor was concentrated and the residue recrystallized from for DMF to afford the title compound as a white solid, m. p. 288–289.

Using methodology analogous to that described for the title compound of Example 136, the compound of Example 137 were prepared:

Example 137

1',2',3',4'-Tetrahydro-6'-(phenylmethoxy)-2'-[2-(4-phenyl-1-piperidinyl)ethyl]spiro[imidazolidine-4,1'(2'H)-naphthalene]-2,5-dione, isomer A Isomer A: mp 245–246° C. Isomer B: mp 275–246° C.

Example 138

5,6,7,8-Tetrahydro-5-oxo-6-[2-(4-phenyl-1-piperidinyl)ethyl]-2-naphthalenecarboxylic acid, methyl ester

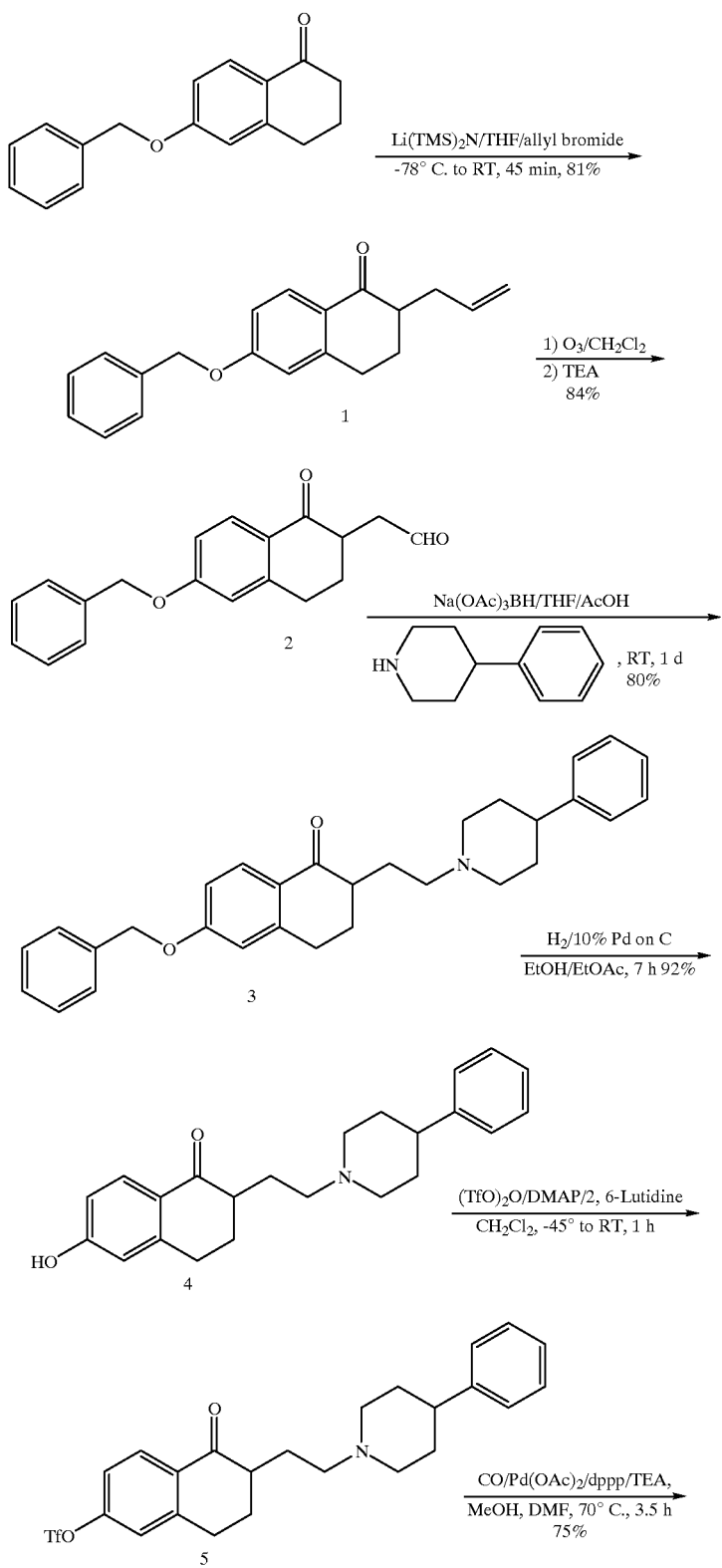

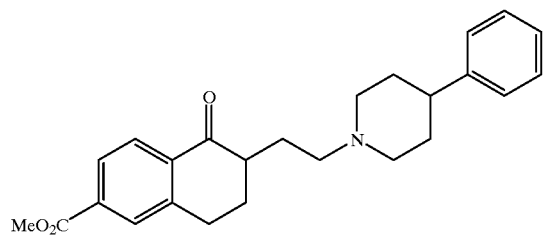

A. 3,4-Dihydro-2-(2-propenyl)-6-(phenylmethoxy)-1(2H)naphthalenone

Lithium bis(trimethylsilyl)amide (1 M in THF, 150 mL, 0.15 mol) was added over 20 minutes to a solution of 6-benzyloxytetralone (37 g, 0.14 mol) in dry THF (580 mL) stirring at −78° C. under argon in a flame dried flask. HMPA (26 mL, 0.15 mol) was added and then the −78° C. bath was replaced with a 0° C. bath. After 10 minutes, allyl bromide (49 mL, 0.58 mol) was added quickly in one portion. After stirring at ambient temperature for 45 minutes, the reaction was quenched with water (56 mL). The reaction was transferred to a separatory funnel with ether/1 N HCl. Extraction with ether (2×600 mL), washing the combined organic layers with water, saturated NaHCO$_3$, water, and brine, and drying over MgSO$_4$ afforded 48 g of crude product. A series of 4 flash chromatographies (silica, 75 mm dia., 10% EtOAc/hexane) afforded 34 g (81%) of the title compound. R$_f$ (silica, 25% EtOAc/hexane)=0.50.

B. 1,2,3,4-Tetrahydro-6-(phenylmethoxy)-1-oxo-2-naphthaleneacetaldehyde

Ozone generated by a Welsbach Ozonizer was bubbled into a solution of the title A compound (16 g, 55 mmol) in CH$_2$Cl$_2$ (1 l) stirring at −78° C. until the blue color persisted (~2 hours). Nitrogen was then bubbled through the reaction to discharge the blue color and then for 30 minutes after the blue color had dissapated. Triethylamine (16 mL, 110 mmol) was added dropwise over 15 minutes and the reaction was stirred at ambient temperature. After 1 hour, the reaction was transferred to a separatory funnel and washed with 0.5 M HCl, water, and brine and dried over MgSO$_4$ to afford 18 g of crude product after evaporation of the solvent. Flash chromatography (silica, 75 mm dia., 25% EtOAc/hexane and flushed with EtOAc) afforded 14 g (84%) of the title compound. R$_f$ (silica, 25% EtOAc/hexane)=0.20.

C. 3,4-Dihydro-6-(phenylmethoxy)-2-[2-(4-phenyl-1-piperidinyl)ethyl]-1(2H)naphthalenone Sodium triacetoxyborohydride (14 g, 64 mmol) was added to a stirring solution of 4-phenylpiperidine (7.4 g, 46 mmol), the title B compound (12 g, 41 mmol), and acetic acid (2.4 mL, 41 mmol) in THF (360 mL). After stirring at ambient temperature for 1 day, the reaction was diluted with CH$_2$Cl$_2$ and transferred to a separatory funnel. Washing the combined organic layers with ½ saturated NaHCO$_3$ and brine and drying over MgSO$_4$ afforded 19 g of crude product after evaporation of the solvent. Recrystallization from ethanol afforded 12 g of product. Flash chromatography (silica, 50 mm dia., 3% MeOH/CH$_2$Cl$_2$) of the mother liquors afforded an additional 3.9 g (total 16 g, 80%) of the title compound.

D. 3,4-Dihydro-6-hydroxy-2-[2-(4-phenyl-1-piperidinyl)ethyl]-1(2H)naphthalenone

A suspension of 10% Pd/C (3.3 g) and the title C compound (16 g, 37 mmol) in ethanol (630 mL) and ethyl acetate (160 mL) was stirred under a balloon of hydrogen. After 7 hours, the reaction was filtered through a pad of Celite (AFA) rinsing with CH$_2$Cl$_2$. The filtrate was evaporated in vacuo to afford 12 g (92%) of the title compound.

E. 3,4-Dihydro-6-(trifluoromethanesulfonyloxy)-2-[2-(4-phenyl-1-piperidinyl)ethyl]-1(2H)naphthalenone 4-Dimethylaminopyridine (0.83 g, 6.8 mmol) was added to a solution in phenol of the title D compound (12 g, 34 mmol) in CH$_2$Cl$_2$ (dried by passing through a column of Act. I alumina, 280 mL) stirring at −45° C. 2,6-Lutidine (4.8 mL, 41 mmol) and triflic anhydride (6.8 mL, 41 mmol) were then added and the cold bath was removed. After stirring at ambient temperature for 1 hour, the reaction was transferred to a separatory funnel with ether (500 mL). Washing the organic layer with water (250 mL), 0.5 M HCl (250 mL), saturated NaHCO$_3$ (250 mL), and brine (250 mL) and drying over Na$_2$SO$_4$ afforded the title compound (15 g) as a pink solid after evaporation of the solvent.

F. 5,6,7,8-Tetrahydro-5-oxo-6-[2-(4-phenyl-1-piperidinyl)ethyl]-2-naphthalenecarboxylic acid, methyl ester Palladium acetate (31 mg, 0.14 mmol) and 1,3-bis(diphenylphosphino)propane (57 mg, 0.14 mmol) were added to a solution of the title E compound (2.2 g, 4.6 mmol) and triethylamine (1.3 mL, 9.2 mmol) in methanol (1.5 mL) and dimethylformamide (8 mL). Carbon monoxide was bubbled through the resulting mixture for 10 minutes and then the reaction was stirred under a balloon of CO at 70° C. After 3.5 hours, the reaction was diluted with CH$_2$Cl$_2$ (100 mL) and washed with brine (2×40 mL) to afford 1.8 g of crude product after evaporation of the solvent. Flash chromatography (silica, 37 mm dia., 3% MeOH/CH$_2$Cl$_2$) afforded 1.4 g (75%) of the title compound. mp 110.0–112.0° C.; LRMS (Electrospray, 0.1% NH$_4$OH/CH$_3$CN, pos. ion spectrum)

m/z 392 (M+1); R$_f$ (silica, 5% MeOH/CH$_2$Cl$_2$)=0.15. Anal. for: C$_{25}$H$_{29}$NO$_3$.0.66 H$_2$O: Calc'd: C, 74.42; H, 7.58; N, 3.47. Found: C, 74.42; H, 7.41; N, 3.17.

Example 138a 5,6,7,8-Tetrahydro-5-oxo-N-phenyl-6-[2-(4-phenyl-1-piperidinyl)ethyl]-2-naphthalenecarboxamide

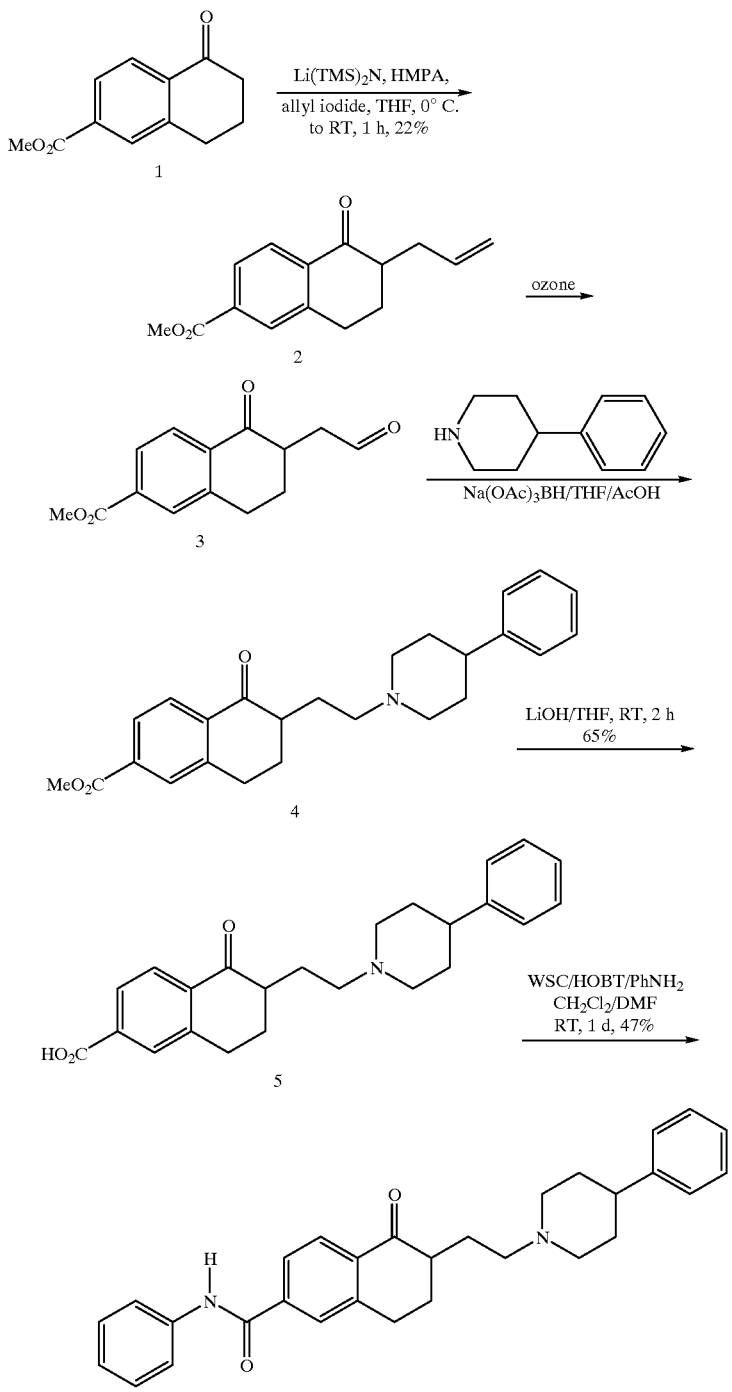

A. Compound 2:

Lithium bis(trimethylsilyl)amide (1 M in THF, 5.1 mL, 5.1 mmol) was added over 12 minutes to a solution of 1 (1.1 g, 5.4 mmol) in dry THF (22 mL) stirring at −78° C. under argon in a flame dried flask. HMPA (1.0 mL, 5.5 mmol) was added and then the −78° C. bath was replaced with a 0° C. bath. After 10 minutes, allyl iodide (2.0 mL, 22 mmol) was added quickly in one portion. After stirring at ambient temperature for 65 minutes, the reaction was quenched with water (22 mL). The reaction was transferred to a separatory funnel with ether/1 N HCl. Extraction with ether (2×150 mL), washing the combined organic layers with water, saturated NaHCO$_3$, water, and brine, and drying over MgSO$_4$ afforded 1.6 g of crude product. Flash chromatography (silica, 50 mm dia., 40% to 80% CH$_2$Cl$_2$/hexane) afforded 0.73 g (66%) of 5,6,7,8-tetrahydro-5-oxo-6-(2-propenyl)-2-naphthalenecarboxylic acid, methyl ester. R$_f$ (silica, 30% CH$_2$Cl$_2$/hexane)=0.12.

B. 5,6,7,8-Tetrahydro-5-oxo-6-(formylmethyl)-2-naphthalenecarboxylic acid, methyl ester Ozone generated by a Welsbach Ozonizer was bubbled into a solution of 2 (0.90 g, 4.0 mmol) in CH$_2$Cl$_2$ (60 mL) stirring at −78° C. until the blue color persisted (~10 minutes). Nitrogen was then bubbled through the reaction to discharge the blue color and then for 30 minutes after the blue color had dissipated. Hunig's base (1.4 mL, 8.0 mmol) was added dropwise over 5 minutes and the reaction was stirred at ambient temperature. After 1 hour, the reaction was transferred to a separatory funnel and washed with 0.5 M HCl (30 mL), H₂O (2×20 mL), and brine and dried over MgSO₄ to afford 1.0 g of crude product after evaporation of the solvent. Flash chromatography (silica, 37 mm dia, 50% EtOAc/hexane) afforded 0.60 g (66%) of the desired aldehyde.

C. 5,6,7,8-Tetrahydro-5-oxo-6-[2-(4-phenyl-1-piperidinyl)-ethyl]-2-naphthalenecarboxylic acid, methyl ester Sodium triacetoxyborohydride (0.86 g, 4.0 mmol) was added to a stirring solution of 4-phenylpiperidine (0.62 g, 3.9 mol), aldehyde 2 (0.60 g, 2.6 mmol), and acetic acid (0.15 mL, 2.6 mmol) in THF (23 mL). After stirring at ambient temperature for 1 day, the reaction was diluted with and transferred to a separatory funnel. Washing with ½ saturated NaHCO₃ and brine and drying over MgSO₄ afforded 1.4 g of crude product after evaporation of the solvent. Flash chromatography (silica, 37 mm dia, 5% MeOH/CH₂Cl₂) afforded 0.77 g (75%) of the title compound.

D. 5,6,7,8-Tetrahydro-5-oxo-6-[2-(4-phenyl-1-piperidinyl)-ethyl]-2-naphthalenecarboxylic acid Lithium hydroxide (1 M in H₂O, 1.2 mL, 1.2 mmol) was added to a solution of the title C compound (0.48 g, 1.2 mmol) in THF (12 mL). After stirring at ambient temperature for 2 hours, the reaction was evaporated in vacuo to afford 0.47 g of crude product. Chromatography (HP-20 rinsed with 200 mL H₂O, 25 mm dia., H₂O, 5% step gradient of 50 mL each from 0% to 50% acetone/H₂O) afforded 0.31 g (65%) of the title compound. mp 118.0–120.0° C.

Anal. for: $C_{24}H_{27}NO_3 \cdot 0.71 \, H_2O$:
Calc'd: C, 73.85; H, 7.34; N, 3.59.
Found: C, 73.85; H, 7.50; N, 3.72.

E. 5,6,7,8-Tetrahydro-5-oxo-N-phenyl-6-[2-(4-phenyl-1-piperidinyl)ethyl]-2-naphthalenecarboxamide 1-hydroxybenzotriazole hydrate (HOBT, 80 mg, 0.58 mmol) and 1-(3-dimethylamino-propyl)-3-ethylcarbodiimide hydrochloride (WSC, 0.17 g, 0.56 mmol) were added to a solution of title D compound (0.20 g, 0.53 mmol) in CH₂Cl₂ (2.5 mL) and DMF (0.64 mL) stirring at ambient temperature. After stirring for 30 minutes, aniline (65 mg, 0.70 mmol) in CH₂Cl₂ (0.3 mL) was added. After stirring at ambient temperature for 24 hours, water (20 mL) was added and the pH brought to 4.5 with 1 N HCl. Extraction with CH₂Cl₂ (2×20 mL), washing the combined organic layers with sat. NaHCO₃ and brine, and drying over MgSO₄ afforded 0.20 g of crude product after evaporation of the solvent. Flash chromatography (silica, 15 mm dia, 5% MeOH/CH₂Cl₂) afforded 0.14 g of product. Recrystallization from CH₂Cl₂/hexane afforded 0.11 g (47%) of the title compound. mp (° C.) 182.0–184.5.

Anal. for: $C_{30}H_{32}N_2O_2 \cdot 0.65 \, H_2O$:
Calc'd: C, 77.61; H, 7.23; N, 6.03.
Found: C, 77.61; H, 7.04; N, 6.25.

Using methodology analogous to that described for the title compound of Example 138, the compounds of Examples 139 to 144 were prepared:

Example 139

5,6,7,8-Tetrahydro-5-oxo-N-pentyl-6-[2-(4phenyl-1-piperidinyl)ethyl]-2-naphthalenecarboxamide

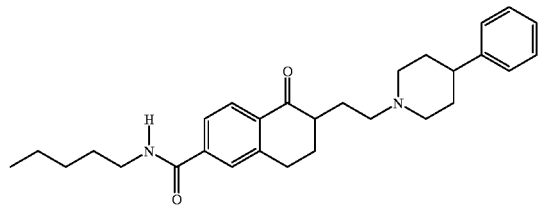

mp (° C.) 128.0–131.0.
Anal. for: $C_{29}H_{38}N_2O_2$:
Calc'd: C, 77.99; H, 8.58; N, 6.27.
Found: C, 78.16; H, 8.35; N, 6.44.

Example 140

1-[[5,6,7,8-Tetrahydro-5-oxo-6-[2-(4-phenyl-1-piperidinyl)ethyl]-2-naphthalenyl]carbonyl] piperidine

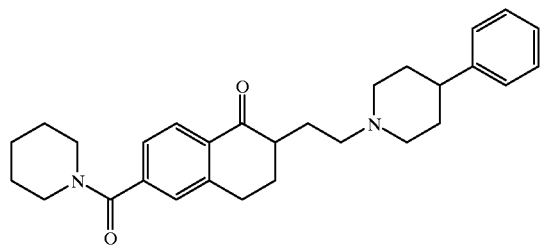

mp (° C.) 109.0–110.0.
Anal. for: $C_{29}H_{36}N_2O_2 \cdot 0.38 \, H_2O$:
Calc'd: C, 77.14; H, 8.21; N, 6.20.
Found: C, 77.12; H, 8.16; N, 6.47.

Example 141

5,6,7,8- Tetrahydro-N-(1H-imidazol-2-yl)ethyl]-5-oxo-6-[2-(4-phenyl-1-piperidinyl)ethyl]-2-naphthalenecarboxamide, Dihydrochloride

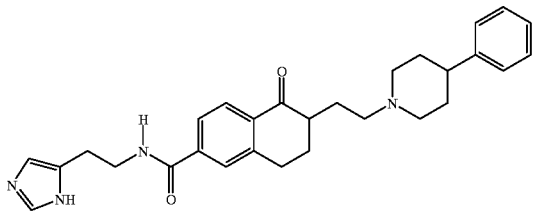

mp (° C.) 200.0–204.0.
Anal. for: $C_{29}H_{34}N_4O_2 \cdot 2 \, HCl \cdot 2.10 \, H_2O$:
Calc'd: C, 59.90; H, 6.97; N, 9.63.
Found: C, 59.93; H, 7.04; N, 9.46.

Example 142

2-[[[5,6,7,8-Tetrahydro-5-oxo-6-[2-(4-phenyl-1-piperidinyl)ethyl]-2-naphthalenyl]carbonyl]amino]acetic Acid, Ethyl Ester

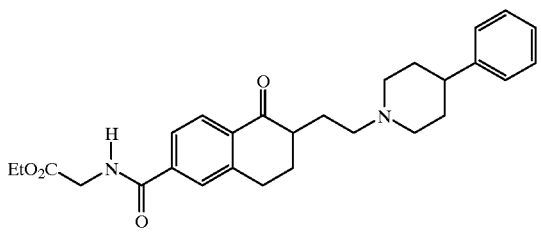

mp (° C.) 140.0–142.5.

Anal. for: $C_{28}H_{34}N_2O_4 \cdot 0.25\ H_2O$:

Calc'd: C, 72.01; H, 7.44; N, 6.00.

Found: C, 72.01; H, 7.31; N, 5.88.

Example 143

4-[[[5,6,7,8-Tetrahydro-5-oxo-6-[2-(4-phenyl-1-piperidinyl)ethyl]-2-naphthalenyl]carbonyl]amino]-1-piperidinecarboxylic Acid, Ethyl Ester

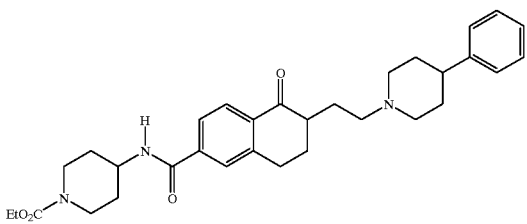

mp (° C.) 204.0–206.5.

Anal. for: $C_{32}H_{41}N_3O_4 \cdot 0.28\ H_2O$:

Calc'd: C, 71.62; H, 7.71; N, 7.75.

Found: C, 71.62; H, 7.80; N, 7.83.

Example 144

5,6,7,8-Tetrahydro-N-[3-(2-oxo-1-pyrrolidinyl)propyl]-5-oxo-6-[2-(4-phenyl-1-piperidinyl)ethyl]-2-naphthalenecarboxamide

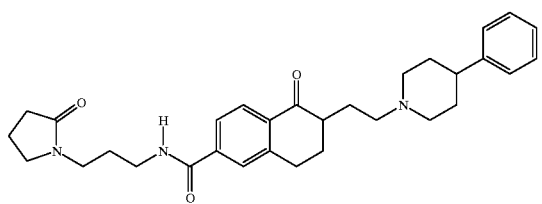

Anal. for: $C_{31}H_{39}N_3O_3 \cdot 0.15\ CH_2Cl_2 \cdot 1.12\ H_2O$:

Calc'd: C, 69.99; H, 7.94; N, 7.64.

Found: C, 69.99; H, 7.83; N, 7.86.

Example 145

N-([1,1-Biphenyl]2-yl)-5,6,7,8-tetrahydro-5-oxo-6-[2-(4-phenyl-1-piperidinyl)ethyl]-2-naphthalenecarboxamide, Monohydrochloride

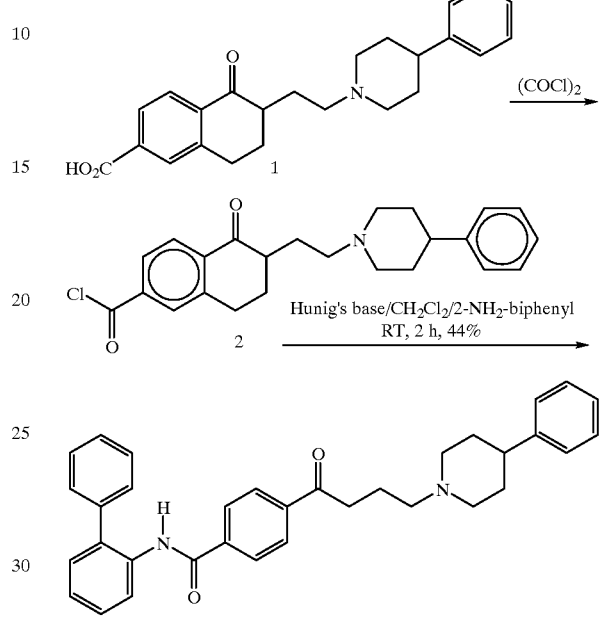

A. Compound 2

Oxalyl chloride (2 M in $CH_2Cl_2$, 0.10 mL, 0.20 mmol) was added to a solution of 1, the title compound of Example 138a, part D (60 mg, 0.16 mmol) in $CH_2Cl_2$ (1.0 mL) stirring in a flame dried flask under argon containing a catalytic amount of DMF. After stirring at ambient temperature for 30 minutes, the reaction was evaporated in vacuo to give 2.

B. (BMS 201761)

Compound 2 was dissolved in $CH_2Cl_2$ (1 mL) and diisopropylethyl amine (62 mg, 0.09 mL, 0.48 mmol) was added followed by 2-amino biphenyl (20 mg, 0.21 mmol). After stirring at ambient temperature for 2 hours, the reaction was transferred to a separatory funnel with water/$CH_2Cl_2$. Extraction with $CH_2Cl_2$ (2×20 mL) and drying over $MgSO_4$ afforded 0.24 g of crude product after evaporation of the solvent. Flash chromatography over silica gel (3% MeOH/$CH_2Cl_2$) afforded 37 mg (44%) of product. This material was combined with another batch and converted to its hydrochloride salt by addition of HCl (4 N in dioxane, 1 eq) to yield the title compound. mp 218.0–222.5° C.

Anal. for: $C_{36}H_{36}N_2O_2 \cdot HCl \cdot 0.32\ H_2O$:

Calc'd: C, 75.74; H, 6.65; N, 4.91.

Found: C, 75.74; H, 6.62; N, 4.82.

Using methodology analogous to that described for the title compound of Example 145, the compounds of Examples 146 to 189 were prepared:

Example 146

5,6,7,8-Tetrahydro-5-oxo-N-methyl-N-phenyl-6-[2-4-phenyl-1-piperidinyl)ethyl]-2-naphthalenecarboxamide

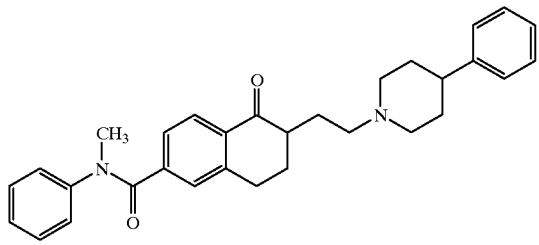

Example 147

5,6,7,8-Tetrahydro-N-(1-methylethyl)-5-oxo-6-[2-(4-phenyl-1-piperidinyl)ethyl]-2-naphthalenecarboxamide

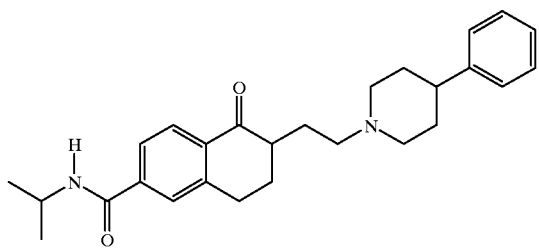

mp (° C.) 164.0–165.5.
Anal. for: $C_{27}H_{34}N_2O_2 \cdot 0.79\ H_2O$:
Calc'd: C, 74.93; H, 8.29; N, 6.47.
Found: C, 74.94; H, 8.06; N, 6.28.

Example 148

5,6,7,8-Tetrahydro-5-oxo-N-(phenylmethyl)-6-[2-(4-phenyl-1-piperidinyl)ethyl]-2-naphthalenecarboxamide

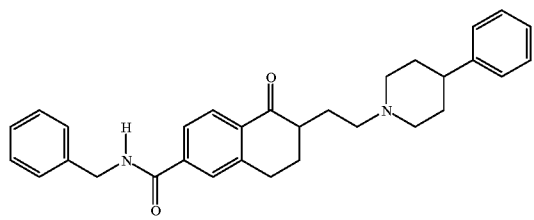

mp (° C.) 130.0–133.0.
Anal. for: $C_{31}H_{34}N_2O_2 \cdot 0.93\ H_2O$:
Calc'd: C, 77.03; H, 7.48; N, 5.80.
Found: C, 77.02; H,, 7.17; N, 5.72.

Example 149

N-[3,5-Bis(trifluoromethyl)phenyl]-5,6,7,8-tetrahydro-5-oxo-6-[2-(4-phenyl-1-piperidinyl)ethyl]-2-naphthalenecarboxamide, Monohydrochloride

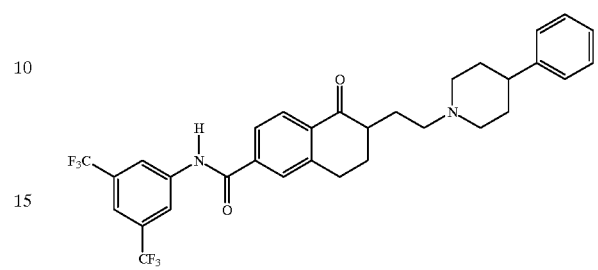

mp (° C.) 212.0–216.0.
Anal. for: $C_{32}H_{30}F_6N_2O_2 \cdot HCl$:
Calc'd: C, 61.49; H, 5.00; N, 4.48.
Found: C, 61.21; H, 4.93; N, 4.42.

Example 150

5,6,7,8-Tetrahydro-N-(3,3-dimethylbutyl)-5-oxo-6-[2(4-phenyl-1-piperidinyl)ethyl]-2-naphthalenecarboxamide, Monohydrochloride

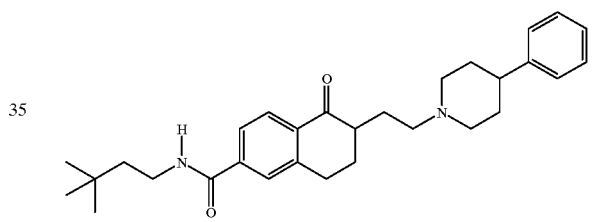

mp (° C.) 266.0–270.0.
Anal. for: $C_{30}H_{40}N_2O_2 \cdot HCl \cdot 0.26\ H_2O$:
Calc'd: C, 71.81; H, 8.22; N, 5.56; Cl, 6.84.
Found: C, 71.81; H, 8.34; N, 5.58, Cl, 7.07.

Example 151

4-[[[5,6,7,8-Tetrahydro-5-oxo-6-[2-(4-phenyl-1-piperidinyl)ethyl]-2-naphthalenyl]carbonyl]amino]benzoic Acid, Methyl Ester

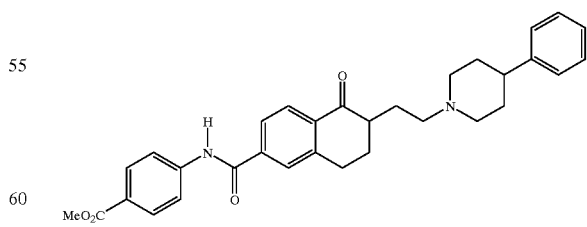

mp (° C.) 221.0–224.0.
Anal. for: $C_{32}H_{34}N_2O_4 \cdot 0.44\ H_2O$:
Calc'd: C, 74.13; H, 6.78; N, 5.40.
Found: C, 74.13; H, 6.50; N, 5.41.

Example 152

5,6,7,8-Tetrahydro-N-(2-methoxyphenyl)-5-oxo-6-[2-(4-phenyl-1-piperidinyl)ethyl]-2-naphthalenecarboxamide, Monohydrochloride

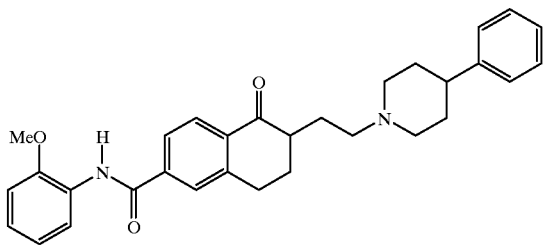

mp (° C.) 237.0–239.0.
Anal. for: $C_{31}H_{34}N_2O_3 \cdot HCl \cdot 0.63\ H_2O$:
Calc'd: C, 70.19; H, 6.89; N, 5.28; Cl, 6.68.
Found: C, 70.19; H, 6.58; N, 5.25; Cl, 6.68.

Example 153

5,6,7,8-Tetrahydro-N-(3-pyridinyl)-5-oxo-6-[2-(4-phenyl-1-piperidinyl)ethyl]-2-naphthalenecarboxamide, Monohydrochloride

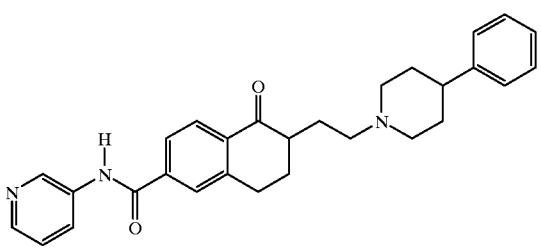

mp (° C.) 273.0–277.0.
Anal. for: $C_{29}H_{31}N_3O_2 \cdot HCl \cdot 0.95\ H_2O$:
Calc'd: C, 68.68; H, 6.74; N, 8.29; Cl, 6.94.
Found: C, 68.68; H, 6.42; N, 8.21; Cl, 7.14.

Example 154

5,6,7,8-Tetrahydro-N-(3,4-dimethyl-5-isoxazolyl)-5-oxo-6-[2-(4-phenyl-1-piperidinyl)ethyl]-2-naphthalenecarboxamide, Monohydrochloride

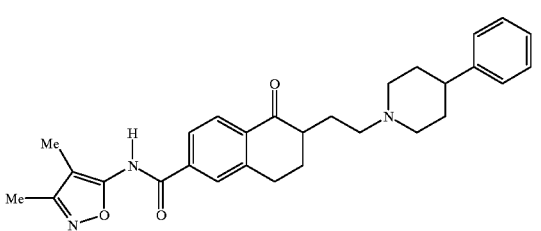

mp (° C.) 188.0–191.0.
Anal. for: $C_{29}H_{33}N_3O_3 \cdot HCl \cdot 0.44\ H_2O$:
Calc'd: C, 67.50; H, 6.81; N, 8.14; Cl, 6.87.
Found: C, 67.50; H, 6.44; N, 7.99; Cl, 6.87.

Example 155

5,6,7,8-Tetrahydro-N-[2-(1-methylethyl)phenyl]-5-oxo-6-[2-(4-phenyl-1-piperidinyl)ethyl]-2-naphthalenecarboxamide, (1:1.37) Hydrochloride

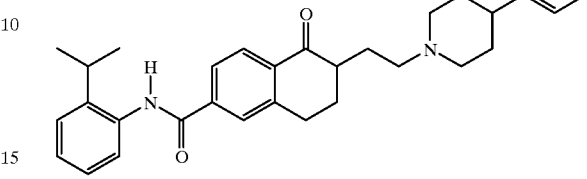

mp (° C.) 213.0–215.0.
Anal. for: $C_{33}H_{38}N_2O_2 \cdot 1.37\ HCl$:
Calc'd: C, 72.99; H, 7.28; N, 5.16; Cl, 8.94.
Found: C, 72.99; H, 7.34; N, 5.03; Cl, 9.31.

Example 156

N-(3-Chlorophenyl)-5,6,7,8-tetrahydro-5-oxo-6-[2-(4-phenyl-1-piperidinyl)ethyl]-2-naphthalenecarboxamide, (1:2.07) Hydrochloride

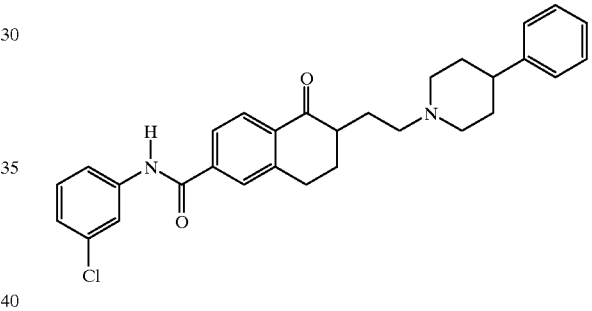

mp (° C.) 269.0–271.0.
Anal. for: $C_{30}H_{31}ClN_2O_2 \cdot 2.07\ HCl \cdot 0.36\ H_2O$
Calc'd: C, 63.32; H, 5.99; N, 4.92; Cl, 19.13.
Found: C, 63.32; H, 5.82; N, 4.81; Cl, 19.14.

Example 157

5,6,7,8-Tetrahydro-5-oxo-6-[2-(4-phenyl-1-piperidinyl)ethyl]-N-(4-pyridinyl)-2-naphthalenecarboxamide, Monohydrochloride

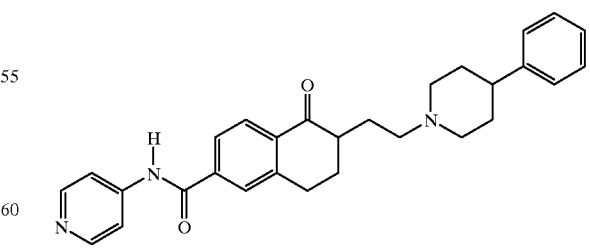

mp (° C.) 245.0–248.0.
Anal. for: $C_{29}H_{31}N_3O_2 \cdot 1.12\ HCl \cdot 0.61\ H_2O$:
Calc'd: C, 68.92; H, 6.65; N, 8.31; Cl, 7.86.
Found: C, 68.92; H, 6.38; N, 8.23; Cl, 7.84.

Example 158

5,6,7,8-Tetrahydro-5-oxo-6-[2-(4-phenyl-1-piperidinyl)ethyl]-2-naphthalenecarboxylic Acid, 1-phenylhydrazide, Dihydrochloride

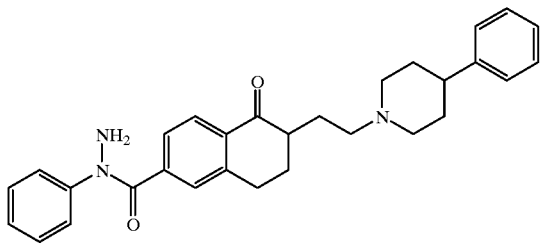

mp (° C.) 163.0–166.0.
Anal. for: $C_{30}H_{33}N_3O_2 \cdot 2.06$ HCl$\cdot 1.41$ $H_2O$
Calc'd: C, 63.42; H, 6.72; N, 7.40; Cl, 12.85.
Found: C, 63.42; H, 6.34; N, 7.37; Cl, 12.86.

Example 159

5,6,7,8-Tetrahydro-5-oxo-6-[2-(4-phenyl-1-piperidinyl)ethyl]-N-(4-pyridinyl)-2-naphthalenecarboxylic Acid, 2-phenylhydrazide, Hydrochloride

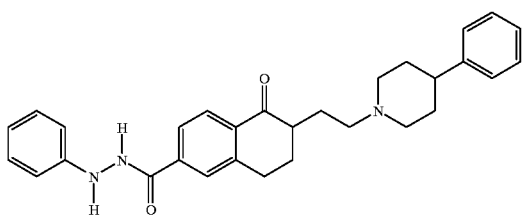

mp (° C.) 262.0–265.0.
Anal. for: $C_{30}H_{33}N_3O_2 \cdot 1.25$ HCl:
Calc'd: C, 70.21; H, 6.73; N, 8.19.
Found: C, 70.21; H, 6.36; N, 7.96.

Example 160

5,6,7,8-Tetrahydro-5-oxo-6-[2-(4-phenyl-1-piperidinyl)ethyl]-2-naphthalenecarboxamide

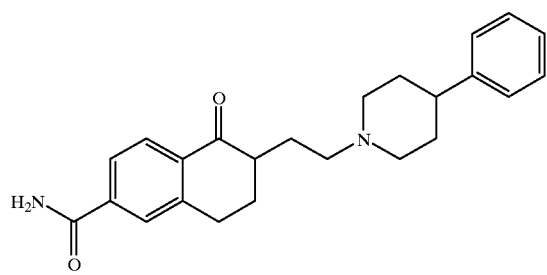

mp (° C.) 216.0–218.0.
Anal. for: $C_{24}H_{28}N_2O_2$:
Calc'd: C, 76.56; H, 7.50; N, 7.44.
Found: C, 76.29; H, 7.47; N, 7.33

Example 161

5,6,7,8-Tetrahydro-N-methoxy-N-methyl-5-oxo-[2-(4-phenyl-1-piperidinyl)ethyl]-2-naphthalenecarboxamide

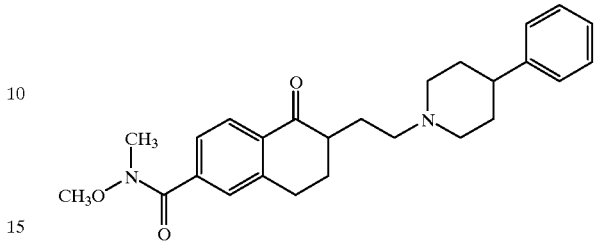

mp (° C.) 82.5–85.0.
Anal. for: $C_{26}H_{32}N_2O_3 \cdot 0.12$ $CH_2Cl_2$:
Calc'd: C, 72.82; H, 7.55; N, 6.50.
Found: C, 72.82; H, 7.43; N, 6.58.

Example 162

N-([1,1-Biphenyl]-3-yl)-5,6,7,8-tetrahydro-5-oxo-6-[2-(4-phenyl-1-piperidinyl)ethyl]-2-naphthalenecarboxamide

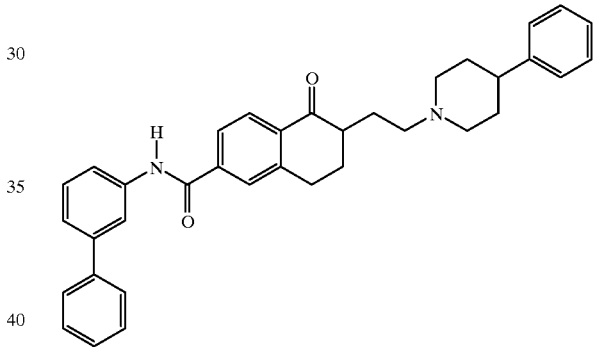

mp (° C.) 208.0–211.0.
Anal. for: $C_{36}H_{36}N_2O_2 \cdot 1.23$ $H_2O$:
Calc'd: C, 78.50; H, 7.04; N, 5.09.
Found: C, 78.39; H, 6.70; N, 5.49.

Example 163

5,6,7,8-Tetrahydro-5-oxo-6-[2-(4-phenyl-1-piperidinyl)ethyl]-N-(1H-pyrrol-1-yl)-2-naphthalenecarboxamide, Monohydrochloride

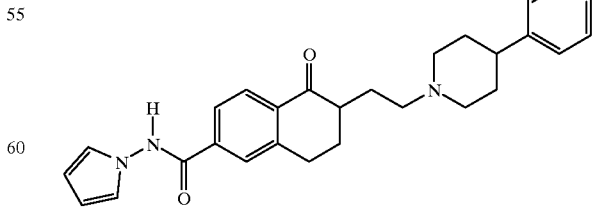

mp (° C.) 284.0–288.0.

Anal. for: $C_{28}H_{31}N_3O_2 \cdot HCl \cdot 0.53$ $H_2O$:
Calc'd: C, 68.97; H, 6.83; N, 8.65.

Example 164

5,6,7,8-Tetrahydro-5-oxo-N-(2-phenylethyl)-6-[2-(4-phenyl-1-piperidinyl)ethyl]-2-naphthalenecarboxamide

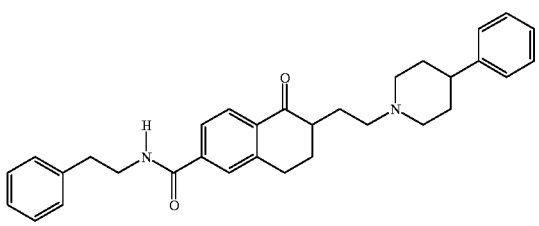

mp (° C.) 149.0–150.0.
Anal. for: $C_{32}H_{36}N_2O_2 \cdot 1.50\ H_2O$:
Calc'd: C, 75.70; H, 7.74; N, 5.52.
Found: C, 75.40; H, 7.34; N, 5.78.

Example 165

5,6,7,8-Tetrahydro-5-oxo-N-(2-phenoxyphenyl)-6-[2-(4-phenyl-1-piperidinyl)ethyl]-2-naphthalenecarboxamide, Monohydrochloride

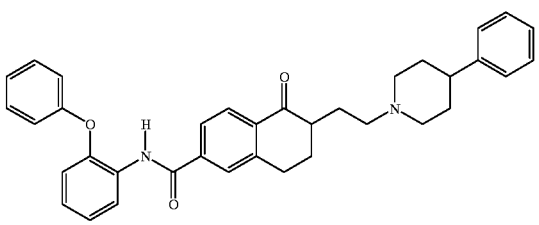

mp (° C.) 234.0–236.5.
Anal. for: $C_{36}H_{36}N_2O_3 \cdot HCl$:
Calc'd: C, 74.40; H, 6.42; N, 4.82; Cl, 6.10.
Found: C, 74.18; H, 6.29; N, 4.73; Cl, 5.74.

Example 166

N-(3,5-Dimethoxyhenyl)-5,6,7,8-tetrahydro-5-oxo-[2-(4-phenyl-1-piperidinyl)ethyl]-2-naphthalenecarboxamide, Monohydrochloride

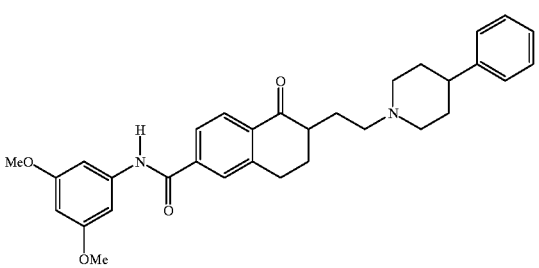

mp (° C.) 281.0–284.0.
Anal. for: $C_{32}H_{36}N_2O_4 \cdot HCl \cdot 1.06\ H_2O$:
Calc'd: C, 67.64; H, 6.94; N, 4.93.
Found: C, 67.64; H, 6.60; N, 4.83.

Example 167

N-(3,5-Bis(trifluoromethyl)phenyl]methyl]-5,6,7,8-tetrahydro-5-oxo-6-[2-(4-phenyl-1-piperidinyl)ethyl]-2-naphthalene-carboxamide, Monohydrochloride

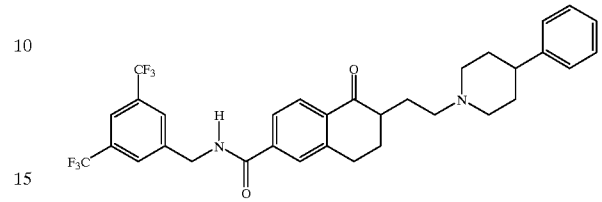

mp (° C.) 275.0–278.0.
Anal. for: $C_{33}H_{32}F_6N_2O_2 \cdot HCl \cdot 0.55\ H_2O$:
Calc'd: C, 61.08; H, 5.30; N, 4.32; F, 17.57; Cl, 5.46.
Found: C, 61.08; H, 5.06; N, 4.36; F, 17.44; Cl, 5.69.

Example 168

N-(1,1-Biphenyl]-2-ylmethyl)-5,6,7,8-tetrahydro-5-oxo-6-[2-(4-phenyl-1-piperidinyl)ethyl]-2-naphthalenecarboxamide, (1:1.07) Hydrochloride

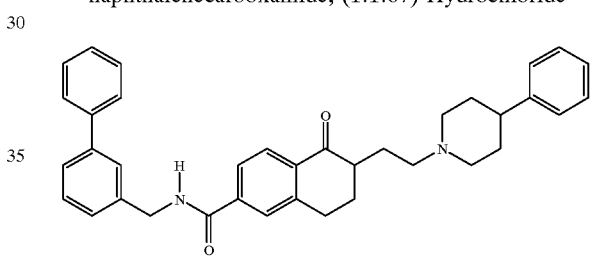

mp (° C.) 236.0–238.0.
Anal. for: $C_{37}H_{38}N_2O_2 \cdot 1.07\ HCl \cdot 0.16\ H_2O$:
Calc'd: C, 76.01; H, 6.79; N, 4.79; Cl, 6.49.
Found: C, 76.01; H, 6.72; N, 4.72; Cl, 6.50.

Example 169

5,6,7,8-Tetrahydro-5-oxo-6-[2-(4-phenyl-1-piperidinyl)ethyl]-N-(3-phenylpropyl)-2-naphthalenecarboxamide

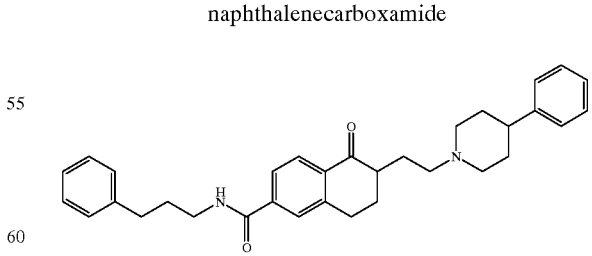

mp (° C.). 114.0–118.0.
Anal. for: for $C_{38}H_{38}N_2O_2 \cdot 0.72\ H_2O$:
Calc'd: C, 78.02; H, 7.83; N, 5.51.
Found: C, 78.02; H, 7.67; N, 5.63.

(Found: C, 68.97; H, 6.51; N, 8.65.)

Example 170

5,6,7,8-Tetrahydro-5-oxo-6-[2-(4phenyl-1-piperidinyl)ethyl]-N-(4-phenylbutyl)-2-naphthalenecarboxamide

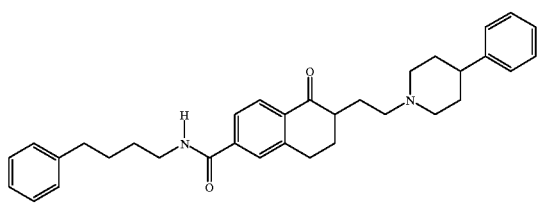

mp (° C.) 139.0–140.5.
Anal. for: $C_{34}H_{40}N_2O_2 \cdot 0.76\ H_2O$.
Calc'd: C, 78.17; H, 8.01; N, 5.36.
Found: C, 78.17; H, 7.74; N, 5.46.

Example 171

N-[2-Cyclohexen-1-yl)ethyl]-5,6,7,8-tetrahydro-5-oxo-6-[2-(4-phenyl-1-piperidinyl)ethyl]-2-naphthalenecarboxamide

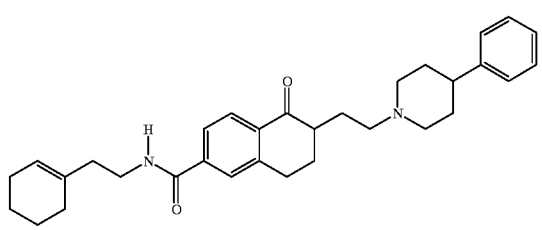

mp (° C.). 144.0–146.0.
Anal. for: $C_{32}H_{40}N_2O_2 \cdot 0.41\ H_2O$:
Calc'd: C, 78.10; H, 8.36; N, 5.69.
Found: C, 78.10; H, 8.20; N, 5.71.

Example 172

N-[2-(3,4-Dimethoxyphenyl)ethyl]-5,6,7,8-tetrahydro-5-oxo-6-[2-(4-phenyl-1-piperidinyl)ethyl]-2-naphthalenecarboxamide

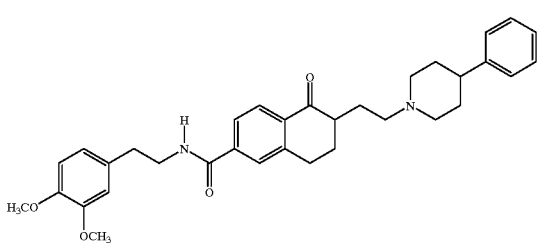

mp (° C.) 159.5–162.0.
Anal. for: $C_{34}H_{40}N_2O_4 \cdot 0.90\ H_2O$:
Calc'd: C, 73.33; H, 7.57; N, 5.03.
Found: C, 73.33; H, 7.32; N, 5.04.

Example 173

N-[2,2-Diphenylethyl)-5,6,7,8-tetrahydro-5-oxo-6-[2-(4-phenyl-1-piperidinyl)ethyl]-2-naphthalenecarboxamide

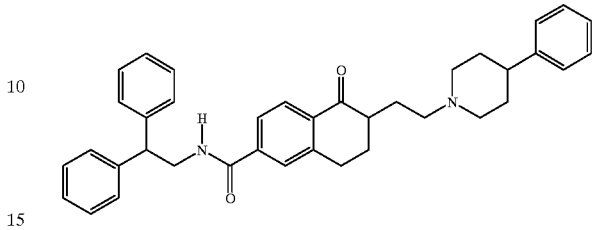

mp (° C.) 158.0–161.0.
Anal. for: $C_{38}H_{40}N_2O_2 \cdot 0.67\ H_2O$:
Calc'd: C, 80.24; H, 7.33; N, 4.92.
Found: C, 80.24; H, 7.05; N, 4.87.

Example 174

N-[2,3-Dihydro-1H-inden-2-yl)-5,6,7,8-tetrahydro-5-oxo-6-[2-(4-phenyl-1-piperidinyl)ethyl]-2-naphthalenecarboxamide

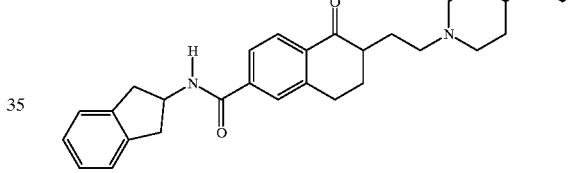

mp (° C.) 205.0–208.0.
Anal. for: $C_{33}H_{36}N_2O_2 \cdot 0.74\ H_2O$:
Calc'd: C, 78.34; H, 7.47; N, 5.54.
Found: C, 78.34; H, 7.21; N, 5.52.

Example 175

5,6,7,8-Tetrahydro-N-[2-(1-naphthalenyl)ethyl]-5-oxo-6-[2-(4-phenyl-1-piperidinyl)ethyl]-2-naphthalenecarboxamide, Hydrochloride

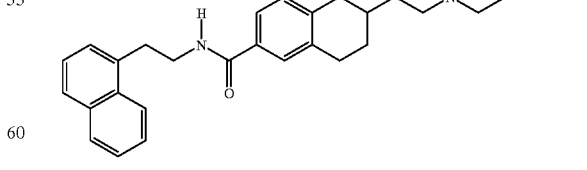

mp (° C.) 45.0–50.0.
Anal. for: $C_{36}H_{38}N_2O_2 \cdot 0.88\ Hcl$:
Calc'd: C, 76.82; H, 6.96; N, 4.98.
Found: C, 76.82; H, 6.99; N, 4.82.

Example 176

5,6,7,8-Tetrahydro-N-[2-(2-naphthalenyl)ethyl]-5-oxo-6-[2-(4-phenyl-1-piperidinyl)ethyl]-2-naphthalenecarboxamide

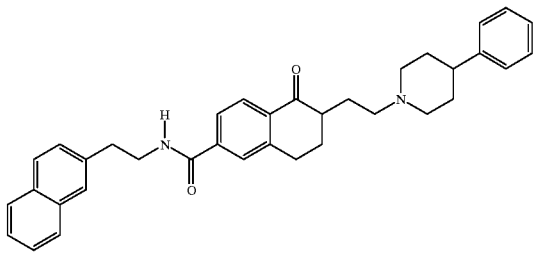

mp (° C.) 176.0–178.0.
Anal. for: $C_{36}H_{38}N_2O_2 \cdot 0.34\ H_2O$:
Calc'd: C, 80.54; H, 7.26; N, 5.22.
Found: C, 80.54; H, 7.12; N, 5.26.

Example 177

N-[(2,2-Dimethylcyclopentyl)methyl]-5,6,7,8-tetrahydro-5-oxo-6-[2-(4-phenyl-1-piperidinyl)ethyl]-2-naphthalenecarboxamide

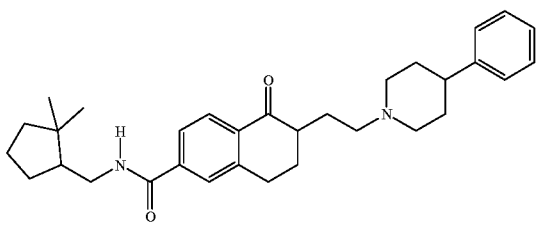

Anal. for: $C_{32}H_{42}N_2O_2 \cdot 0.96\ H_2O$:
Calc'd: C, 76.25; H, 8.78; N, 5.56.
Found: C, 76.25; H, 8.26; N, 5.29.
oil

Example 178 trans-5,6,7,8-Tetrahydro-5-oxo-N-(2-phenylcyclopropyl)-6-[2-(4-phenyl-1-piperidinyl)ethyl]-2-naphthalenecarboxamide

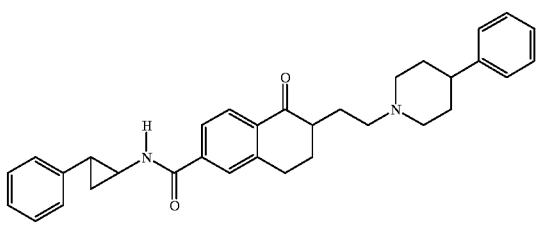

mp (° C.) 72.0–78.0.
Anal. for: $C_{33}H_{36}N_2O_2 \cdot 0.44\ H_2O$:
Calc'd: C, 79.17; H, 7.43; N, 5.60.
Found: C, 79.17; H, 7.20; N, 5.49.

Example 179

5,6,7,8-Tetrahydro-N-(1-naphthalenylmethyl)-5-oxo-6-[2-(4-phenyl-1-piperidinyl)ethyl]-2-naphthalenecarboxamide

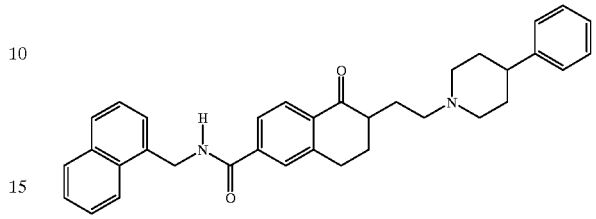

mp (° C.) 88.0–92.0.

Anal. for: $C_{35}H_{36}N_2O_2 \cdot 0.39\ H_2O$:

Calc'd: C, 80.26; H, 7.08; N, 5.35.

Found: C, 80.26; H, 6.75; N, 5.14.

Example 180

5,6,7,8-Tetrahydro-5-oxo-6-[2-(4-phenyl-1-piperidinyl)ethyl]-N-[(S)-2-phenylcyclopropyl]-2-naphthalenecarboxamide

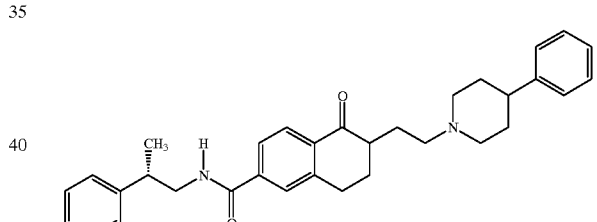

Example 181

5,6,7,8-Tetrahydro-5-oxo-6-[2-(4-phenyl-1-piperidinyl)ethyl]-N-[(R)-2-phenylcyclopropyl]-2-naphthalenecarboxamide

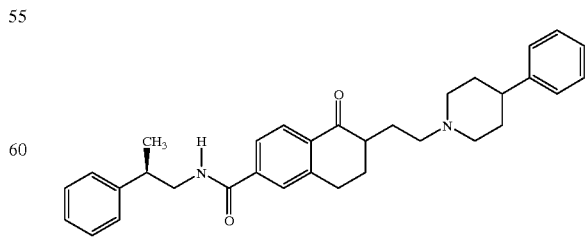

495 M+1.

Example 182

5,6,7,8-Tetrahydro-N-[(R)-1-(hydroxymethyl)-3-methylbutyl]-5-oxo-6-[2-(4-phenyl-1-piperidinyl)ethyl]-2-naphthalenecarboxamide

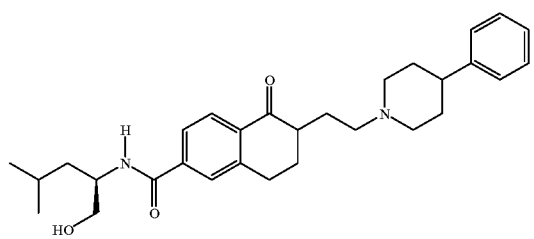

477 M+1.

Example 183

5,6,7,8-Tetrahydro-N-[(S)-1-(hydroxymethyl)-3-methylbutyl])-5-oxo-6-[2-(4-phenyl-1-piperidinyl)ethyl]-2-naphthalene-carboxamide

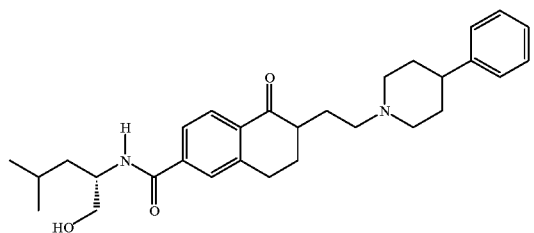

477 M+1.

Example 184

5,6,7,8-Tetrahydro-5-oxo-6-[2-(4phenyl-1-piperidinyl)ethyl]-N-[2(2-thienyl)ethyl]-2-naphthalenecarboxamide

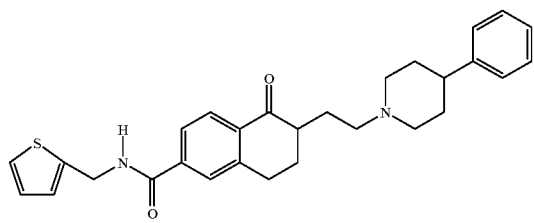

487 M+1.

Example 185

N-[(1-(4-Chlorophenyl)cyclopropyl]methyl]-5,6,7,8-tetrahydro-5-oxo-6-[2-(4-phenyl-1-piperidinyl)ethyl]-2-naphthalene-carboxamide

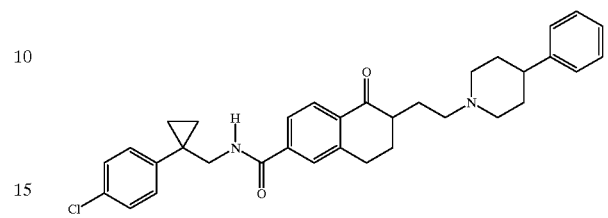

541 M+1.

Example 186

N-[2-(4-Dibenzofuranyl)ethyl]-5,6,7,8-tetrahydro-5-oxo-6-[2-(4-phenyl-1-piperidinyl)ethyl]-2-naphthalenecarboxamide

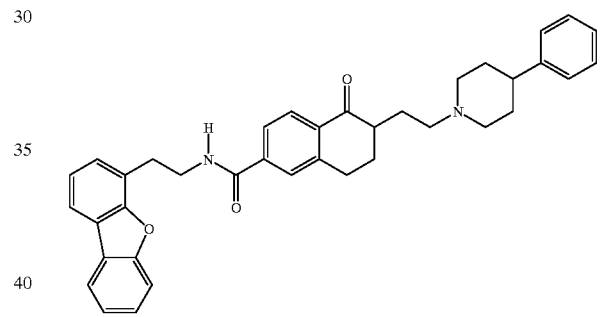

571 M+1.

Example 187

5,6,7,8-Tetrahydro-N-(3-hydroxy-2,3-diphenylpropyl)-5-oxo-6-[2-(4-phenyl-1-piperidinyl)ethyl]-2-naphthalenecarboxamide

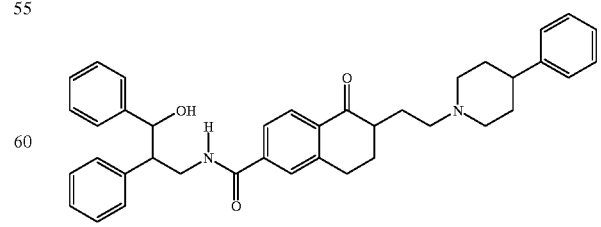

587 M+1.

Example 188 cis-5,6,7,8-Tetrahydro-5-oxo-N-(2-phenylcyclopropyl)-6-[2-(4-phenyl-1-piperidinyl)ethyl]-2-naphthalenecarboxamide

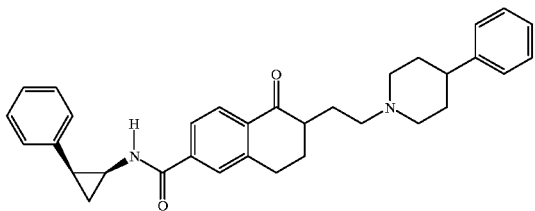

493 M+1.

Example 189

5,6,7,8-Tetrahydro-5-oxo-N-(2,2,3,3,3-pentafluoropropyl)-6-[2-(4-phenyl-1-piperidinyl)ethyl]-2-naphthalenecarboxamide

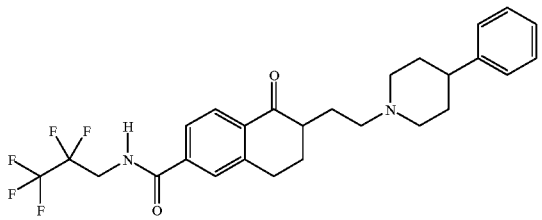

509 M+1.

Example 190

5,6,7,8-Tetrahydro-N-(2-methylbutyl)-5-oxo-6-[2-(4-phenyl-1-piperidinyl)ethyl]-2-naphthalenecarboxamide, Trifluoroacetate

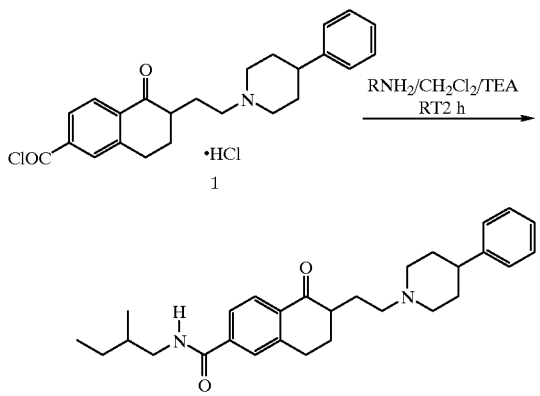

A solution of 1 (48 mg, 0.11 mmol), see Example 145 for reparation and triethylamine (0.018 mL, 0.13 mmol in CH$_2$Cl$_2$ (1 mL) was added to (2-methylbutyl)amine (0.07 mol). After shaking for 2 hours, the reaction was diluted with 5% MeOH/CH$_2$Cl$_2$ (1 mL) and the mixture was loaded onto a SAX column (6 g, pretreated with 20 mL 1N NaOAc, 40 mL H$_2$O, 20 mL MeOH, 20 mL CH$_2$Cl$_2$ and 10 mL 5% MeOH/CH$_2$Cl$_2$). The column was then eluted with 3 mL of 5% MeOH/CH$_2$Cl$_2$. The total effluent was collected and evaporated. The product was dissolved in 2 to 4 mL of 80% MeOH/H$_2$O and then added in 2 mL portions to a preparative HPLC (YMS S5 ODS, 30×250 mm C-18, 25 mL/minute, 50% to 90% MeOH/H$_2$O with 0.1% TFA linear gradient over 20 minutes, 5-minutes hold at 90%, detection at 217 nm). Fractions which were pure were combined and evaporated.

M+1: 447.

Using methodology analogous to that described for the title compound of Example 190, the compounds of Examples 190a to 201 were prepared:

Example 190a 5,6,7,8-Tetrahydro-N-(3-methylbutyl)-5-oxo-6-[2-(4-phenyl-1-piperidinyl)ethyl]-2-naphthalenecarboxamide, Trifluoroacetate

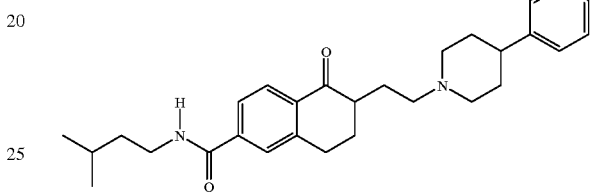

Yield 56%.
MS (ESI) 447.

Example 191

5,6,7,8-Tetrahydro-N-(1-methylbutyl)-5-oxo-6-[2-(4-phenyl-1-piperidinyl)ethyl]-2-naphthalenecarboxamide, Trifluoroacetate

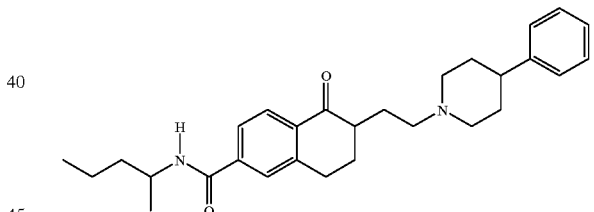

Yield 45%.
MS (ESI) 447.

Example 192

5,6,7,8-Tetrahydro-5-oxo-6-[2-(4-phenyl-1-piperidinyl)ethyl]-N-[(tetrahydro-2-furanyl)methyl]-2-naphthalenecarboxamide, Trifluoroacetate

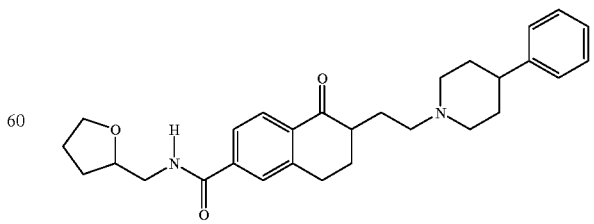

Yield 73%.
MS (ESI) 461.

Example 193

5,6,7,8-Tetrahydro-5-oxo-6-[2-(4-phenyl-1-piperidinyl)ethyl]-N-(2-phenylpropyl)-2-naphthalenecarboxamide, Trifluoroacetate

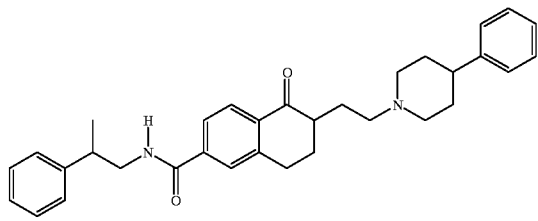

Yield 43%.

MS (ESI) 495.

Example 194

5,6,7,8-Tetrahydro-N-(2-hydroxy-2-phenylethyl)-5-oxo-6-[2-(4-phenyl-1-piperidinyl)ethyl]-2-naphthalenecarboxamide, Trifluoroacetate

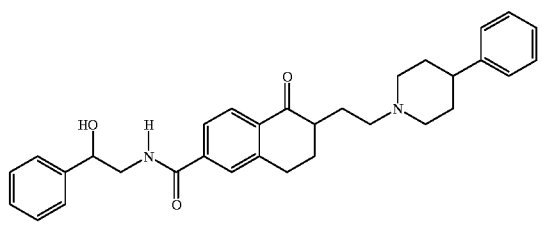

Yield 55%.

MS (ESI) 497.

Example 195

N-[2-(2-Fluorophenyl)ethyl]-5,6,7,8-tetrahydro-5-oxo-6-[2-(4-phenyl-1-piperidinyl)ethyl]-2-naphthalenecarboxamide, Trifluoroacetate

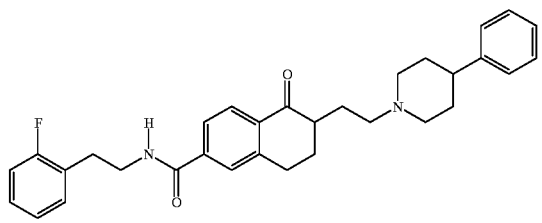

Yield 46%.

MS (ESI) 499.

Example 196

N-[2-(4-Fluorophenyl)ethyl]-5,6,7,8-tetrahydro-5-oxo-6-[2-(4-phenyl-1-piperidinyl)ethyl]-6-naphthalenecarboxamide, Trifluoroacetate

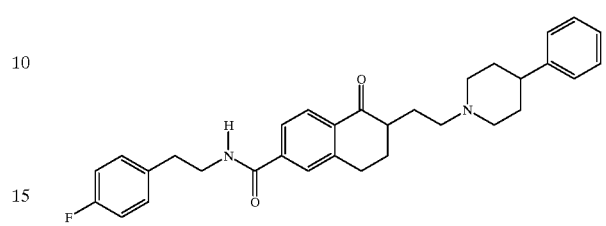

Yield 42%.

MS (ESI) 499.

Example 197

N-[2-(3-Fluorophenyl)ethyl]-5,6,7,8-tetrahydro-5-oxo-6-[2-(4-phenyl-1-piperidinyl)ethyl]-2-naphthalenecarboxamide, Trifluoroacetate

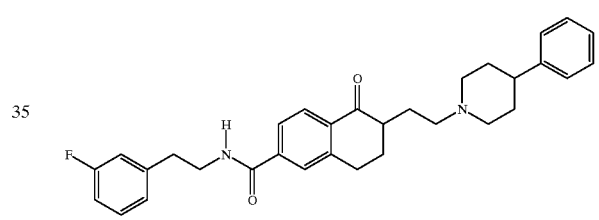

Yield 54%.

MS (ESI) 499.

Example 198

N-[2-(4-Chlorophenyl)ethyl]-5,6,7,8-tetrahydro-5-oxo-6-[2-(4-phenyl-1-piperidinyl)ethyl]-2-naphthalenecarboxamide

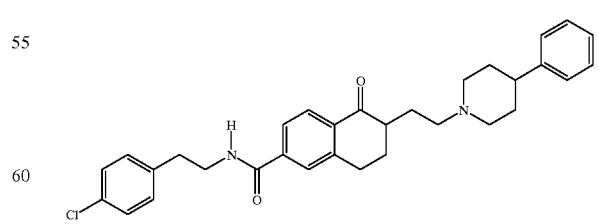

Yield 51%.

MS (ESI) 516.

Example 199

5,6,7,8-Tetrahydro-N-[2-(1H-indol-3-yl)ethyl]-5-oxo6-[2-(4-phenyl-1-piperidinyl)ethyl]-2-naphthalenecarboxamide

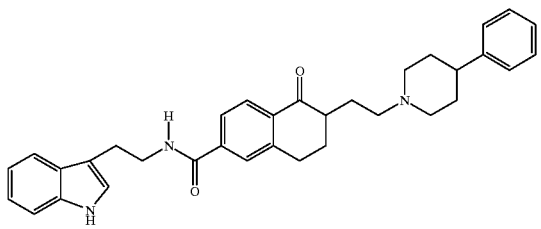

Yield 37%.
MS (ESI) 520.

Example 200

N-(3,3-Diphenylpropyl)-5,6,7,8-tetrahydro-5-oxo-6-[2-(4-phenyl-1-piperidinyl)ethyl]-2-naphthalenecarboxamide

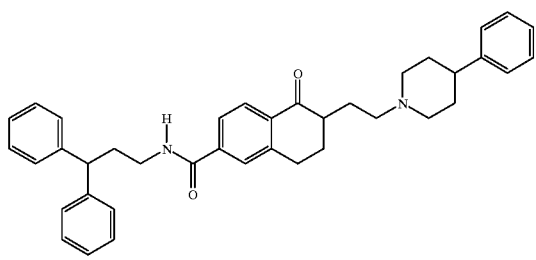

Yield 41%.
MS (ESI) 571.

Example 201

5,6,7,8-Tetrahydro-5-oxo-N-[2-(4-phenoxyphenyl)ethyl]-6-[2-(4-phenyl-1-piperidinyl)ethyl]-2-naphthalenecarboxamide

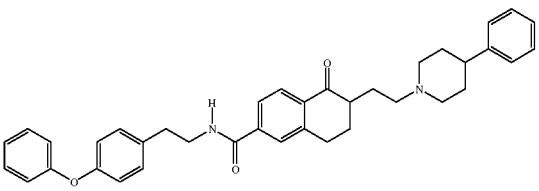

Yield 28%.

MS (ESI) 573.

Example 202

3,4-Dihydro-6-methoxy-2-[3-(4-phenyl-1-piperidinyl)propyl]-1(2H)-naphthalenone, Monohydrochloride

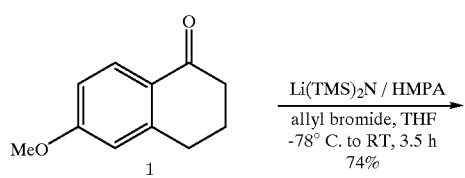

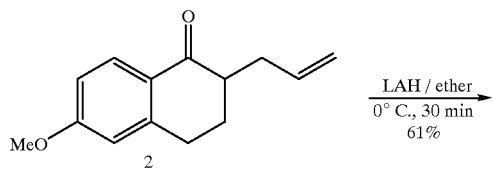

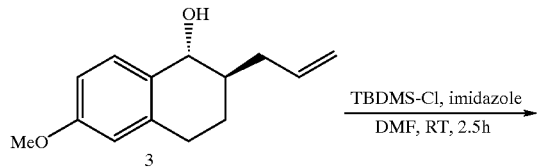

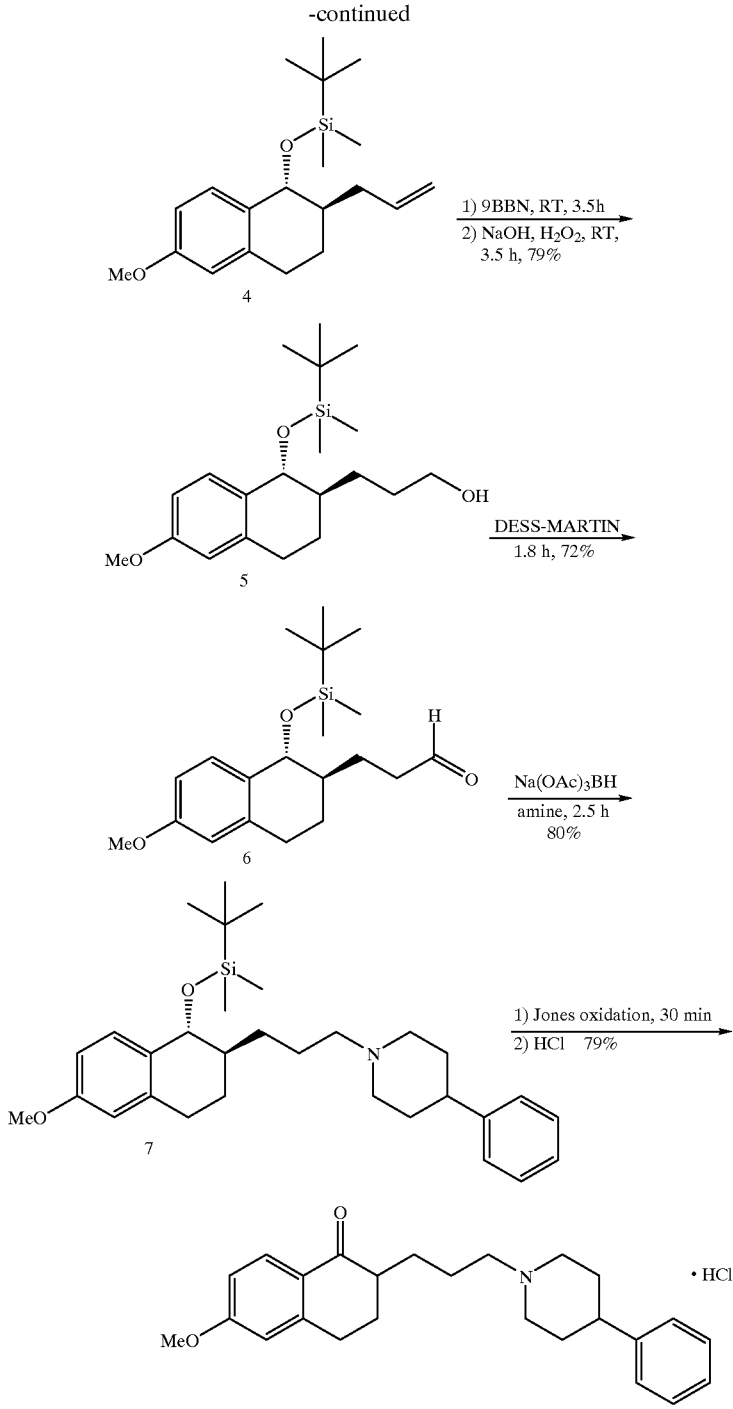

A. 3,4-Dihydro-6-methoxy-2-(1prop-2-enyl)-1(2H)-naphthalenone

A solution of 6-methoxy-1-tetralone (0.88 g, 5.0 mmol) in THF (25 mL) was stirred in an oven-dried flask at −78° C. under argon. Lithium hexamethyldisilamide (1 M in THF, 5.2 mL, 5.2 mmol) was slowly added over 10 minutes. After stirring at −78° C. for 15 minutes, HMPA (1.8 g, 1.7 mL, 10 mmol) was added. After stirring an additional 5 minutes at −78° C., allyl bromide (0.60 g, 0.43 mL, 5.0 mmol) in THF (5 mL) was added slowly over 10 minutes. The cold bath was then removed and the reaction allowed to slowly warm to room temperature over 3.5 hours. The reaction was quenched by adding 1 N HCl and transferred to a separatory funnel with $CH_2Cl_2$ and 1 N HCl. Extraction with $CH_2Cl_2$ (2×100 mL), washing the combined organic layers with water, and drying over $MgSO_4$ afforded 2.2 g of crude product after evaporation of the solvent. Flash chromatography (silica, 50 mm dia, 15% EtOAc/hexane) afforded 0.80 g (74%) of the title compound: $R_f$ (silica, 40% EtOAc/hexane)=0.55.

B. trans-1,2,3,4-Tetrahydro-6-methoxy-2-(1-prop-2-enyl)-1-naphthalenol

Lithium aluminum hydride (1 M in ether, 8.3 mL, 8.3 mmol) was added to ether (8.3 mL) stirring a 0° C. under argon in a flame dried flask. A solution of the title A compound (3.4 g, 16 mmol) in ether (5 mL) was added over 5 minutes. After stirring at 0° C. for 30 minutes, the reaction was quenched with saturated NH₄Cl and transferred to a separatory funnel with water/ether. Extraction with ether (2×250 mL), washing the combined organic layers with brine, and drying over MgSO₄ afforded 3.9 g of crude product. Flash chromatography (silica gel, 10% EtOAc/hexane) afforded 1.92 g of the title compound: mp 63.0–65.0° C.; R$_f$ (silica gel, 25% EtOAc/hexane)=0.25.

C. Compound 4 t-butyldimethylsilyl chloride (3.1 g, 20 mmol) was added to a solution of title B compound (0.90 g, 4.1 mmol) and imidazole (2.8 g, 41 mmol) in DMF (3.3 mL) stirring under argon. After stirring at ambient temperature for 2.5 hours, the reaction solution was transferred to a separatory funnel with water/ether (pH of the aqueous layer was 8). Extraction with ether (2×70 mL), washing the combined organic layers with water and brine, and drying over MgSO₄ afforded 3.5 g of crude product after evaporation of the solvent. Flash chromatography (silica gel, 5% EtOAc/hexane) afforded 1.7 g (>100%) of compound 4.

D. Compound 5

A solution of the title C compound (1.8 g, 4.6 mmol) in THF (4.5 mL) was added to 9-BBN (0.5 M in THF, 13 mL, 6.4 mmol) stirring in a flame dried flask under argon. After stirring at ambient temperature for 3.5 hours, the reaction was quenched with water (0.45 mL). 2N NaOH (4.5 mL) and then hydrogen peroxide (30% solution, 2.3 mL) were added. After stirring for 3.5 hours, the reaction was quenched with saturated NaHCO₃ solution and transferred to a separatory funnel with water/CH₂Cl₂. Extraction with CH₂Cl₂ (3×30 mL) and drying over MgSO₄ afforded 2.0 g of crude product. Flash chromatography (silica gel, 20% EtOAc/hexane) afforded 1.3 g (79%) of the title compound.

E. Compound 6

Dess-Martin reagent (1,1,1-triacetoxy-1,1-dihydro-1,2-benziodoxol-3(1H)-one, 3.0 g, 4.8 mmol) was added to a solution of the title D compound 3 (1.1 g, 3.2 mmol) in CH₂Cl₂ (20 mL) stirring under argon at ambient temperature in a flame-dried flask. After stirring at ambient temperature for 1.8 hours, ether was added and the reaction evaporated in vacuo. The residue was transferred to a separatory funnel with ether (200 mL) and 1/1 10% Na₂S₂O₃/saturated NaHCO₃ (150 mL). Extraction with ether and washing with water (50 mL) and brine (50 mL) and drying over MgSO₄ afforded 1.1 g of crude product. Flash chromatography (silica gel, 10% EtOAc/hexane) afforded 0.80 g (72%) yield of compound 6: R$_f$ (silica, 15% EtOAc/hexane)=0.45.

F. Compound 7

Sodium triacetoxyborohydride (0.68 g, 3.2 mmol) was added to a solution of 4-phenylpiperidine (0.45 g, 2.8 mmol), aldehyde 6 (0.80 g, 2.3 mmol), and acetic acid (0.12 mL, 2.3 mmol) in THF (23 mL) stirring at ambient temperature under argon. After stirring for 2.5 hours, the solvent was removed in vacuo. The residue was transferred to a separatory funnel with EtOAc/saturated NaHCO₃. Extraction with EtOAc (2×80 mL), washing the combined organic layers with brine, and drying over MgSO₄ afforded 1.1 g of crude product after evaporation of the solvent. Flash chromatography (silica gel, 50% EtOAc/CH₂Cl₂) afforded 0.91 g (80%) of compound 7.

G. 3,4-Dihydro-6-methoxy-2-[(4-phenyl-1-piperidinyl)propyl]-1-(2H)-naphthalenone, Monohydrochloride Jones reagent (1.25 M, 8.2 mL, 10.5 mmol) was added in 2 mL fractions over 1 hour to a solution of title F compound (0.91 g, 1.8 mmol) in acetone (40 mL) stirring at 0° C. The cold bath was then removed and the solution stirred at ambient temperature. After stirring for 30 minutes, the reaction was quenched with isopropanol (13 mL) and evaporated in vacuo. The residue was transferred to a separatory funnel with CH₂Cl₂ and 2N NaOH. Extraction with CH₂Cl₂ (2×100 mL) and drying over MgSO₄ afforded 1.4 g of crude product after evaporation of the solvent. Flash chromatography (silica, 5% MeOH/CH₂Cl₂) afforded 0.55 g (79%) of the desired product. This material was dissolved in CH₂Cl₂ (10 mL) and 4N HCl in dioxane (0.36 mL, 1.5 mmol) was added. After evaporating the solvent, the resulting solid was triturated with EtOAc and the solid collected to afford 0.61 g of the title compound: mp 209.0–212.0° C.

Anal. for: C$_{25}$H$_{31}$NO$_2$.HCl.0.09 CH$_2$Cl$_2$.0.30 H$_2$O:

Calc'd: C, 70.56; H, 7.74; N, 3.28; Cl, 9.81.

Found: C, 70.59; H, 7.69; N, 3.16; Cl, 9.82.

EXAMPLE 203

(E)-3,4-Dihydro-6-methoxy-2-[(4-phenyl-1-piperidinyl)propyl]-1-(2H)-naphthalenone, Oxime

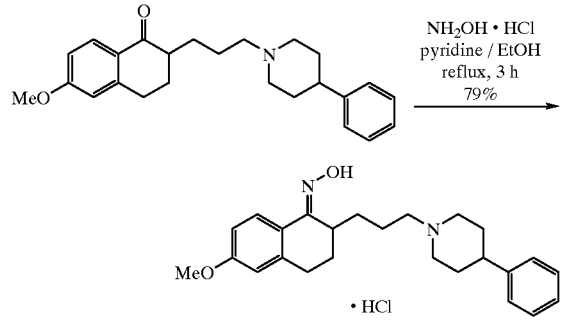

Pyridine (1.3 mL, 17 mmol) was added to a stirring solution of the title compound of Example 202 (0.43 g, 1.0 mmol) and hydroxylamine hydrochloride (1.3 g, 19 mmol) in ethanol (24 mL). After refluxing for 3 hours, the reaction was cooled and the solvent evaporated in vacuo. The residue was transferred to a separatory funnel with EtOAc/sat. NaHCO₃. After extraction with EtOAc (2×120 mL), some solid remained suspended in the EtOAc. The combined EtOAc extracts were heated until everything was in solution and then filtered through a sintered glass funnel containing MgSO₄ rinsing with hot EtOAc (100 mL). The filtrate was evaporated to 150 mL and allowed to sit at ambient temperature overnight. The solid which crystallized was collected to afford 0.31 g (79%) of the title compound as a white solid. mp 209.0–211.5° C.

Anal. for: C$_{25}$H$_{32}$N$_2$O$_2$.0.31 H$_2$O:

Calc'd: C, 70.41; H, 8.26; N, 7.03.

Found: C, 70.40; H, 8.43; N, 7.04.

Using methodology analogous to that described for the title compound of Example 203, the compounds of Examples 204 to 208 were prepared:

Example 204

5,6,7,8-Tetrahydro-5-(hydroxyimino)-N-phenyl-6-[2-(4-phenyl-1-piperidinyl)ethyl]-1-naphthalenecarboxamide

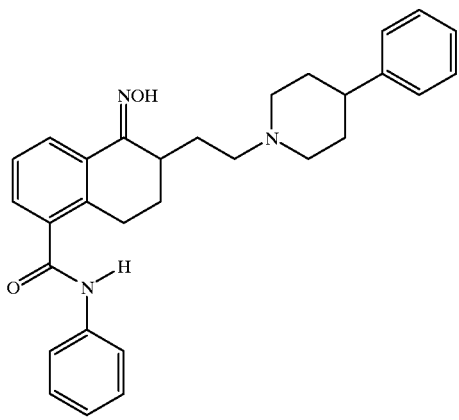

mp (° C.) 222.0–223.0.

Anal. for: $C_{30}H_{33}N_3O_2 \cdot 0.20\ C_4H_8O_2 \cdot 0.70\ H_2O$:

Calc'd: C, 74.30; H, 7.29; N, 8.44.

Found: C, 74.30; H, 6.97; N, 8.35.

Example 205

5,6,7,8-Tetrahydro-5-(hydroxyimino)-6-[2-(4-phenyl-1-piperidinyl)ethyl]-2-naphthalenecarboxylic Acid, Methyl Ester

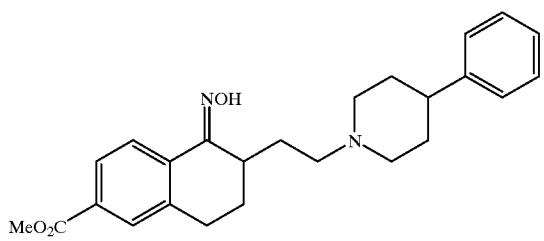

mp (° C.) 189.5–191.

Anal. for: $C_{25}H_{30}N_2O_3 \cdot 0.08\ H_2O$

Calc'd: C, 73.59; H, 7.45; N, 6.87.

Found: C, 73.58; H, 7.26; N, 6.84.

Example 206

5,6,7,8-Tetrahydro-5-(hydroxyimino)-N-phenyl-6-[2-(4-phenyl-1-piperidinyl)ethyl]-2-naphthalenecarboxamide

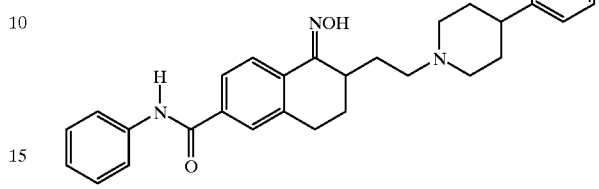

mp (° C.) 224.0–226.5.

Anal. for: $C_{30}H_{33}N_3O_2 \cdot 0.32\ H_2O$:

Calc'd: C, 76.12; H, 7.16; N, 8.88.

Found: C, 76.12; H, 7.01; N, 6.82.

Example 207

N-(3,3-Dimethylbutyl)-5,6,7,8-tetrahydro-5-hydroxyimino)-2-naphthalenecarboxamide

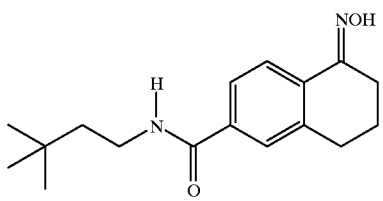

mp (° C.) 183.5–185.5.

Anal. for: $C_{17}H_{24}N_2O_2$:

Calc'd: C, 70.80; H, 8.39; N, 9.71.

Found: C, 70.63; H, 8.54; N, 9.62.

Example 208

N-(3,3-Dimethylbutyl)-5,6,7,8-tetrahydro-5-(hydroxyimino)-6-[2-(4-phenyl)-1-piperidinyl)ethyl]-2-naphthalenecarboxamide

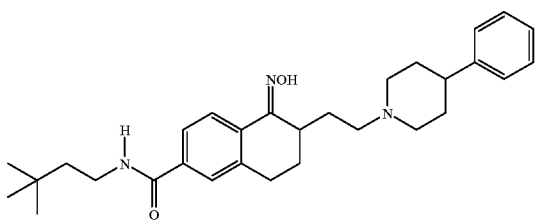

mp (° C.) 218.0–220.0.

Anal. for: $C_{30}H_{41}N_3O_2 \cdot 0.34\ HCl$:

Calc'd: C, 74.80; H, 8.72; N, 8.72.

Found: C, 74.80; H, 8.58; N, 8.65.

Example 209

2-[[[5,6,7,8-Tetrahydro-5-oxo-6-[2-(4-phenyl-1-piperidinyl)ethyl]-2-naphthalenyl]carbonyl]amino]acetic Acid

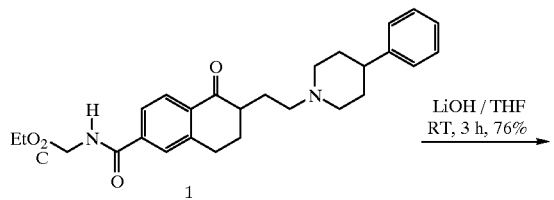

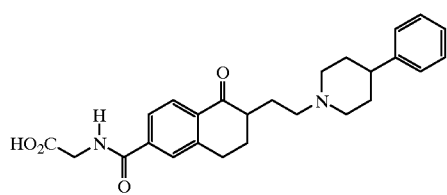

Lithium hydroxide (1 M, 0.45 mL, 0.45 mmol) was added to a solution of ester compound 1 (the title compound of Example 142) (200 mg, 0.39 mmol) in THF (4 mL). After stirring at ambient temperature for 3 hours, the solvent was evaporated in vacuo. Chromatography of the residue (HP-20, 15 mm dia, 0% to 60% acetone/H$_2$O in 10% increments of 50 mL each) afforded 0.14 g (76%) of the title compound after lyophilization. mp (° C.) 152.0–156.0.
Anal. for: C$_{26}$H$_{30}$N$_2$O$_4$.1.20 H$_2$O:
Calc'd: C, 68.46; H, 7.16; N, 6.14.
Found: C, 68.48; H, 7.09; N, 5.94.

Example 210

1,2,3,4-Tetrahydro-6-(hydroxymethyl)-2-[2-(4-phenyl-1-piperidinyl)ethyl]-1-naphthalenol

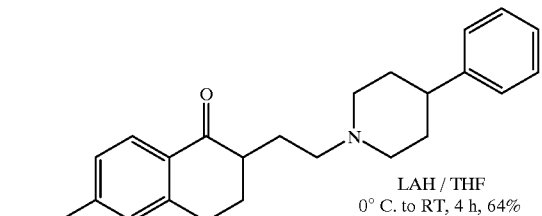

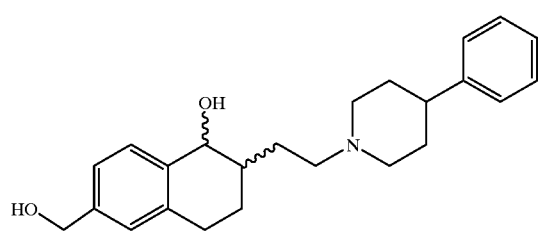

Lithium aluminum hydride (0.16 g, 4.0 mmol) in THF (3.9 mL) was stirred at 0° C. in a flame dried flask under argon. The title C compound of Example 138a (0.50 g, 1.3 mmol) in THF (7.8 mL) was added and the reaction stirred a 0° C. for 2 hours. After stirring at ambient temperature for an additional 2 hours, water (10 drops) was added to the reaction and then Na$_2$SO$_4$.10 H$_2$O (120 mg) was added. Water was added dropwise with vigorous stirring until the precipitate was granular. Anhydrous Na$_2$SO$_4$ was added and the solid filtered rinsing with THF. The filtrate was evaporated, dissolved in CH$_2$Cl$_2$, and dried over MgSO$_4$ to afford 0.56 g of crude product. Flash chromatography (alumina-Activity III, 75% to 90% EtOAc/CH$_2$Cl$_2$ and flushed with 5% MeOH/EtOAc) afforded 0.30 g (64%) of the title compound. mp (° C.) 131.0–134.5.
Anal. for: C$_{24}$H$_{31}$NO$_2$.0.29 H$_2$O:
Calc'd: C, 77.76; H, 8.59; N, 3.78.
Found: C, 77.76; H, 8.43; N, 3.73.

Example 211 cis-5,6,7,8-Tetrahydro-5-hydroxy-N-phenyl-6-[2-(4-phenyl-1-piperidinyl)ethyl]-2-naphthalenecarboxamide, Trifluoroacetate

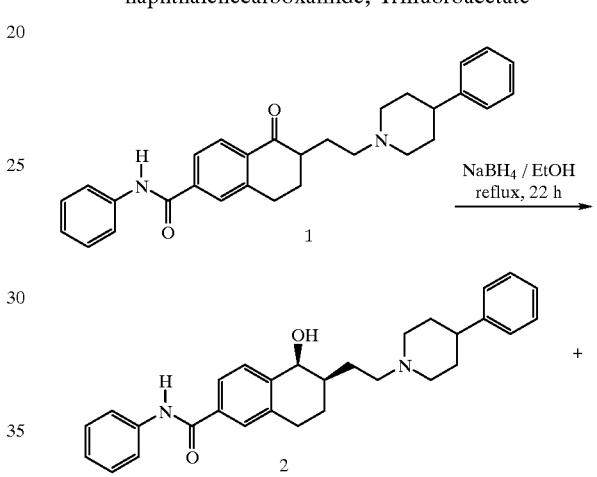

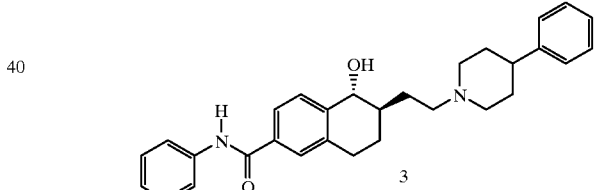

Sodium borohydride (55 mg, 1.5 mmol) was added to a solution of the title compound of Example 138a (0.55 g, 1.2 mmol) in EtOH (18 mL). After refluxing for 22 hours, the reaction was cooled and transferred to a separatory funnel with CH$_2$Cl$_2$/H$_2$O. The pH was adjusted to 8.5. Extraction with CH$_2$Cl$_2$ (2×80 mL) and drying over MgSO$_4$ afforded 0.60 g of crude product after evaporation of the solvent. Preparative HPLC afforded 17 mg (2%) of compound 2 after evaporation in vacuo and lypholization: mp (° C.) 221.0–222.0.
Anal. for: C$_{30}$H$_{34}$N$_2$O$_2$.1.16 C$_2$HF$_3$O$_2$:
Calc'd: C, 66.03; H, 6.05; N, 4.76.
Found: C, 66.03; H, 6.10; N, 4.83.

Further elution afforded 209 mg (28%) of compound 3. mp (° C.) 231.0–233.5.
Anal. for: C$_{30}$H$_{34}$N$_2$O$_2$.1.35 C$_2$HF$_3$O$_2$:
Calc'd: C, 64.51; H, 5.86; N, 4.60.
Found: C, 64.51; H, 5.73; N, 4.61.

Example 212

3,4-Dihydro-6-(phenylacetyl)-2-[2-(4-phenyl-1-piperidinyl)ethyl]-1(2H)-naphthalenone

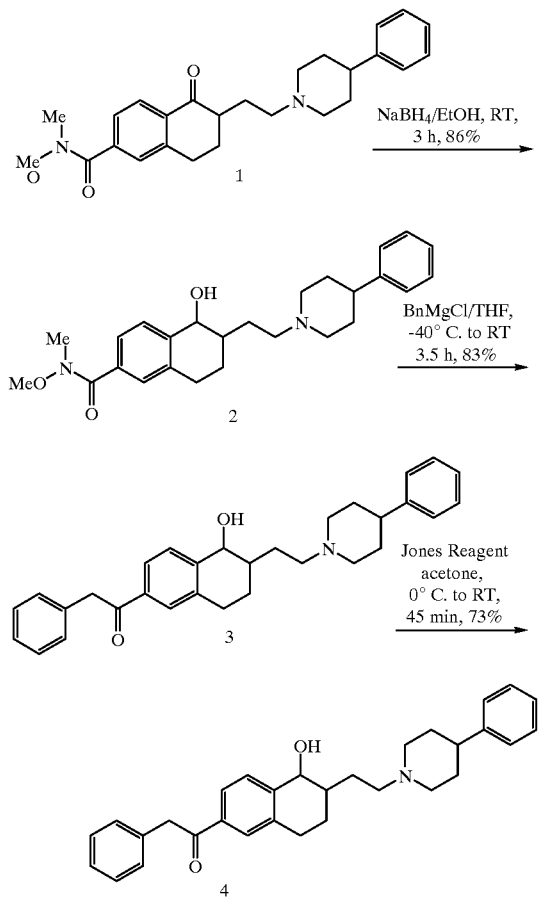

A. 5,6,7,8-Tetrahydro-5-hydroxy-N-methoxy-N-methyl-6-[2-(4-phenyl-1-piperidinyl)ethyl]-2-naphthalenecarboxamide Sodium borohydride (77 mg, 2.1 mmol) was added to a solution of compound of Example 161 (0.88 g, 2.1 mmol) in ethanol (23 mL) stirring at ambient temperature. After stirring at ambient temperature for 3 hours, the reaction was quenched with $H_2O$ and transferred to a separatory funnel with $CH_2Cl_2/H_2O$ and the aqueous layer acidified with 1 N HCl and then basified to pH 8 with saturated $NaHCO_3$. Extraction with $CH_2Cl_2$ (2×40 mL) and drying over $MgSO_4$ afforded 0.99 g of crude product after evaporation of the solvent. Flash chromatography (silica gel, 5% MeOH/ $CH_2Cl_2$) afforded 0.76 g (86%) of the title compound. $R_f$ (silica, 10% MeOH/$CH_2Cl_2$)=0.17.

B. 1-[5,6,7,8-Tetrahydro-5-hydroxy-6-[2-(4-phenyl-1-piperidinyl)ethyl]-2-naphthalenyl]-2-phenylethanone Benzylmagnesium chloride (2 M in THF, 0.68 mL, 1.4 mmol) was added to a solution of the title A compound (0.28 g, 0.66 mmol) in THF (7 mL) stirring at −40° C. The cold bath was removed and the reaction was allowed to stir at ambient temperature. HPLC showed the reaction to be about half complete after 2.5 hours whereupon the reaction was cooled to −40° C. and an additional 0.68 mL (1.4 mmol) of benzylmagnesium chloride was added. After stirring an additional hour at ambient temperature the reaction was quenched with $H_2O$. The reaction was transferred to a separatory funnel with $CH_2Cl_2/H_2O$ and the aqueous layer was acidified to pH 4 with 1 N HCl. Extraction with $CH_2Cl_2$ (2×30 mL) and drying over $MgSO_4$ afforded 0.31 g of crude product. Flash chromatography (silica, 3% MeOH/$CH_2Cl_2$) afforded 0.25 g (83%) of the title compound as an oil.
Anal. for: $C_{31}H_{35}NO_2 \cdot 0.06$ $CH_2Cl_2$:
Calc'd: C, 81.31; H, 7.72; N, 3.05.
Found: C, 81.31; H, 7.39; N, 2.86.

C. 3,4-Dihydro-6-(phenylacetyl)-2-[2-(4-phenyl-1-piperidinyl)ethyl]-1(2H)-naphthalenone Jones reagent (1.25 M, 1.8 mL, 2.2 mmol) was added in 0.45 mL portions over 30 minutes to a solution of the title B compound (0.19 g, 0.41 mmol) in acetone (9 mL) stirring at 0° C. Once addition had been completed, the ice bath was removed and the reaction allowed to stir at ambient temperature. After 45 minutes, the reaction was quenched with isopropanol (2.8 mL) and then evaporated in vacuo. The residue was transferred to a separatory funnel with $CH_2Cl_2$/2 N NaOH. Extraction with $CH_2Cl_2$ (2×60 mL) and drying over $MgSO_4$ afforded 0.14 g of crude product. Flash chromatography (silica, 15 mm dia, 3% MeOH/$CH_2Cl_2$) afforded 0.13 g (73%) of product. Recrystallization from hot EtOH (8 mL) gave pure crystalline title compound.
mp (° C.) 129.0–130.5.
Anal. for: $C_{31}H_{33}NO_2 \cdot 0.32$ $H_2O$:
Calc'd: C, 81.41; H, 7.41; N, 3.06.
Found: C, 81.41; H, 7.14; N, 2.95.

Example 213

5,6,7,8-Tetrahydro-5-oxo-N-(phenylmethyl)-6-[2-(4-phenyl-1-piperidinyl)ethyl]-2-naphthaleneacetamide

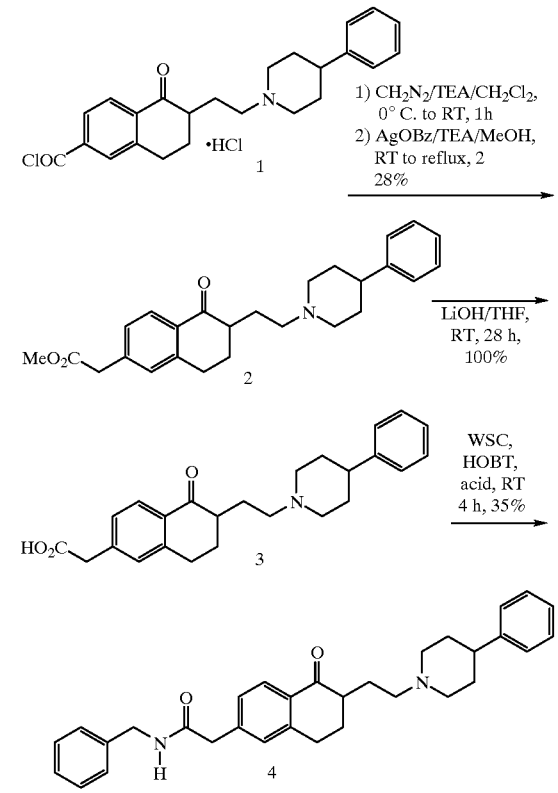

A. 5,6,7,8-Tetrahydro-5-oxo-6-[2-(4-phenyl-1-piperidinyl)ethyl]-2-naphthaleneacetic Acid, Methyl Ester Diazomethane was prepared by adding N-methyl-N-nitrosourea (1.5 g, 15 mmol) to a mixture of 40% KOH (10 mL) and ether (20 mL) stirring at 0° C. in an Erlenmeyer flask. Once the bubbling had ceased, THF (10 mL) was added and the organic layer was transferred dropwise with a fire polished Pasteur pipette to a solution of the title compound of Example 145, part A (0.47 g, 0.92 mmol) and triethylamine (0.13 mL, 0.90 mmol) in CH$_2$Cl$_2$ (10 mL). Additional CH$_2$Cl$_2$ (~10 mL) was added to maintain solubility. After 1 hour stirring at ambient temperature, the reaction was evaporated in vacuo. The residue was dissolved in methanol (20 mL) and AgOBz.TEA (0.1 g in 2.0 mL, 0.28 mL, 0.06 mmol) was added. After stirring at ambient temperature for 1 hour the reaction was refluxed. After 1 hour, the reaction was filtered through Celite to afford 0.68 g of crude product after evaporation of the solvent. Flash chromatography (silica gel, 3% MeOH/CH$_2$Cl$_2$) afforded 0.10 g (28%) of the title compound as an oil.

Anal. for: C$_{26}$H$_{31}$NO$_3$.1.10 H$_2$O:
Calc'd: C, 73.41; H, 7.87; N, 3.29.
Found: C, 73.41; H, 7.58; N, 3.50.

B. 5,6,7,8-Tetrahydro-5-oxo-6-[2-(4-phenyl-1-piperidinyl)ethyl]-2-naphthaleneacetic Acid Lithium hydroxide (1 N in H$_2$O, 0.41 mL, 0.41 mmol) was added to a solution of the title A compound (0.15 g, 0.37 mmol) stirring in THF (3.6 mL). After stirring at ambient temperature for 28 hours, the reaction mixture was evaporated in vacuo. The residue was transferred to a separatory funnel with H$_2$O and the pH adjusted to 7.0 with 1 N NaOH. Extraction with 10% isopropanol/CH$_2$Cl$_2$ (6×50 mL) and drying over MgSO$_4$ afforded 0.14 g (100%) of the title compound after evaporation of the solvent. MS (ESI) 392 (M+H).

C. 5,6,7,8-Tetrahydro-5-oxo-N-(phenylmethyl)-6-[2-(4-phenyl-1-piperidinyl)ethyl]-2-naphthaleneacetamide 1-Hydroxybenzotriazole hydrate (HOBT, 50 mg, 0.37 mmol) and 1-(3-dimethylaminopropyl)-3-ethylcarbodiimide hydrochloride (WSC, 112 mg, 0.37 mmol) were added to a solution of the title B compound (0.14 g, 0.36 mmol) in CH$_2$Cl$_2$ (1.6 mL) and DMF (0.40 mL) stirring at ambient temperature. After stirring for 30 minutes, benzylamine (38 mg, 39 mL, 0.36 mmol) in CH$_2$Cl$_2$ (0.46 mL) was added. After stirring for 4 hours, the reaction was transferred to a separatory funnel with CH$_2$Cl$_2$/H$_2$O and the aqueous layer adjusted to pH 8.0 with saturated NaHCO$_3$. Extraction with CH$_2$Cl$_2$ (2×30 mL) and drying over MgSO$_4$ afforded 0.70 g of crude product after evaporation of the solvent. Flash chromatography (silica gel, 3% MeOH/CH$_2$Cl$_2$) afforded 61 mg (35%) of the title compound.
mp (° C.) 144.0–146.0.
Anal. for: C$_{32}$H$_{36}$N$_2$O$_2$.0.10 CH$_2$Cl$_2$.1.22 H$_2$O:
Calc'd: C, 75.44; H, 7.62; N, 5.48.
Found: C, 75.44; H, 7.24; N, 5.43.

Example 214

N-[[5,6,7,8-Tetrahydro-5-oxo-6-[2-(4-phenyl-1-piperidinyl)ethyl]-2-naphthalenyl]methyl]benzeneacetamide

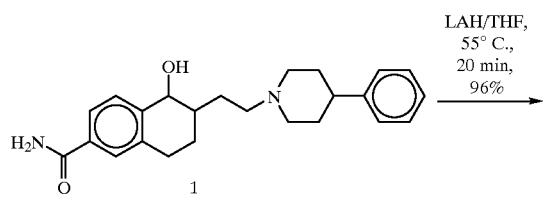

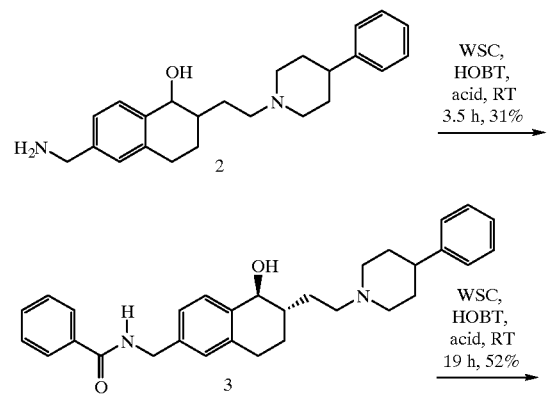

A. 5,6,7,8-Tetrahydro-5-6-[2-(4-phenyl-1-piperidinyl)ethyl]-2-(methylamino)naphthalene Lithium aluminum hydride (50 mg, 1.3 mmol) and THF (0.6 mL) were stirred under agon in a flame dried flask. The title compound of Example 160 (60 mg, 0.16 mmol in THF (0.3 mL) was then added. After stirring at ambient temperature for 20 minutes and at 50° C. for 20 minutes, the reaction was allowed to cool to room temperature and H$_2$O (2 drops) was added. Na$_2$SO$_4$.10 H$_2$O (15 mg) was added and then water was added dropwise to the reaction mixture as it stirred vigorously until the precipitate became granular. Filtration rinsing with THF afforded 56 mg of the title compound.

B. trans-N-[[5,6,7,8-Tetrahydro-5-hydroxy-6-[2-(4-phenyl-1-piperidinyl)ethyl]-2-naphthalenyl]methyl]benzamide 1-Hydroxybenzotriazole hydrate (22 mg, 0.16 mmol) and 1-(3-dimethylaminopropyl)-3-ethylcarbodiimide hydrochloride (WSC, 49 mg, 0.16 mmol) were added to a solution of benzoic acid (18 mg, 0.15 mmol) in CH$_2$Cl$_2$ (0.70 mL) and DMF (0.18 mL) stirring at ambient temperature. After stirring for 30 minutes, the title A compound (56 mg, 0.15 mmol) in CH$_2$Cl$_2$ (0.20 mL) was added. After stirring for 3.5 hours, the reaction was transferred to a separatory funnel with CH$_2$Cl$_2$/H$_2$O and the aqueous layer adjusted to pH 8.0 with saturated NaHCO$_3$. Extraction with CH$_2$Cl$_2$ (2×20 mL) and drying over MgSO$_4$ afforded 80 mg of crude product after evaporation of the solvent. Flash chromatography (silica, 11 mm dia, 4% MeOH/CH$_2$Cl$_2$) afforded 22 mg (31%) of the title compound. mp (° C.) 69.0–72.0.

Example 214a 3,3-Dimethyl-N-[[5,6,7,8-tetrahydro-5-oxo-6-[2-(4-phenyl-1-piperidinyl)ethyl]-2-naphthalenyl]methyl]butanamide and N-[[5,6,7,8-Tetrahydro-5-oxo-6-[2-(4-phenyl-1-piperidinyl)ethyl]-2-naphthalenyl]methyl]benzeneacetamide

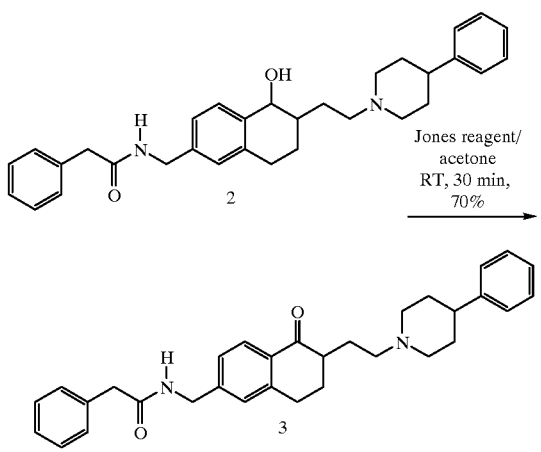

Example 214b 3,3-Dimethyl-N-[[5,6,7,8-tetrahydro-5-oxo-6-[2-(4-phenyl-1-piperidinyl)ethyl]-2-naphthalenyl]butanamide

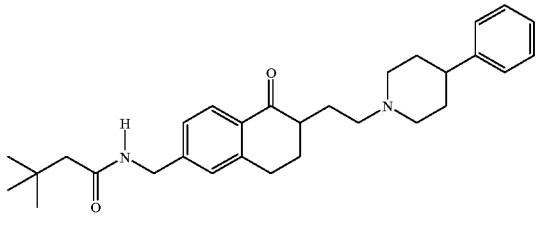

Anal. for: $C_{30}H_{40}N_2O_2 \cdot 0.90\ H_2O$:
Calc'd: C, 75.56; H, 8.84; N, 5.87.
Found: C, 75.56; H, 8.77; N, 5.83.

Example 215

N-(3,3-Dimethylbutyl)-5,6,7,8-tetrahydro-5-oxo-2-naphthalene-carboxamide

A. N-[[5,6,7,8-Tetrahydro-5-hydroxy-6-[2-(4-phenyl-1-piperidinyl)ethyl]-2-naphthalenyl]methyl]benzeneacetamide 1-Hydroxybenzotriazole hydrate (HOBT, 39 mg, 0.29 mmol) and 1-(3-dimethylaminopropyl)-3-ethylcarbodiimide hydrochloride (WSC, 87 mg, 0.29 mmol) were added to a solution of phenylacetic acid (36 mg, 0.28 mmol) in CH$_2$Cl$_2$ (1.3 mL) and DMF (0.32 mL) stirring at ambient temperature. After stirring for 30 minutes, the title A compound of Example 214 (100 mg, 0.27 mmol) in CH$_2$Cl$_2$ (0.36 mL) was added. After stirring for 19 hours, the reaction was transferred to a separatory funnel with CH$_2$Cl$_2$/H$_2$O and the aqueous layer adjusted to pH 8.0 with saturated NaHCO$_3$. Extraction with CH$_2$Cl$_2$ (2×20 mL) and drying over MgSO$_4$ afforded 150 mg of crude product after evaporation of the solvent. Flash chromatography (silica gel, 3% MeOH/CH$_2$Cl$_2$) afforded 68 mg (52%) of the title compound.

B. N-[[5,6,7,8-Tetrahydro-5-oxo-6-[2-(4-phenyl-1-piperidinyl)ethyl]-2-naphthalenyl]methyl]benzeneacetamide Jones reagent (1.25 M, 0.57 mL, 0.71 mmol) was added in 0.14 mL portions over 30 minutes to a solution of the title A compound (65 mg, 0.13 mmol) in acetone (2.8 mL) stirring at 0° C. Once addition had been completed the ice bath was removed and the reaction allowed to stir at ambient temperature. After 30 minutes, the reaction was quenched with isopropanol (0.9 mL) and then evaporated in vacuo. The residue was transferred to a separatory funnel with CH$_2$Cl$_2$/0.1 N NaOH. Extraction with CH$_2$Cl$_2$ (2×25 mL) and drying over MgSO$_4$ afforded 59 mg of crude product. Flash chromatography (silica gel, 11 mm dia, 3% MeOH/CH$_2$Cl$_2$) afforded 44 mg (70%) of the title compound as an oil.

Anal. for: $C_{32}H_{36}N_2O_2 \cdot 0.52\ H_2O$:
Calc'd: C, 78.43; H, 7.62; N, 5.72.
Found: C, 78.43; H, 7.45; N, 5.75.

Using methodology analogous to that described for the title compound of Example 214, the compound of Example 214a was prepared:

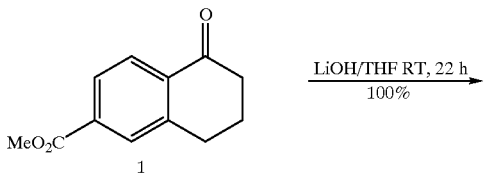

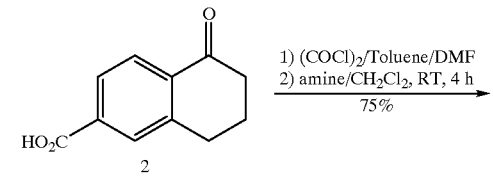

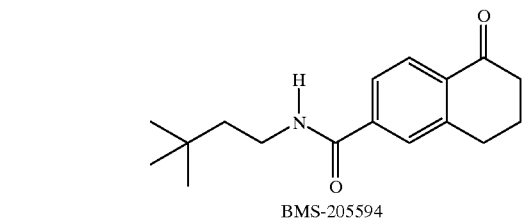

BMS-205594

A. 5,6,7,8-Tetrahydro-5-oxo-2-naphthalenecarboxylic Acid

Lithium hydroxide (1 M in H$_2$O, 5.3 mL, 5.3 mmol) was added to a solution of compound 1 (1.0 g, 4.9 mmol) in THF (48 mL) which had been sparged with argon for 15 minutes. After stirring at ambient temperature under argon for 22 hours, the reaction was evaporated in vacuo. The residue was transferred to a separatory funnel with CH$_2$Cl$_2$/H$_2$O and the aqueous layer was acidified to pH 4 with 1N HCl. Extraction with 10% isopropanol/CH$_2$Cl$_2$ (3×35 mL) and drying over MgSO$_4$ afforded 0.94 g (100%) of the title compound.

B. N-(3,3-Dimethylbutyl)-5,6,7,8-tetrahydro-5-oxo-2-naphthalenecarboxamide

Oxalyl chloride (2M in CH$_2$Cl$_2$, 4.3 mL, 8.6 mmol) was added to a stirring suspension of acid 2 (0.90 g, 4.3 mmol) in toluene (20 mL). DMF (1 drop) was added and the reaction began bubbling. After 2 hours, the reaction was evaporated in vacuo. The residue was dissolved in CH$_2$Cl$_2$ (21 mL) and 3,3-dimethylbutylamine (0.87 g, 1.2 mL, 8.6 mmol) was added. After stirring at ambient temperature for 4 hours, the reaction was transferred to a separatory funnel with $CH_2Cl_2/H_2O$. Extraction with $CH_2Cl_2$ (3×30 mL) and drying over $MgSO_4$ afforded 1.4 g of product after evaporation of the solvent. Flash chromatography (silica gel, 37 mm dia, 40% EtOAc/hexane) afforded 1.2 g of product. Recrystallization from EtOAc/hexane (10 mL/10 mL) afforded 0.89 g (75%) of pure crystalline title compound. mp (° C.) 133.0–134.5.

Anal. for: $C_{17}H_{23}NO_2$:
Calc'd: C, 74.69; H, 8.48; N, 5.12.
Found: C, 74.77; H, 8.42; N, 4.99.

Example 216

N-(3,3-Dimethylbutyl)-5,6,7,8-tetrahydro-5-methoxy-2-naphthalenecarboxamide

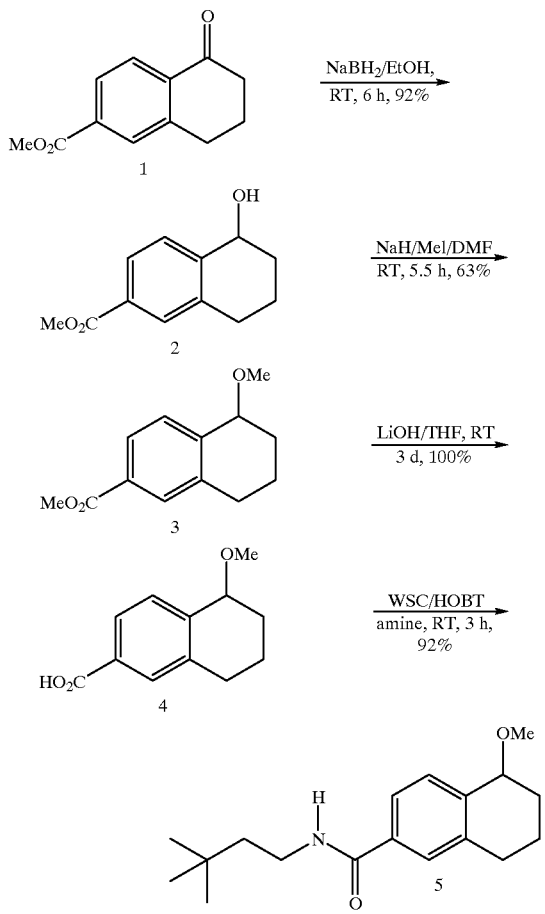

A. 5,6,7,8-Tetrahydro-5-hydroxy-2-naphthalenecarboxylic Acid, Methyl Ester

Sodium borohydride (37 mg, 1.0 mmol) was added to a stirring solution of 1 (For the preparation of 1, see Example 216 0.20 g, 1.0 mmol) in ethanol (11 mL). After stirring at ambient temperature for 5 hours, the reaction was quenched with $H_2O$ and transferred to a separatory funnel with $CH_2Cl_2/H_2O$. The reaction was acidified to pH 4 with 1N HCl and then basified to pH 7.5 with saturated $NaHCO_3$. Extraction with $CH_2Cl_2$ (2×20 mL) and drying over $MgSO_4$ afforded 0.20 g of the title compound. $R_f$ (silica, 25% EtOAc/hexane)=0.15.

B. 5,6,7,8-Tetrahydro-5-methoxy-2-naphthalene-carboxylic Acid, Methyl Ester

Sodium hydride (80% oil dispersion, 28 mg, 0.93 mmol) was added to a solution of 2 (0.19 g, 0.93 mmol) in DMF (2 mL) stirring at 0° C. Methyl iodide (0.13 g, 58 mL, 0.93 mmol) was added. After stirring at 0° C. for 2 hours and at ambient temperature for 30 minutes, additional sodium hydride (14 mg, 0.47 mmol) and methyl iodide (29 mL, 0.47 mmol) were added. After stirring an additional 3 hours, the reaction was quenched with 0.1N HCl and transferred to a separatory funnel with $CH_2Cl_2$. Extraction with $CH_2Cl_2$ (2×40 mL) and drying over $MgSO_4$ afforded 0.33 g of crude product after evaporation of the solvent. Flash chromatography (silica, 25 mm dia, 10% EtOAc/hexane) afforded 0.13 g (63%) of the title compound.

C. 5,6,7,8-Tetrahydro-5-methoxy-2-naphthalene-carboxylic Acid

Lithium hydroxide (1.0 M in $H_2O$, 2.7 mL, 2.7 mmol) was added to a solution of the title B compound (0.55 g, 2.5 mmol) in THF (24 mL). After stirring at ambient temperature for 3 days, the reaction was evaporated in vacuo and the residue transferred to a separatory funnel with $CH_2Cl_2/H_2O$. The first extraction with $CH_2Cl_2$ (40 mL) was discarded and then the aqueous layer was acidified with 1 N HCl. Extraction with $CH_2Cl_2$ (2×50 mL) and drying over $MgSO_4$ afforded 0.52 g (100%) of the title compound.

D. N-(3,3-Dimethylbutyl)-5,6,7,8-tetrahydro-5-methoxy-2-naphthalenecarboxamide 1-hydroxybenzotriazole hydrate (HOBT, 0.17 g, 1.3 mmol) and 1-(3-dimethylaminopropyl)-3-ethylcarbodiimide hydrochloride (WSC, 0.37 g, 1.2 mmol) were added to a solution of the title C compound (0.27 g, 1.1 mmol) in $CH_2Cl_2$ (5.3 mL) and DMF (1.4 mL) stirring at ambient temperature. After stirring for 30 minutes, 3,3-dimethylbutylamine (0.15 g, 0.20 mL, 1.5 mmol) in $CH_2Cl_2$ (0.60 mL) was added. After stirring for 3 hours, the reaction was transferred to a separatory funnel with $CH_2Cl_2/H_2O$ and the aqueous layer adjusted to pH 2.0 with 1 N HCl. Extraction with $CH_2Cl_2$ (2×30 mL), washing the combined organic layers with saturated $NaHCO_3$, and drying over $MgSO_4$ afforded 0.37 g of crude product after evaporation of the solvent. Flash chromatography (silica, 25 mm dia, 30% EtOAc/hexane) afforded 0.30 g (92%) of the title compound. mp (° C.) 72.0–73.0.

Anal. for: $C_{18}H_{27}NO_2$:
Calc'd: C, 74.70; H, 9.40; N, 4.84.
Found: C, 74.46; H, 9.36; N, 4.80.

Using methodology analogous to that described for the title compound of Example 216, the compound of Example 217 was prepared:

Example 217

N-(3,3-Dimethylbutyl)-5-(hexyloxy)-5,6,7,8-tetrahydro-2-naphthalenecarboxamide

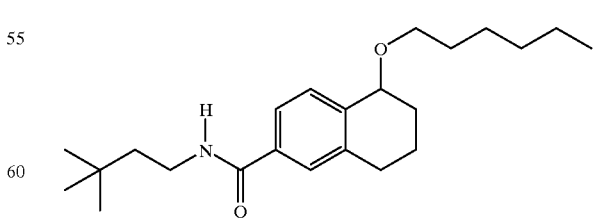

For BMS-206115: $R_f$ (silica, 25% EtOAc/hexane)=0.25.
Anal. for: $C_{23}H_{37}NO_2 \cdot 0.22\ H_2O$:
Calc'd: C, 76.01; H, 10.38; N, 3.85.
Found: C, 76.01; H, 10.24; N, 3.85.

Example 218

N-(3,3-Dimethylbutyl)-5,6,7,8-tetrahydro-6-[2-(4-phenyl-1-piperidinyl)ethyl]-5-oxo-1-naphthalenecarboxamide

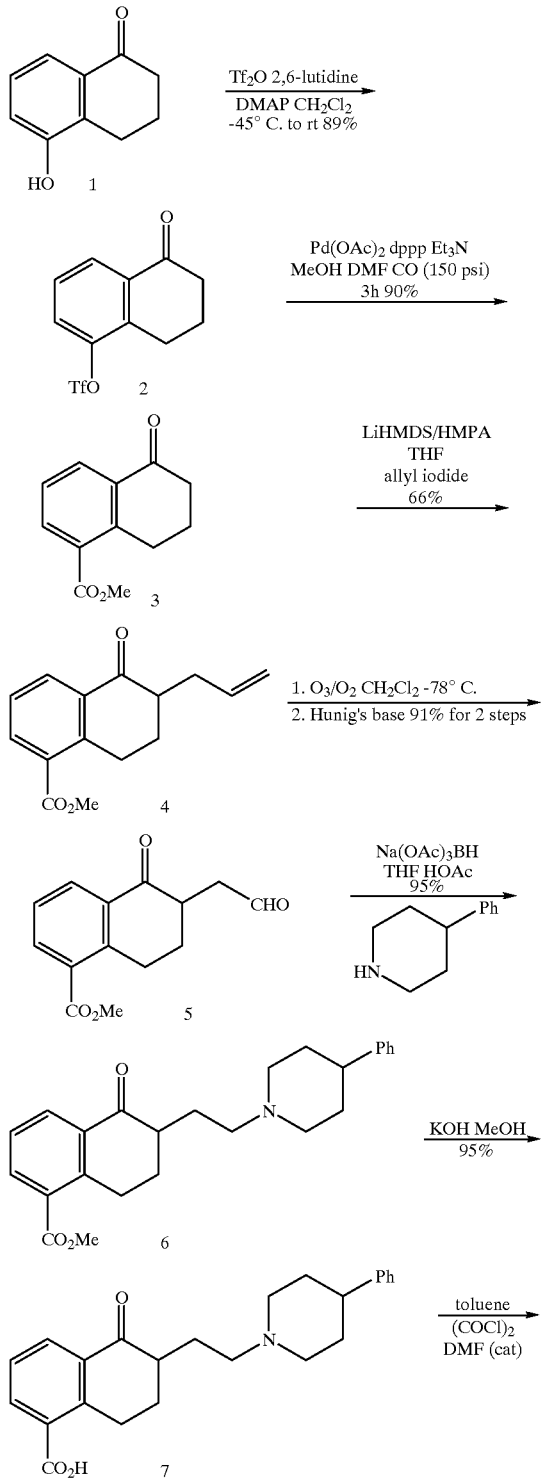

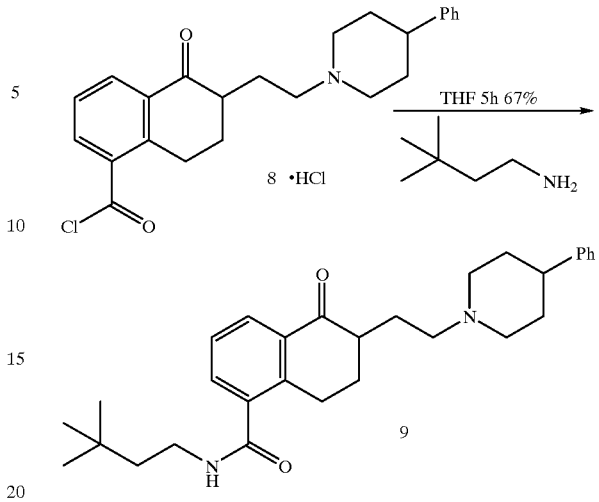

A. Compound 2

To a −45° C. suspension of 5-hydroxy-1-tetralone (30.0 g, 0.185 mol), 4-(dimethylamino)pyridine (4.5 g, 37 mmol) and 2,6-lutidine (25.9 mL, 0.222 mol) in methylene chloride (1.8 L) was added, dropwise, triflic anhydride (37.3 mL, 0.222 mol) over a 30-minute period. The reaction was allowed to come to room temperature and stirred for 1 hour. The reaction was washed with water (500 mL), 1 N HCl (600 mL), water (500 mL), saturated NaHCO$_3$ (400 mL), dried (MgSO$_4$) and concentrated in vacuo to provide 48.4 g (89%) of an oil.

B. Methyl-5-oxo-5,6,7,8-tetrahydronaphthalene-1-carboxylate

A 450-mL Parr bomb was charged with methanol (81 mL), DMF (160 mL), compound 2 (24.0 g, 81.6 mmol), palladium acetate (549 mg, 2.45 mmol), 1,3-bis(diphenylphosphino)-propane (1.01 g, 2.45 mmol), and triethylamine (23 mL, 163 mmol). The bomb was purged with carbon monoxide using 2 fill/vent cycles. The bomb was repressurized to 150 psi and was heated to 80° C. for 3 hours. During this time additional CO was admitted to maintain the pressure at 150 psi. The bomb was cooled to room temperature and vented. A second identical run was made. The combined reactions were diluted with methylene chloride (2 L), washed with water (4×800 mL), dried (MgSO$_4$) and concentrated in vacuo to a black solid. Chromatography (flash, silica, 120 mm dia×20 cm, 2% ethyl acetate/methylene chloride) provided semi-pure product. Recrystallization of this material from hot hexanes in 2 crops followed by chromatography of the final mothor liquors (silica gel, methylene chloride (700 mL) then 2% ethyl acetate/methylene chloride) provided a total of 30.3 g (90%) of the title compound.

C. Methyl 5-oxo-6-(2-propenyl)-5,6,7,8-tetrahydro-naphthalene-1-carboxylate

To a −78° C. suspension of the title B compound (30.3 g, 143 mmol) in dry THF (150 mL) was added, dropwise over a 30-minute period, lithium hexamethyldisilazide (1 M in THF, 134 mL, 134 mmol). The reaction was stirred for 10 minutes and then HMPA (28 mL, 160 mmol) was added, dropwise, over 2 minutes. The reaction was allowed to come to room temperature whereupon allyl iodide (74.6 mL, 444 mmol) was added all at once. The internal temperature rose to 40° C. and then fell to room temperature over a 1 hour period. After an additional 30 minutes, the reaction was diluted with ether (2.5 L), washed with 0.5 N HCl (500 mL), water (500 mL), saturated NaHCO$_3$ (250 mL), saturated sodium chloride (500 mL), dried (MgSO$_4$), and concentrated in vacuo. Flash chromatography (silica gel, 50% methylene chloride/hexanes) in 2 portions followed by rechromatography of impure fractions provided 23.1 g (66%) of the title compound.

D. Compound 5

Using a Welsbach ozonizer, O$_3$/O$_2$ was bubbled into a −78° C. solution of the title C compound (5.26 g, 21.5 mmol) in methylene chloride (200 mL) until a blue color persisted. The reaction was sparged with nitrogen to discharge the excess ozone and diisopropylethylamine (7.5 mL, 43 mmol) was then added dropwise. The reaction was allowed to come to room temperature and stirred for 1.5 hours. The reaction was then washed with 0.3 N HCl (200 mL), water (200 mL), dried (MgSO$_4$) and concentrated in vacuo. Flash chromatography (silica gel, 25% ethyl acetate/hexanes:methylene chloride 9:1) provided 4.81 g (91%) of the desired aldehyde which was used directly in the next reaction.

E. Methyl 5,6,7,8-tetrahydro-6-[2-(4-phenyl-1-piperidinyl)ethyl]-5-oxo-1-naphthalenecarboxylate To a solution of the title D compound (4.81 g, 19.5 mmol) in THF (200 mL) was added, sequentially, 4-phenylpiperidine (4.09 g, 25.4 mmol), acetic acid (1.1 mL, 19.5 mmol), and sodium triacetoxyborohydride (6.62 g, 31.3 mmol). The reaction was stirred for 4 hours and diluted with methylene chloride (1.5 L). The mixture was washed with 0.5 N sodium carbonate (2×200 mL), saturated sodium chloride (200 mL), dried (MgSO$_4$) and concentrated in vacuo. Flash chromatography (silica gel, 50% ethyl acetate/hexanes then ethyl acetate) provided the title compound (7.25 g, 95%).

F. 5,6,7,8-Tetrahydro-6-[2-(4-phenyl-1-piperidinyl)ethyl]-5-oxo-1-naphthalenecarboxylic Acid To a solution of the title E compound (7.00 g, 17.9 mmol) in methanol/methylene chloride (100 mL/10 mL) was added, dropwise, 2 N KOH (25 mL). A transient second phase formed. After 17 hours, an additional 10-mL portion of KOH was added. After 2 hours, the reaction was adjusted to pH 8 with hydrochloric acid and the organics were removed in vacuo. The residue was mixed with water (150 mL) and the pH was readjusted to 8. The solid was collected by filtration, washed with water (3×10 mL) and dried (finally over P$_2$O$_5$) to provide 6.43 g (95%) of a white solid.

G. 5,6,7,8-Tetrahydro-6-[2-(4-phenyl-1-piperidinyl)ethyl]-5-oxo-1-naphthalenecarbonyl Chloride Hydrochloride To a suspension of the title F compound (6.4 g, 17 mmol) in toluene (150 mL) was added 1 drop of DMF and then, dropwise, oxalyl chloride (3.0 mL, 34 mmol). After 6 hours, the reaction was concentrated in vacuo to a yellow solid (7.23 g, 98%).

H. N-(3,3-Dimethylbutyl)-5,6,7,8-tetrahydro-6-[2-(4-phenyl-1-piperidinyl)ethyl]-5-oxo-1-naphthalenecarboxamide To a partial solution of the title G compound (240 mg, 0.555 mmol) in THF (3 mL) was added 3,3-dimethylbutylamine (0.16 mL, 1.2 mmol). After stirring for 5 hours, the reaction was diluted with methylene chloride (20 mL). The mixture was washed with 0.2 N NaOH (10 mL) causing a thick emulsion to form. The mixture was shaken with saturated sodium chloride (3×20 mL) which allowed separation of the organic layer. The organic layer was dried (MgSO$_4$) and concentrated in vacuo. Recrystallization of the product from ethanol/water (ca. 8 mL, ca. 2/1) provided shiny white plates (172 mg, 67%): mp (° C.) 157.5–158.0.

Anal. for: C$_{30}$H$_{40}$N$_2$O$_2$:

Calc'd: C, 78.22; H, 8.75; N, 6.08.

Found: C, 78.20; H, 8.88; N, 5.98.

Using methodology analogous to that described for the title compound of Example 218, the compounds of Examples 219 to 236 were prepared:

Example 219

N-[[3,5 Bis(trifluoromethyl)phenyl]methyl]-5,6,7,8-tetrahydro-6-[2-(4-phenyl-1-piperidinyl)ethyl]-5-oxo-1-naphthalene-carboxamide

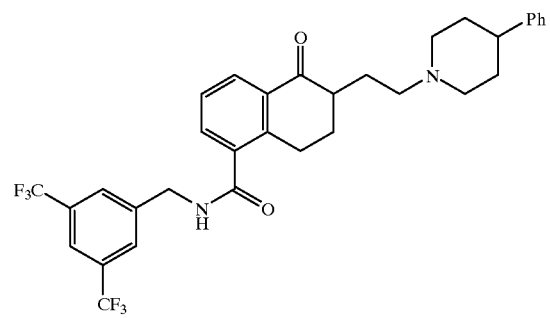

mp (° C.) 171.5–173.0.

Anal. for: C$_{33}$H$_{32}$F$_6$N$_2$O$_2$:

Calc'd: C, 67.55; H, 5.35; N, 4.65; F, 18.92.

Found: C, 65.57; H, 5.15; N, 4.62; F, 18.88.

Example 220

5,6,7,8-Tetrahydro-N-(phenylmethyl)-6-[2-(4-phenyl-1-piperidinyl)ethyl]-5-oxo-1-naphthalenecarboxamide

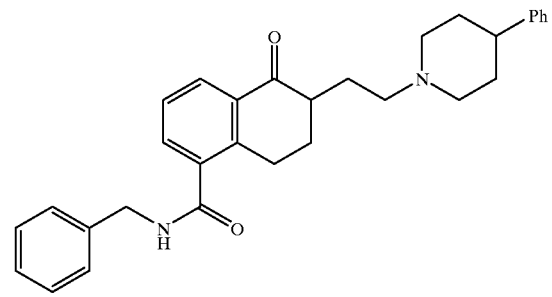

mp (° C.) 175.0–176.0.

Anal. for: C$_{31}$H$_{34}$ClN$_2$O$_2$:

Calc'd: C, 79.80; H, 7.34; N, 6.00.

Found: C, 79.83; H, 7.32; N, 5.95.

Example 221

5,6,7,8-Tetrahydro-5-oxo-N-pentyl-6-[2-(4-phenyl-1-piperidinyl)ethyl]-1-naphthalenecarboxamide

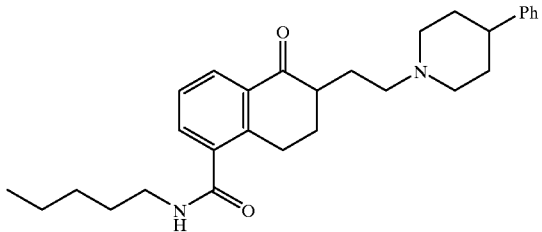

mp (° C.) 129.0–130.0.
Anal. for: $C_{29}H_{38}N_2O_2$:
Calc'd: C, 77.99; H, 8.58; N, 6.27.
Found: C, 78.02; H, 8.61; N, 6.28.

Example 222

N-([1,1-Biphenyl]-2-yl)-5,6,7,8-tetrahydro-5-oxo-6-[2-(4-phenyl-1-piperidinyl)ethyl]-1-naphthalenecarboxamide

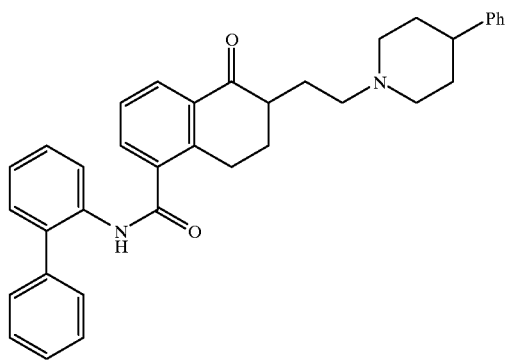

mp (° C.) 144.0–145.0.
Anal. for: $C_{36}H_{36}N_2O_2$:
Calc'd: C, 81.79; H, 6.86; N, 5.30.
Found: C, 81.58; H, 6.74; N, 5.20.

Example 223

1-[[5,6,7,8-Tetrahydro-5-oxo-6-[2-(4-phenyl-1-piperidinyl)ethyl]-1-naphthalenyl]carbonyl]piperidine, (E)-2-butenedioate (1:1)

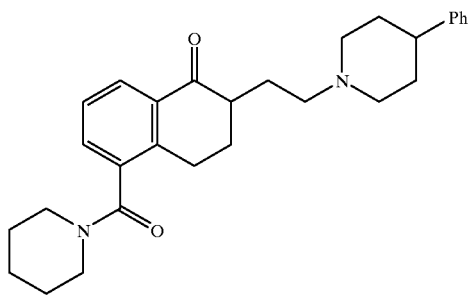

mp (° C.) 118.
Anal. for: $C_{29}H_{36}N_2O_2 \cdot 1.0\ C_4H_4 \cdot 0.83\ H_2O$:
Calc'd: C, 68.75; H, 7.25; N, 4.63.
Found: C, 68.98; H, 7.29; N, 4.68.

Example 224

5,6,7,8-Tetrahydro-5-oxo-N-(2-phenylethyl)-6-[2-(4-phenyl-1-piperidinyl)ethyl]-1-naphthalenecarboxamide

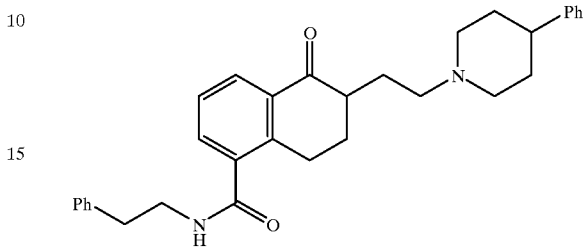

mp (° C.) 143.5–144.5.
Anal. for: $C_{32}H_{36}N_2O_2$:
Calc'd. C, 79.97; H, 7.55; N, 5.83.
Found: C, 79.99; H, 7.41; N, 5.74.

Example 225

5,6,7,8-Tetrahydro-5-oxo-N-[(R)-1-phenylethyl]-6-[2-(4-phenyl-1-piperidinyl)ethyl]-1-naphthalenecarboxamide

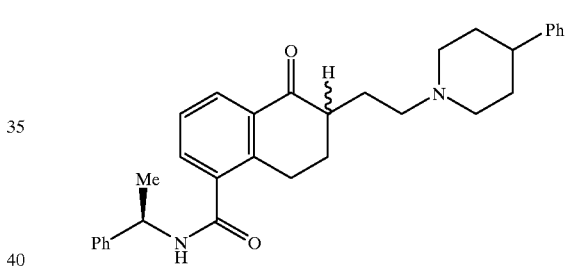

mp (° C.) 169.5–170.0.
Anal. for: $C_{32}H_{36}N_2O_2$:
Calc'd: C, 79.97; H, 7.55; N, 5.83.
Found: C, 79.86; H, 7.48; N, 5.76.

Example 226

5,6,7,8-Tetrahydro-5-oxo-N-[(S)-1-phenylethyl]-6-[2-(4-phenyl-1-piperidinyl)ethyl]-1-naphthalenecarboxamide

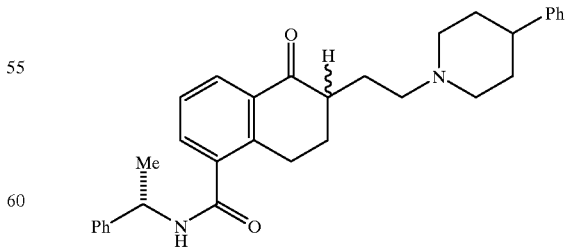

mp (° C.) 169.5–170.5.
Anal. for: $C_{32}H_{36}N_2O_2$:
Calc'd: C, 79.97; H, 7.55; N, 5.83.
Found: C, 79.78; H, 7.52; N, 5.81.

Example 227

N-(3,5-Dimethoxyphenyl)-5,6,7,8-tetrahydro-5-oxo-6-[2-(4-phenyl-1-piperidinyl)ethyl]-1-naphthalenecarboxamide

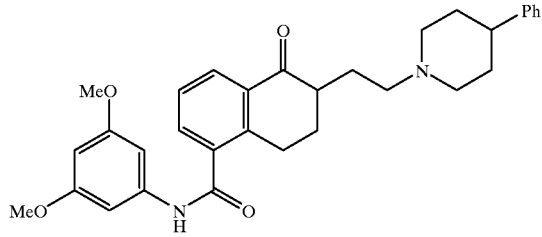

mp (° C.) 141.0–144.5.
Anal. for: $C_{32}H_{36}N_2O_4$:
Calc'd: C, 74.97; H, 7.08; N, 5.46.
Found: C, 74.78; H, 6.90; N, 5.35.

Example 228

N-(2,5-Dimethoxyphenyl)-5,6,7,8-tetrahydro-5-oxo-6-[2-(4-phenyl-1-piperidinyl)ethyl]-1-naphthalenecarboxamide

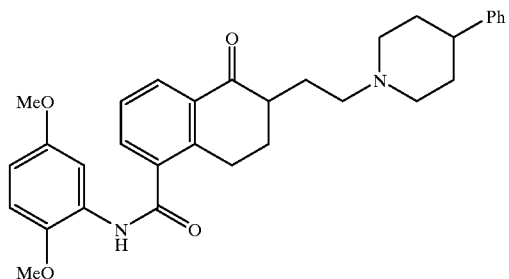

mp (° C.) 117.0–118.5.
Anal. for: $C_{32}H_{36}N_2O_4$:
Calc'd: C, 74.97; H, 7.08; N, 5.46.
Found: C, 75.01; H, 6.98; N, 5.41.

Example 229

N-([1,1'-Biphenyl]-2-ylmethyl)-5,6,7,8-tetrahydro-5-oxo-6-[2-(4-phenyl-1-piperidinyl)ethyl]-1-naphthalenecarboxamide

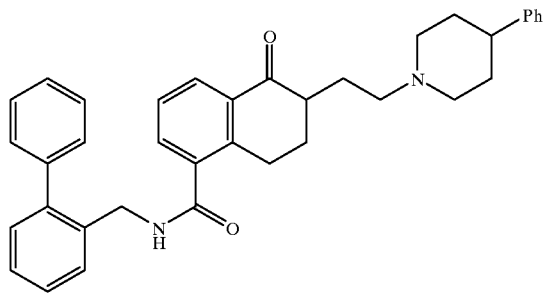

mp (° C.) 157.0–158.5.
Anal. for: $C_{37}H_{38}N_2O_2.0.29 H_2O$:
Calc'd: C, 81.10; H, 7.10; N, 5.11.
Found: C, 81.09; H, 6.82; N, 5.11.

Example 230

N-(3,5-Bis(trifluoromethyl)phenyl]-5,6,7,8-tetrahydro-5-oxo-6-[2-(4-phenyl-1-piperidinyl)ethyl]-1-naphthalenecarboxamide

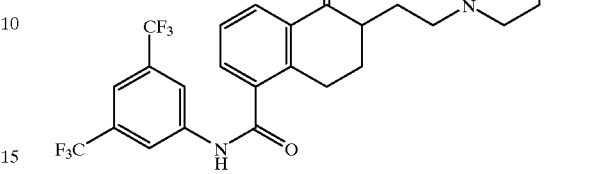

mp (° C.) 178–181.
Anal. for: $C_{32}H_{30}F_6N_2O_2$:
Calc'd: C, 65.30; H, 5.14; F, 4.76; N, 19.37.
Found: C, 65.18; H, 5.07; F, 4.46; N, 19.08.

Example 231

N-([1,1'-Biphenyl]-3-yl))-5,6,7,8-tetrahydro-5-oxo-6-[2-(4-phenyl-1-piperidinyl)ethyl]-1-naphthalenecarboxamide

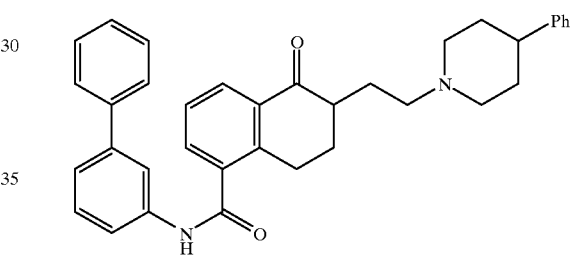

mp (° C.) 222–224.
Anal. for: $C_{36}H_{36}N_2O_2$:
Calc'd: C, 81.79; H, 6.86; N, 5.30.
Found: C, 81.51; H, 6.64; N, 5.15.

Example 232

5,6,7,8-Tetrahydro-N-methyl-5-oxo-N-phenyl-6-[2-(4-phenyl-1-piperidinyl)ethyl]-1-naphthalenecarboxamide

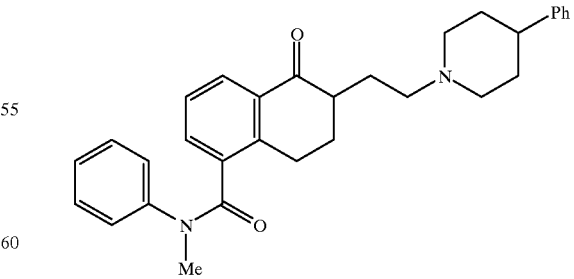

mp (° C.) 139.0–140.0.
Anal. for: $C_{31}H_{34}N_2O_2.0.20 H_2O$:
Calc'd: C, 79.20; H, 7.37; N, 5.96.
Found: C, 79.21; H, 7.27; N, 5.79.

Example 233

5,6,7,8-Tetrahydro-5-oxo-N-(2-phenoxyphenyl)-6-[2-(4-phenyl-1-piperidinyl)ethyl]-1-naphthalenecarboxamide

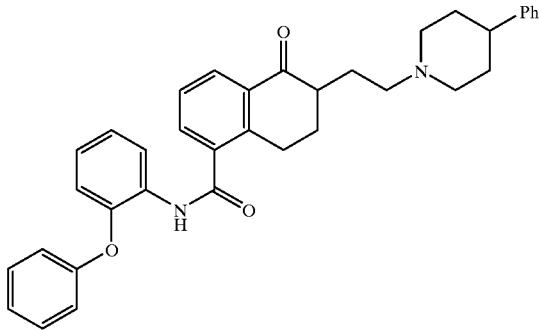

Anal. for: $C_{36}H_{36}N_2O_3$:
Calc'd: C, 79.38; H, 6.66; N, 5.14.
Found: C, 79.41; H, 6.43; N, 5.04.

Example 234

5,6,7,8-Tetrahydro-5-oxo-6-[2-(4-phenyl-1-piperidinyl)ethyl]-N-(3-phenylpropyl)-1-naphthalenecarboxamide

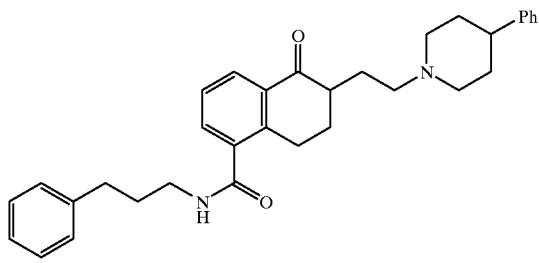

mp (° C.) 158.6–160.0.
Anal. for: $C_{33}H_{38}N_2O_2$:
Calc'd: C, 80.13; H, 7.74; N, 5.66.
Found: C, 80.20; H, 7.81; N, 5.60.

Example 235

N-[(2,2-Dimethylcyclopentyl)methyl]-5,6,7,8-tetrahydro-5-oxo-6-[2-(4-phenyl-1-piperidinyl)ethyl]-1-naphthalenecarboxamide

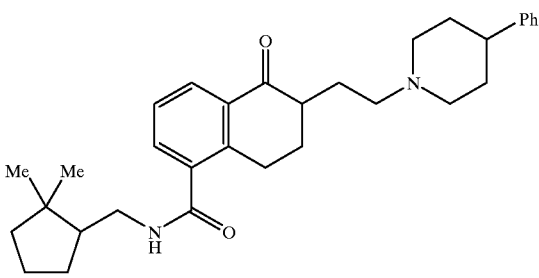

mp (° C.) 110.0–112.0.

Example 236

5,6,7,8-Tetrahydro-N-phenyl-N-(phenylmethyl)-6-[2-(4-phenyl-1-piperidinyl)ethyl]-5-oxo-1-naphthalenecarboxamide

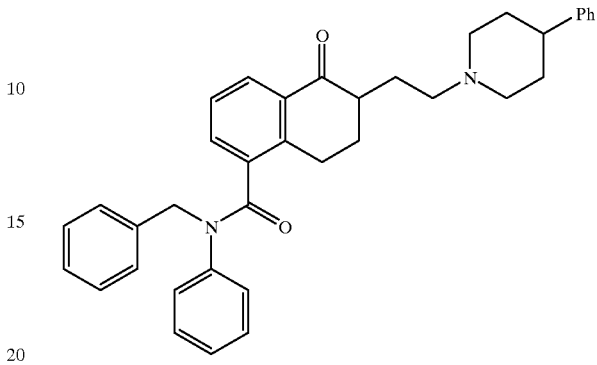

Molecular Weight (Esi): 543.

Example 237

6-Hexyl-5,6,7,8-tetrahydro-5-oxo-N-(2-phenylethyl)-2-naphthalenecarboxamide

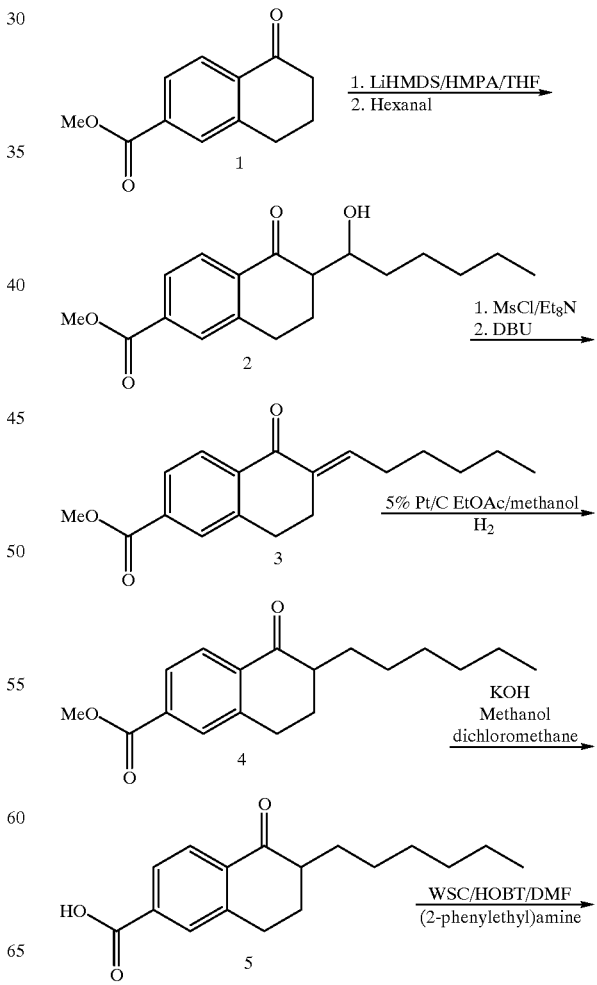

-continued

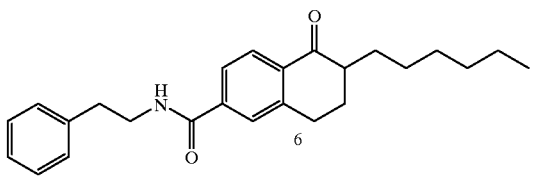

A. Methyl 6-((1-hydroxy)hexyl)-5,6,7,8-tetrahydro-5-2-naphthalenecarboxylate

A slurry of methyl 5,6,7,8-tetrahydro-5-oxo-2-naphthalenecarboxylate (500 mg, 2.45 mmol) in THF was placed in a −78° C. bath and lithium hexamethylsilazide (1.0 M in THF, 2.7 mL) and then HMPA (0.51 mL, 2.9 mmol) were added dropwise. After 20 minutes, hexanal (0.31 mL, 2.6 mmol) was added dropwise. After stirring for 4 hours, the reaction was partitioned between 0.3 N HCl (25 mL) and ether (100 mL). The organic layer was washed with water (25 mL), saturated sodium bicarbonate (25 mL), dried (magnesium sulfate) and concentrated in vacuo. Flash chromatography (silica gel, 25% ethyl acetate/hexanes) provided 635 mg (85%) of a pale yellow oil.

B. Methyl 6-(hexylidine)-5,6,7,8-tetrahydro-5-oxo-2-naphthalenecarboxylate

To a 0° C. solution of the title A compound (613 mg, 2.01 mmol) in dichloromethane (10 mL) was added triethylamine (0.84 mL, 6.0 mmol) and then, dropwise, mesyl chloride (0.34 mL, 4.4 mmol). An additional 0.84 mL portion of triethylamine was added followed by dropwise additionof a 0.34 mL portion of mesylchloride. After 1 h, DBU (0.75 mL, 5.0 mmol) was added dropwise. After an additional 1 h, DBU (0.7 mL) was added. After 30 min., the reaction was diluted with ether (75 mL) washed with 1 N HCl (2×25 mL), water (25 mL), saturated sodium bicarbonate (2×25 mL), dried (magnesium sulfate) and concentrated in vacuo to provide a yellow solid. Flash chromatography (silica gel, 10% ethyl acetate/hexanes) provided a pale yellow solid.

C. Methyl 6-(hexyl)-5,6,7,8-tetrahydro-5-oxo-2-naphthalenecarboxylate

To a solution of the title B compound in methanol/ethyl acetate (6 mL/4 mL) was added 5% Pt/C (30 mg). The reaction was stirred under a hydrogen balloon for 2 hours. The reaction was filtered through Celite and the pad was rinsed with ethyl acetate/methanol 1/1 (3×5 mL). The combined filtrates were concentrated in vacuo. Flash chromatography (silica gel, 10% ethyl acetate/hexanes then 20% ethyl acetate/hexanes) provided a pale yellow oil (424 mg, 73%).

D. 6-(Hexyl)-5,6,7,8-tetrahydro-5-oxo-2-naphthalenecarboxylic Acid

To a solution of the title C compound (402 mg, 1.39 mmol) in methanol (12 mL) and dichloromethane (1 mL) was added 2 N KOH (3 mL). The reaction was stirred for 2 hours and the pH was adjusted to 2. The reaction was concentrated to remove the organic solvents. The residue was diluted with water (20 mL) and the solid was collected by filtration, washed with water (4×10 mL) and dried in vacuo to provide 339 mg (89%) of a white solid.

E. 6-Hexyl-5,6,7,8-tetrahydro-5-oxo-N-(2-phenylethyl)-2-naphthalenecarboxamide

To a solution of the title D compound (100 mg, 0.364 mmol) in DMF (4 mL) were added HOBT (hydrate, 59 mg) triethylamine 0.020 mL, 0.15 mmol) and (2-phenylethyl)amine (0.60 mL, 0.47 mmol). After stirring for 2 hours, the reaction was diluted with ether (25 mL) and was washed with 0.3 N HCl (10 mL), water (10 mL), saturated sodium bicarbonate (10 mL), dried (magnesium sulfate) and concentrated in vacuo. Flash chromatography (silica gel, 25% ethyl acetate/hexanes) provided 134 mg (98%) of a white solid: mp (° C.) 125.0–128.0; MS (ESI) m/z 378.

Using methodology analogous to that described for the title compound of Example 237, the compounds of Examples 238 to 240 were prepared:

Example 238

N-(3,3-Dimethylbutyl)-6-hexyl-5,6,7,8-tetrahydro-5-oxo-2-naphthalenecarboxamide

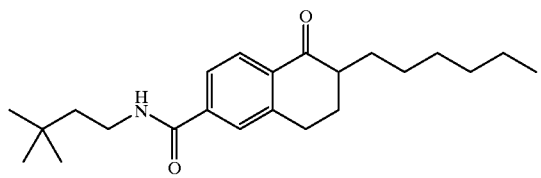

mp (° C.) 78.0–79.5.

MS (ESI) 358.

Example 239

N-[[3,5-Bis(trifluoromethyl)phenyl]methyl]-6-hexyl-5,6,7,8-tetrahydro-5-oxo-2-naphthalenecarboxamide

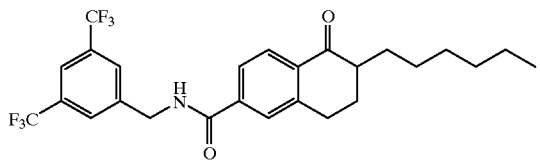

mp (° C.) 108.5–110.0.

MS (ESI) 500.

Example 240

N-[[2,2-Dimethylcyclopentyl)methyl]-6-hexyl-5,6,7,8-tetrahydro-5-oxo-2-naphthalenecarboxamide

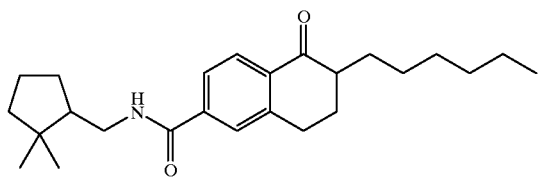

MS (ESI) 384.

Example 241

N-(3,3-Dimethylbutyl)-5,6,7,8-tetrahydro-5-oxo-6-(2-propenyl)-2-naphthalenecarboxamide

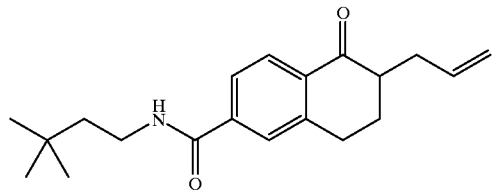

MS (ESI) 314.

Example 242

N-(3,3-Dimethylbutyl)-5,6,7,8-tetrahydro-5-oxo-6-propyl-2-naphthalenecarboxamide

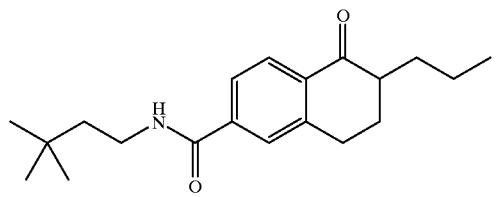

mp (° C.) 111.5–113.5.

MS (ESI) 316.

Example 243

N-[[3,5-Bis(trifluoromethyl)phenyl]methyl]-5,6,7,8-tetrahydro-5-oxo-6-(2-propenyl)-2-naphthalenecarboxamide

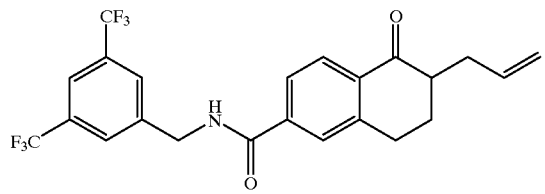

mp (° C.) 113.0–114.0.

MS (ESI) 454.

Example 244

N-[[3,5-Bis(trifluoromethyl)phenyl]methyl]-5,6,7,8-tetrahydro-5-oxo-6-(2-propenyl)-1-naphthalenecarboxamide

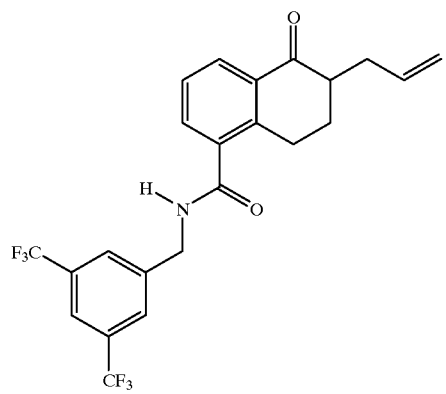

mp (° C.) 158.0–159.0.

MS (ESI) 454.

Anal. for: $C_{23}H_{19}F_6NO_2 \cdot 0.04\ H_2O \cdot 0.05\ C_6H_{14}$:

Calc'd: C, 60.77; H, 4.33; N, 3.04; F, 24.75.

Found: C, 60.77; H, 3.98; N, 3.02; F, 24.43.

Example 245

N-[[3,5-Bis(trifluoromethyl)phenyl]methyl]-5,6,7,8-tetrahydro-5-oxo-6-propyl-1-naphthalenecarboxamide

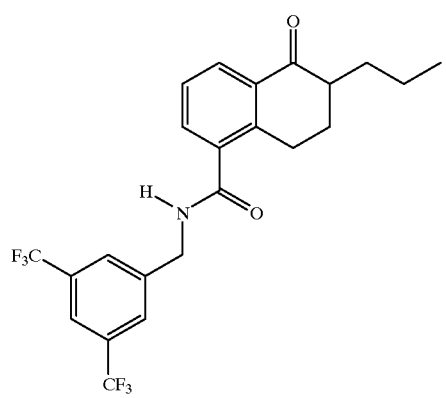

mp (° C.) 171.5–172.5.

MS (ESI) 456.

Anal. for: $C_{23}H_{21}F_6NO_2$:

Calc'd: C, 60.39; H, 4.63; N, 3.06; F, 24.92.

Found: C, 60.50; H, 4.56; N, 3.00; F, 24.73.

Example 246

N-(3,3-Dimethylbutyl)-5,6,7,8-tetrahydro-5-oxo-6-(2-propenyl)-1-naphthalenecarboxamide

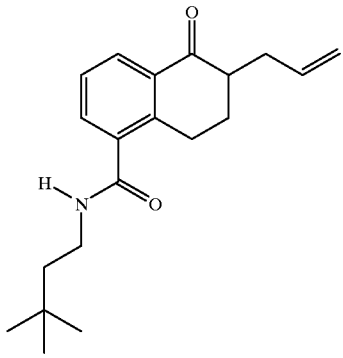

mp (° C.) 100.0–102.0.
Anal. for: $C_{20}H_{27}NO_2$:
Calc'd: C, 76.64; H, 8.68; N, 4.47.
Found: C, 76.59; H, 8.70; N, 4.43.

Example 247

N-(3,3-Dimethylbutyl)-5,6,7,8-tetrahydro-5-hydroxy-2-naphthalenecarboxamide

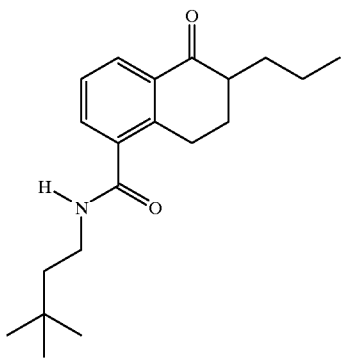

mp (° C.) 127.0–128.0.
Anal. for: $C_{20}H_{29}NO_2$:
Calc'd: C, 76.15; H, 9.27; N, 4.44.
Found: C, 76.12; H, 9.22; N, 4.39.

What is claimed is:

1. A method of treating cardiac arrhythmia which comprises administering to a mammal in need thereof an effective amount of a compound of the formula I

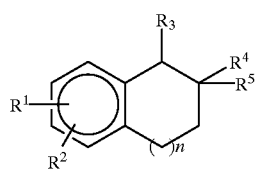

where
  $R^1$ is O-alkyl(aryl), CONH-alkyl, CONH-alkyl(aryl) or CONHalkyl(cycloalkyl)
  $R^2$ is hydrogen;
  $R^3$ is oxo, hydroxy, alkoxy, or NOH;
  $R^4$ is hydrogen or alkyl;
  $R^5$ is alkyl(heterocyclo) or alkyl(substituted amino); and
  n is an integer of 0 to 2
  with the proviso that where $R^3$ is oxo, or hydroxy and $R^1$ is phenylalkyloxy, then $R^5$ is alkyl(heterocyclo).

2. A compound of formula I

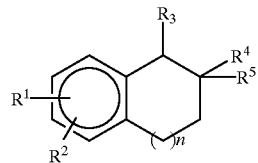

where
  $R^1$ is O-alkyl(aryl), CONH-alkyl, CONH-alkyl;
  $R^2$ is hydrogen;
  $R^3$ is oxo, hydroxy, alkoxy or NOH;
  $R^4$ is hydrogen or alkyl;
  $R^5$ is alkyl(heterocyclo) wherein a hetero atom of the heterocycle is linked to alkyl and alkyl has at least 2 carbons in the chain or $R^5$ is alkyl(substituted amino) where alkyl has at least 2 compounds in the chain; and
  n is an integer of 0 to 2
  with the proviso that
    (1) where $R^3$ is oxo, and $R^1$ is phenylalkyloxy, then $R^5$ is alkyl(heterocyclo), or
    (2) where $R^3$ is hydroxy, $R^1$ is phenylalkyloxy, $R^5$ is alkyl(heterocyclo) other than

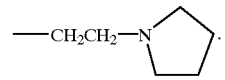

3. A compound as recited in claim 2 wherein
  $R^1$ is O-alkyl(aryl);
  $R^2$ is hydrogen;
  $R^3$ is oxo, hydroxy, alkoxy or NOH;
  $R^4$ is hydrogen or alkyl; and
  n is an integer of 0 to 2.

4. A compound which is:
1,2,3,4-Tetrahydro-6-methoxy-1-oxo-2-[2-(4-phenyl-1-piperidinyl)ethyl]-2-naphthaleneacetic acid, methyl ester, monohydrochloride;
3,4-Dihydro-6-methoxy-2-[2-oxo-2-(4-phenyl-1-piperidinyl)ethyl]-1(2H)-naphthalenone;
1,2,3,4-Tetrahydro-6-methoxy-2-(2-(4-phenyl-1-piperidinenyl)ethyl]-1(2H)-naphthalenol, monohydrochloride;
cis-6-([1,1'-Biphenyl]-2-ylmethoxy)-1,2,3,4-tetrahydro-2-[2-(4-phenyl-1-piperidinyl)ethyl]-1-naphthalenol, [R-(R*, R*)]-2,3-dihydroxybutanedioate (1:1);
trans-1,2,3,4-Tetrahydro-6-(phenylmethoxy)-2-[2-(4-phenyl-1-piperidinyl)ethyl]-1-naphthalenol;
trans-1,2,3,4-Tetrahydro-6-phenyl-2-[2-(4-phenyl-1-piperidinyl)ethyl]-1-naphthalenol;
trans-1,2,3,4-Tetrahydro-6-phenoxy-2-[2-(4-phenyl-1-piperidinyl)ethyl]-1-naphthalenol;
trans-1,2,3,4-Tetrahydro-6-(phenylmethoxy)-2-[2-(1-piperidinyl)ethyl]-1-naphthalenol;
trans-1,2,3,4-Tetrahydro-6-(phenylmethoxy)-2-[2-(4-phenyl-1-piperidinyl)ethyl]-1-naphthalenol, enantiomer A;

trans-1,2,3,4-Tetrahydro-6-(phenylmethoxy)-2-[2-(4-phenyl-1-piperidinyl)ethyl]-1-naphthalenol, enantiomer B;
3,4-Dihydro-6-methoxy-2-[2-(4-phenyl-1-piperidinyl)ethyl]-1(2H)-naphthalenone, monohydrochloride;
3,4-Dihydro-6-phenoxy-2-[2-(4-phenyl-1-piperidinyl)ethyl]-1(2H)-naphthalenone, monohydrochloride;
3,4-Dihydro-6-phenyl-2-[2-(4-phenyl-1-piperidinyl)ethyl]-1(2H)-naphthalenone, monohydrochloride;
3,4-Dihydro-2-[2-(4-phenyl-1-piperidinyl)ethyl]-6-(4-pyridinylmethoxy)-1-(2H)-naphthalenone, dihydrochloride;
3,4-Dihydro-6-(2-phenylethyl)-2-[2-(4-phenyl-1-piperidinyl)ethyl]-1(2H)-naphthalenone;
6-[(1,1,'-Biphenyl]-2-ylmethoxy)-3,4-dihydro-2-[2-(1-piperidinyl)ethyl]-1(2H)-naphthalenone, monohydrochloride;
3,4-Dihydro-6-(2-methylpropoxy)-2-[2-oxo-2-(4-phenyl-1-piperidinyl)ethyl]-1(2H)-naphthalenone;
3,4-Dihydro-2-[2-(4-phenyl-1-piperidinyl)ethyl]-6-(3-pyridinylmethoxy)-1(2H)-naphthalenone, dihydrochloride;
3,4-Dihydro-6-[(3-methylphenyl)methoxy]-2-[2-(4-phenyl-1-piperidinyl)ethyl]-1(2H)-naphthalenone;
6-[(4-Chlorophenyl)methoxy]-3,4-dihydro-2-[2-(4-phenyl-1-piperidinyl)ethyl]-1(2H)-naphthalenone;
3,4-Dihydro-6-[(4-methylphenyl)methoxy]-2-[2-(4-phenyl-1-piperidinyl)ethyl]-1(2H)-naphthalenone;
6-[(2-Chlorophenyl)methoxy]-3,4-dihydro-2-[2-(4-phenyl-1-piperidinyl)ethyl]-1(2H)-naphthalenone;
6-[(3-Chlorophenyl)methoxy]-3,4-dihydro-2-[2-(4-phenyl-1-piperidinyl)ethyl]-1(2H)-naphthalenone;
3,4-Dihydro-6-[[4-(1-methyletyl)phenyl]methoxy]-2-[2-(4-phenyl-1-piperidinyl)ethyl]-1(2H)-naphthalenone;
4-[[5,6,7,8-Tetrahydro-5-oxo-6-[2-(4-phenyl-1-piperidinyl)ethyl]-2-naphthalenyl]oxy]methyl]benzonitrile;
3,4-Dihydro-5-(phenylmethoxy)-2-[2-(4-phenyl-1-piperidinyl)ethyl]-1(2H)-naphthalenone, trifluoroacetate (1:1);
3,4-Dihydro-56-(phenylmethoxy)-2-[2-(4-phenyl-1-piperidinyl)ethyl]-1(2H)-naphthalenone;
3,4-Dihydro-6-(phenylmethoxy)-2-[2-(2-phenyl-1-piperidinyl)ethyl]-1(2H)-naphthalenone, isomer A;
3,4-Dihydro-6-(phenylmethoxy)-2-[2-(2-phenyl-1-piperidinyl)ethyl]-1(2H)-naphthalenone, isomer B;
3,4-Dihydro-6-[(1-phenyl-1H-imidazol-2-yl)methoxy]-2-[2-(4-phenyl-1-piperidinyl)ethyl]-1(2H)-naphthalenone;
3,4-Dihydro-2-[(4-phenyl-1-piperidinyl)ethyl]-6-(2,2,2-trifluoroethoxy)-1(2H)-naphthalenone, monohydrochloride;
3,4-Dihydro-6-[(3-nitrophenyl)methoxy]-2-[2-(4-phenyl-1-piperidinyl)ethyl]-1(2H)-naphthalenone;
3,4-Dihydro-6-[(2-methoxyphenyl)methoxy]-2-[2-(4-phenyl-1-piperidinyl)ethyl]-1(2H)-naphthalenone;
3,4-Dihydro-6-[(2-nitrophenyl)methoxy]-2-[2-(4-phenyl-1-piperidinyl)ethyl]-1(2H)naphthalenone;
6-([1,1'-Biphenyl]-4-ylmethoxy)-3,4-dihydro-2-[2-(4-phenyl-1-piperidinyl)ethyl]-1(2H)-naphthalenone;
6-([1,1'-Biphenyl]-2-ylmethoxy)-3,4-dihydro-2-[2-(4-phenyl-1-piperidinyl)ethyl]-1(2H)-naphthalenone;
3,4-Dihydro-2-[2-(4-phenyl-1-piperidinyl)ethyl]-6-ethoxy-1(2H)-naphthalenone;
3,4-Dihydro-6-[(2-methylphenyl)methoxy]-2-[2-(4-phenyl-1-piperidinyl)ethyl]-1(2H)-naphthalenone;
2-[[5,6,7,8-Tetrahydro-5-oxo-6-[2-(4-phenyl-1-piperidinyl)ethyl]-2-naphthalenyl]oxy]methyl]benzonitrile;
4-[[5,6,7,8-Tetrahydro-5-oxo-6-[2-(4-phenyl-1-piperidinyl)ethyl]-2-naphthalenyl]oxy]methyl]benzoic acid, methyl ester;
3-[[5,6,7,8-Tetrahydro-5-oxo-6-[2-(4-phenyl-1-piperidinyl)ethyl]-2-naphthalenyl]oxy]methyl]benzonitrile;
3,4-Dihydro-6-[(4-nitrophenyl)methoxy]-2-[2-(4-phenyl-1-piperidinyl)ethyl]-1(2H)-naphthalenone;
3,4-Dihydro-6-[(4-methylphenyl)methoxy]-2-[2-(4-phenyl-1-piperidinyl)ethyl]-1(2H)-naphthalenone;
3,4-Dihydro-6-[(3-methoxyphenyl)methoxy]-2-[2-(4-phenyl-1-piperidinyl)ethyl]-1(2H)-naphthalenone;
3,4-Dihydro-2-[2-(4-phenyl-1-piperidinyl)ethyl]-6-propoxy-1(2H)-naphthalenone;
3,4-Dihydro-6-(1-methylethoxy)-2-[2-(4-phenyl-1-piperidinyl)ethyl]-1(2H)-naphthalenone;
3,4-Dihydro-2-[2-(4-phenyl-1-piperidinyl)ethyl]-6-[(2-propenyl)oxy]-1(2H)-naphthalenone;
3,4-Dihydro-6-(1-phenylethoxy)-2-[2-(4-phenyl-1-piperidinyl)ethyl]-1(2H)-naphthalenone, monohydrochloride;
6-(1H-Benzimidazol-2-ylmethoxy)-3,4-dihydro-2-[2-(4-phenyl-1-piperidinyl)ethyl]-1(2H)-naphthalenone, dihydrochloride;
6-([1,1'-Biphenyl]-3-ylmethoxy)-3,4-dihydro-2-[2-(4-phenyl-1-piperidinyl)ethyl]-1(2H)-naphthalenone;
6-(Cyclopropylmethoxy)-3,4-dihydro-2-[2-(4-phenyl-1-piperidinyl)ethyl]-1(2H)-naphthalenone;
6-([1,1'-Biphenyl]-2-ylmethoxy)-3,4-dihydro-2-[2-(1-piperidinyl)ethyl]-1(2H)-naphthalenone, monohydrochloride;
2-[2-(2-Ethyl-1-piperidinyl)ethyl]-3,4-dihydro-6-(phenylmethoxy)-1(2H)-naphthalenone;
3,4-Dihydro-2-[2-[(S)-2-(methoxymethyl)-1-pyrrolidinyl]ethyl]-6-(phenylmethoxy)-1(2H)-naphthalenone, monohydrochloride;
1-[2-[1,2,3,4-Tetrahydro-1-oxo-6-(phenylmethoxy)-2-naphthalenyl]ethyl]-L-proline, phenylmethyl ester;
1-[2-[1,2,3,4-Tetrahydro-1-oxo-6-(phenylmethoxy)-2-naphthalenyl]ethyl]-L-prolinamide;
3,4-Dihydro-6-methoxy-2-[2-(4-phenyl-1-piperidinyl)ethyl]-1(2H)-naphthalenone, oxime, monohydrochloride;
3,4-Dihydro-6-methoxy-2-[2-(4-phenyl-1-piperidinyl)ethyl]-1(2H)-naphthalenone, oxime;
3,4-Dihydro-6-methoxy-2-[2-(4-phenyl-1-piperidinyl)ethyl]-1(2H)-naphthalenone hydrazone;
N-Methyl-2-[3,4-dihydro-6-methoxy-2-[2-(4-phenyl-1-piperidinyl)ethyl]-1(2H)-naphthalenylidene]-hydrazinecarboxamide;
(E)-6-([1,1'-Biphenyl]-2-ylmethoxy)-3,4-dihydro-2-[2-(4-phenyl-1-piperidinyl)ethyl]-1(2H)-naphthalenone, oxime;
(E)-6-([1,1'-Biphenyl]-2-ylmethoxy)-3,4-dihydro-2-[2-(1-piperidinyl)ethyl]-1(2H)-naphthalenone, oxime;
(E)-6-Ethoxy-3,4-dihydro-2-[2-(4-phenyl-1-piperidinyl)ethyl]-1(2H)-naphthalenone, oxime;
5,6,7,8-Tetrahydro-5-oxo-6-[2-(4-phenyl-1-piperidinyl)ethyl]-2-naphthalenecarboxylic acid, methyl ester;
5,6,7,8-Tetrahydro-5-oxo-N-phenyl-6-[2-(4-phenyl-1-piperidinyl)ethyl]-2-naphthalenecarboxamide;
5,6,7,8-Tetrahydro-5-oxo-N-pentyl-6-[2-(4-phenyl-1-piperidinyl)ethyl]-2-naphthalenecarboxamide;
1-[[5,6,7,8-Tetrahydro-5-oxo-6-[2-(4-phenyl-1-piperidinyl)ethyl]-2-naphthalenyl]carbonyl]piperidine;
5,6,7,8-Tetrahydro-N-(1H-imidazol-2-yl)ethyl]-5-oxo-6-[2-(4-phenyl-1-piperidinyl)ethyl]-2-naphthalenecarboxamide, dihydrochloride;
2-[[[5,6,7,8-Tetrahydro-5-oxo-6-[2-(4-phenyl-1-piperidinyl)ethyl]-2-naphthalenyl]carbonyl]amino]acetic acid, ethyl ester;
4-[[[5,6,7,8-Tetrahydro-5-oxo-6-[2-(4-phenyl-1-piperidinyl)ethyl]-2-naphthalenyl]carbonyl]amino]-1-piperidinecarboxylic acid, ethyl ester;
5,6,7,8-Tetrahydro-N-[3-(2-oxo-1-pyrrolidinyl)propyl]-5-oxo-6-[2-(4-phenyl-1-piperidinyl)ethyl]-2-naphthalenecarboxamide;

N-([1,1-Biphenyl]2-yl)-5,6,7,8-tetrahydro-5-oxo-6-[2-(4-phenyl-1-piperidinyl)ethyl]-2-naphthalenecarboxamide, monohydrochloride;

5,6,7,8-Tetrahydro-5-oxo-N-methyl-N-phenyl-6-[2-(4-phenyl-1-piperidinyl)ethyl]-2-naphthalenecarboxamide;

5,6,7,8-Tetrahydro-N-(1-methylethyl)-5-oxo-6-[2-(4-phenyl-1-piperidinyl)ethyl]-2-naphthalenecarboxamide;

5,6,7,8-Tetrahydro-5-oxo-N-(phenylmethyl)-6-[2-(4-phenyl-1-piperidinyl)ethyl]-2-naphthalenecarboxamide;

N-[3,5-Bis(trifluoromethyl)phenyl]-5,6,7,8-tetrahydro-5-oxo-6-[2-(4-phenyl-1-piperidinyl)ethyl]-2-naphthalenecarboxamide, monohydrochloride;

5,6,7,8-Tetrahydro-N-(3,3-dimethylbutyl)-5-oxo-6-[2-(4-phenyl-1-piperidinyl)ethyl]-2-naphthalenecarboxamide, monohydrochloride;

4-[[[5,6,7,8-Tetrahydro-5-oxo-6-[2-(4-phenyl-1-piperidinyl)ethyl]-2-naphthalenyl]carbonyl]amino]benzoic acid, methyl ester;

5,6,7,8-Tetrahydro-N-(2-methoxyphenyl)-5-oxo-6-[2-(4-phenyl-1-piperidinyl)ethyl]-2-naphthalenecarboxamide, monohydrochloride;

5,6,7,8-Tetrahydro-N-(3-pyridinyl)-5-oxo-6-[2-(4-phenyl-1-piperidinyl)ethyl]-2-naphthalenecarboxamide, monohydrochloride;

5,6,7,8-Tetrahydro-N-(3,4-dimethyl-5-isoxazolyl)-5-oxo-6-[2-(4-phenyl-1-piperidinyl)ethyl]-2-naphthalenecarboxamide, monohydrochloride;

5,6,7,8-Tetrahydro-N-[2-(1-methylethyl)phenyl]-5-oxo-6-[2-(4-phenyl-1-piperidinyl)ethyl]-2-naphthalenecarboxamide, (1:1.37) hydrochloride;

N-(3-Chlorophenyl)-5,6,7,8-tetrahydro-5-oxo-6-[2-(4-phenyl-1-piperidinyl)ethyl]-2-naphthalenecarboxamide, (1:2.07) hydrochloride;

5,6,7,8-Tetrahydro-5-oxo-6-[2-(4-phenyl-1-piperidinyl)ethyl]-N-(4-pyridinyl)-2-naphthalenecarboxamide, monohydrochloride;

5,6,7,8-Tetrahydro-5-oxo-6-[2-(4-phenyl-1-piperidinyl)ethyl]-2-naphthalenecarboxylic acid, 1-phenylhydrazide, dihydrochloride;

5,6,7,8-Tetrahydro-5-oxo-6-[2-(4-phenyl-1-piperidinyl)ethyl]-N-(4-pyridinyl)-2-naphthalenecarboxylic acid, 2-phenylhydrazide, hydrochloride;

5,6,7,8-Tetrahydro-5-oxo-6-[2-(4-phenyl-1-piperidinyl)ethyl]-2-naphthalenecarboxamide;

5,6,7,8-Tetrahydro-N-methoxy-N-methyl-5-oxo-6-[2-(4-phenyl-1-piperidinyl)ethyl]-2-naphthalenecarboxamide;

N-([1,1-Biphenyl]-3-yl)-5,6,7,8-tetrahydro-5-oxo-6-[2-(4-phenyl-1-piperidinyl)ethyl]-2-naphthalenecarboxamide;

5,6,7,8-Tetrahydro-5-oxo-6-[2-(4-phenyl-1-piperidinyl)ethyl]-N-(1H-pyrrol-1-yl)-2-naphthalenecarboxamide, monohydrochloride;

5,6,7,8-Tetrahydro-5-oxo-N-(2-phenylethyl)-6-[2-(4-phenyl-1-piperidinyl)ethyl]-2-naphthalenecarboxamide;

5,6,7,8-Tetrahydro-5-oxo-N-(2-phenoxyphenyl)-6-[2-(4-phenyl-1-piperidinyl)ethyl]-2-naphthalenecarboxamide, monohydrochloride;

N-(3,5-Dimethoxyhenyl)-5,6,7,8-tetrahydro-5-oxo-6-[2-(4-phenyl-1-piperidinyl)ethyl]-2-naphthalenecarboxamide, monohydrochloride;

N-(3,5-Bis(trifluoromethyl)phenyl]methyl]-5,6,7,8-tetrahydro-5-oxo-6-[2-(4-phenyl-1-piperidinyl)ethyl]-2-naphthalene-carboxamide, monohydrochloride;

N-(1,1-Biphenyl]-2-ylmethyl)-5,6,7,8-tetrahydro-5-oxo-6-[2-(4-phenyl-1-piperidinyl)ethyl]-2-naphthalenecarboxamide, (1:1.07) hydrochloride;

(3-phenylpropyl)-2-naphthalenecarboxamide 5,6,7,8-Tetrahydro-5-oxo-6-[2-(4-phenyl-1-piperidinyl)ethyl]-N-(4-phenylbutyl)-2-naphthalenecarboxamide;

N-[2-Cyclohexen-1-yl)ethyl]-5,6,7,8-tetrahydro-5-oxo-6-[2-(4-phenyl-1-piperidinyl)ethyl]-2-naphthalenecarboxamide;

N-[2-(3,4-Dimethoxyphenyl)ethyl]-5,6,7,8-tetrahydro-5-oxo-6-[2-(4-phenyl-1-piperidinyl)ethyl]-2-naphthalenecarboxamide;

N-[2,2-Diphenylethyl)-5,6,7,8-tetrahydro-5-oxo-6-[2-(4-phenyl-1-piperidinyl)ethyl]-2-naphthalenecarboxamide;

N-[2,3-Dihydro-1H-inden-2-yl)-5,6,7,8-tetrahydro-5-oxo-6-[2-(4-phenyl-1-piperidinyl)ethyl]-2-naphthalenecarboxamide;

5,6,7,8-Tetrahydro-N-[2-(1-naphthalenyl)ethyl]-5-oxo-6-[2-(4-phenyl-1-piperidinyl)ethyl]-2-naphthalenecarboxamide, hydrochloride;

5,6,7,8-Tetrahydro-N-[2-(2-naphthalenyl)ethyl]-5-oxo-6-[2-(4-phenyl-1-piperidinyl)ethyl]-2-naphthalenecarboxamide;

N-[(2,2-Dimethylcyclopentyl)methyl]-5,6,7,8-tetrahydro-5-oxo-6-[2-(4-phenyl-1-piperidinyl)ethyl]-2-naphthalenecarboxamide;

trans-5,6,7,8-Tetrahydro-5-oxo-N-(2-phenylcyclopropyl)-6-[2-(4-phenyl-1-piperidinyl)ethyl]-2-naphthalenecarboxamide;

5,6,7,8-Tetrahydro-N-(1-naphthalenylmethyl)-5-oxo-6-[2-(4-phenyl-1-piperidinyl)ethyl]-2-naphthalenecarboxamide;

5,6,7,8-Tetrahydro-5-oxo-6-[2-(4-phenyl-1-piperidinyl)ethyl]-N-[(S)-2-phenylcyclopropyl)-2-naphthalenecarboxamide;

5,6,7,8-Tetrahydro-5-oxo-6-[2-(4-phenyl-1-piperidinyl)ethyl]-N-[(R)-2-phenylcyclopropyl)-2-naphthalenecarboxamide;

5,6,7,8-Tetrahydro-N-[(R)-1-(hydroxymethyl)-3-methylbutyl]-5-oxo-6-[2-(4-phenyl-1-piperidinyl)ethyl]-2-naphthalene-carboxamide;

5,6,7,8-Tetrahydro-N-[(S)-1-(hydroxymethyl)-3-methylbutyl]-5-oxo-6-[2-(4-phenyl-1-piperidinyl)ethyl]-2-naphthalene-carboxamide;

5,6,7,8-Tetrahydro-5-oxo-6-[2-(4-phenyl-1-piperidinyl)ethyl]-N-[2-(2-thienyl)ethyl]-2-naphthalenecarboxamide;

N-[(1-(4-Chlorophenyl)cyclopropyl]methyl]-5,6,7,8-tetrahydro-5-oxo-6-[2-(4-phenyl-1-piperidinyl)ethyl]-2-naphthalene-carboxamide;

N-[2-(4-Dibenzofuranyl)ethyl]-5,6,7,8-tetrahydro-5-oxo-6-[2-(4-phenyl-1-piperidinyl)ethyl]-2-naphthalenecarboxamide;

5,6,7,8-Tetrahydro-N-(3-hydroxy-2,3-diphenylpropyl)-5-oxo-6-[2-(4-phenyl-1-piperidinyl)ethyl]-2-naphthalenecarboxamide;

cis-5,6,7,8-Tetrahydro-5-oxo-N-(2-phenylcyclopropyl)-6-[2-(4-phenyl-1-piperidinyl)ethyl]-2-naphthalenecarboxamide;

5,6,7,8-Tetrahydro-5-oxo-N-(2,2,3,3,3-pentafluoropropyl)-6-[2-(4-phenyl-1-piperidinyl)ethyl]-2-naphthalenecarboxamide;

5,6,7,8-Tetrahydro-N-(2-methylbutyl)-5-oxo-6-[2-(4-phenyl-1-piperidinyl)ethyl]-2-naphthalenecarboxamide, trifluoroacetate;

5,6,7,8-Tetrahydro-N-(3-methylbutyl)-5-oxo-6-[2-(4-phenyl-1-piperidinyl)ethyl]-2-naphthalenecarboxamide, trifluoroacetate;

5,6,7,8-Tetrahydro-N-(1-methylbutyl)-5-oxo-6-[2-(4-phenyl-1-piperidinyl)ethyl]-2-naphthalenecarboxamide, trifluoroacetate;

5,6,7,8-Tetrahydro-5-oxo-6-[2-(4-phenyl-1-piperidinyl)ethyl]-N-[(tetrahydro-2-furanyl)methyl]-2-naphthalenecarboxamide, trifluoroacetate;

5,6,7,8-Tetrahydro-5-oxo-6-[2-(4-phenyl-1-piperidinyl)ethyl]-N-(2-phenylpropyl)-2-naphthalenecarboxamide, trifluoroacetate;

5,6,7,8-Tetrahydro-N-(2-hydroxy-2-phenylethyl)-5-oxo-6-[2-(4-phenyl-1-piperidinyl)ethyl]-2-naphthalenecarboxamide, trifluoroacetate;
N-[2-(2-Fluorophenyl)ethyl]-5,6,7,8-tetrahydro-5-oxo-6-[2-(4-phenyl-1-piperidinyl)ethyl]-2-naphthalenecarboxamide, trifluoroacetate;
N-[2-(4-Fluorophenyl)ethyl]-5,6,7,8-tetrahydro-5-oxo-6-[2-(4-phenyl-1-piperidinyl)ethyl]-6-naphthalenecarboxamide, trifluoroacetate;
N-[2-(3-Fluorophenyl)ethyl]-5,6,7,8-tetrahydro-5-oxo-6-[2-(4-phenyl-1-piperidinyl)ethyl]-2-naphthalenecarboxamide, trifluoroacetate;
N-[2-(4-Chlorophenyl)ethyl]-5,6,7,8-tetrahydro-5-oxo-6-[2-(4-phenyl-1-piperidinyl)ethyl]-2-naphthalenecarboxamide;
5,6,7,8-Tetrahydro-N-[2-(1H-indol-3-yl)ethyl]-5-oxo-6-[2-(4-phenyl-1-piperidinyl)ethyl]-2-naphthalenecarboxamide;
N-(3,3-Diphenylpropyl)-5,6,7,8-tetrahydro-5-oxo-6-[2-(4-phenyl-1-piperidinyl)ethyl]-2-naphthalenecarboxamide;
5,6,7,8-Tetrahydro-5-oxo-N-[2-(4-phenoxyphenyl)ethyl]-6-[2-(4-phenyl-1-piperidinyl)ethyl]-2-naphthalenecarboxamide;
3,4-Dihydro-6-methoxy-2-[3-(4-phenyl-1-piperidinyl)propyl]-1(2H)-naphthalenone, monohydrochloride;
(E)-3,4-Dihydro-6-methoxy-2-[(4-phenyl-1-piperidinyl)propyl]-1(2H)-naphthalenone, oxime;
5,6,7,8-Tetrahydro-5-(hydroxyimino)-N-phenyl-6-[2-(4-phenyl-1-piperidinyl)ethyl]-1-naphthalenecarboxamide;
5,6,7,8-Tetrahydro-5-(hydroxyimino)-6-[2-(4-phenyl-1-piperidinyl)ethyl]-2-naphthalenecarboxylic acid, methyl ester;
5,6,7,8-Tetrahydro-5-(hydroxyimino)-N-phenyl-6-[2-(4-phenyl-1-piperidinyl)ethyl]-2-naphthalenecarboxamide;
N-(3,3-Dimethylbutyl)-5,6,7,8-tetrahydro-5-(hydroxyimino)-6-[2-(4-phenyl)-1-piperidinyl)ethyl]-2-naphthalenecarboxamide;
2-[[[5,6,7,8-Tetrahydro-5-oxo-6-[2-(4-phenyl-1-piperidinyl)ethyl]-2-naphthalenyl]carbonyl]amino]acetic acid;
1,2,3,4-Tetrahydro-6-(hydroxymethyl)-2-[2-(4-phenyl-1-piperidinyl)ethyl]-1-naphthalenol
cis-5,6,7,8-Tetrahydro-5-hydroxy-N-phenyl-6-[2-(4-phenyl-1-piperidinyl)ethyl]-2-naphthalenecarboxamide, trifluoroacetate;
3,4-Dihydro-6-(phenylacetyl)-2-[2-(4-phenyl-1-piperidinyl)ethyl]-1(2H)-naphthalenone;
5,6,7,8-Tetrahydro-5-oxo-N-(phenylmethyl)-6-[2-(4-phenyl-1-piperidinyl)ethyl]-2-naphthaleneacetamide;
N-[[5,6,7,8-Tetrahydro-5-oxo-6-[2-(4-phenyl-1-piperidinyl)ethyl]-2-naphthalenyl]methyl]benzeneacetamide
3,3-Dimethyl-N-[[5,6,7,8-tetrahydro-5-oxo-6-[2-(4-phenyl-1-piperidinyl)ethyl]-2-naphthalenyl]methyl]butanamide and;
N-[[5,6,7,8-Tetrahydro-5-oxo-6-[2-(4-phenyl-1-piperidinyl)ethyl]-2-naphthalenyl]methyl]benzeneacetamide;
3,3-Dimethyl-N-[[5,6,7,8-tetrahydro-5-oxo-6-[2-(4-phenyl-1-piperidinyl)ethyl]-2-naphthalenyl]butanamide;
N-(3,3-Dimethylbutyl)-5,6,7,8-tetrahydro-6-[2-(4-phenyl-1-piperidinyl)ethyl]-5-oxo-1-naphthalenecarboxamide;
N-[[3,5 Bis(trifluoromethyl)phenyl]methyl]-5,6,7,8-tetrahydro-6-[2-(4-phenyl-1-piperidinyl)ethyl]-5-oxo-1-naphthalene-carboxamide;
5,6,7,8-Tetrahydro-N-(phenylmethyl)-6-[2-(4-phenyl-1-piperidinyl)ethyl]-5-oxo-1-naphthalenecarboxamide;
5,6,7,8-Tetrahydro-5-oxo-N-pentyl-6-[2-(4-phenyl-1-piperidinyl)ethyl]-1-naphthalenecarboxamide;
N-([1,1'-Biphenyl]-2-yl)-5,6,7,8-tetrahydro-5-oxo-6-[2-(4-phenyl-1-piperidinyl)ethyl]-1-naphthalenecarboxamide;
1-[[5,6,7,8-Tetrahydro-5-oxo-6-[2-(4-phenyl-1-piperidinyl)ethyl]-1-naphthalenyl]carbonyl]piperidine, (E)-2-butenedioate (1:1);
5,6,7,8-Tetrahydro-5-oxo-N-(2-phenylethyl)-6-[2-(4-phenyl-1-piperidinyl)ethyl]-1-naphthalenecarboxamide;
5,6,7,8-Tetrahydro-5-oxo-N-[(R)-1-phenylethyl]-6-[2-(4-phenyl-1-piperidinyl)ethyl]-1-naphthalenecarboxamide;
5,6,7,8-Tetrahydro-5-oxo-N-[(S)-1-phenylethyl]-6-[2-(4-phenyl-1-piperidinyl)ethyl]-1-naphthalenecarboxamide;
N-(3,5-Dimethoxyphenyl)-5,6,7,8-tetrahydro-5-oxo-6-[2-(4-phenyl-1-piperidinyl)ethyl]-1-naphthalenecarboxamide;
N-(2,5-Dimethoxyphenyl)-5,6,7,8-tetrahydro-5-oxo-6-[2-(4-phenyl-1-piperidinyl)ethyl]-1-naphthalenecarboxamide;
N-([1,1'-Biphenyl]-2-ylmethyl)-5,6,7,8-tetrahydro-5-oxo-6-[2-(4-phenyl-1-piperidinyl)ethyl]-1-naphthalenecarboxamide;
N-(3,5-Bis(trifluoromethyl)phenyl)-5,6,7,8-tetrahydro-5-oxo-6-[2-(4-phenyl-1-piperidinyl)ethyl]-1-naphthalenecarboxamide;
N-([1,1'-Biphenyl]-3-yl))-5,6,7,8-tetrahydro-5-oxo-6-[2-(4-phenyl-1-piperidinyl)ethyl]-1-naphthalenecarboxamide;
5,6,7,8-Tetrahydro-N-methyl-5-oxo-N-phenyl-6-[2-(4-phenyl-1-piperidinyl)ethyl]-1-naphthalenecarboxamide;
5,6,7,8-Tetrahydro-5-oxo-N-(2-phenoxyphenyl)-6-[2-(4-phenyl-1-piperidinyl)ethyl]-1-naphthalenecarboxamide;
5,6,7,8-Tetrahydro-5-oxo-6-[2-(4-phenyl-1-piperidinyl)ethyl]-N-(3-phenylpropyl)-1-naphthalenecarboxamide;
N-[(2,2-Dimethylcyclopentyl)methyl]-5,6,7,8-tetrahydro-5-oxo-6-[2-(4-phenyl-1-piperidinyl)ethyl]-1-naphthalenecarboxamide;
5,6,7,8-Tetrahydro-N-phenyl-N-(phenylmethyl)-6-[2-(4-phenyl-1-piperidinyl)ethyl]-5-oxo-1-naphthalenecarboxamide.

5. The compound as defined in claim 2 wherein $R^5$ is heterocycloalkyl wherein heterocyclo is substituted with alkyl, aryl, alkylthio, alkoxy, halo, nitro, keto cyano, hydroxy, azo, oxo, thiazo, amino, substituted amino, carboxylic acid, or carboxylic ester, or alkoxy further substituted with a carboxylic acid or a 5- to 8-membered ring optionally containing 1 to 4 heteroatoms selected from oxygen, nitrogen and sulfur, optionally substituted with alkyl or halogen.

6. The compound as defined in claim 2 wherein $R^5$ is piperidinylalkyl.

7. The compound as defined in claim 2 wherein $R^5$ is 4-phenyl-1-piperidinylalkyl.

8. The compound as defined in claim 2 wherein $R^5$ is 4-phenyl-1-piperidinylethyl.

9. The compound as defined in claim 2 wherein $R^1$ is arylalkyloxy.

10. The compound as defined in claim 2 wherein $R^1$ is 2-phenylphenylmethoxy, $R^5$ is 4-phenyl-1-piperidinylethyl, $R^2$ is H, $R^3$ is oxo and n is 1.

11. The compound as defined in claim 2 having the structure

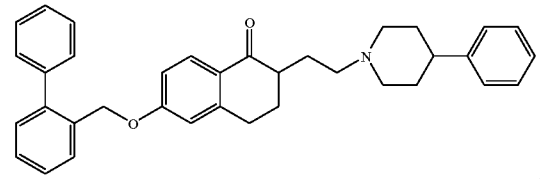

12. The method as defined in claim 1 where in the compound employed $R^5$ is heterocycloalkyl wherein heterocyclo is substituted with alkyl, aryl, alkylthio, alkoxy, halo, nitro, keto, cyano, hydroxy, azo, oxo, thiazo, amino, substituted amino, carboxylic acid, or carboxylic ester, or alkoxy further substituted with a carboxylic acid or a 5- to 8-membered ring optionally containing 1 to 4 heteroatoms selected from oxygen, nitrogen and sulfur, optionally substituted with alkyl or halogen.

13. The method as defined in claim 1 where in the compound employed $R^5$ is piperidinylalkyl.

14. The method as defined in claim 1 where in the compound employed $R^5$ is 4-phenyl-1-piperidinylalkyl.

15. The compound as defined in claim 2 wherein $R^5$ is 4-phenyl-1-piperidinylethyl.

16. The method as defined in claim 1 where in the compound employed $R^1$ is arylalkyloxy.

17. The method as defined in claim 1 where in the compound employed $R^1$ is 2-phenylphenylmethoxy and $R^5$ is 4-phenyl-1-piperidinylethyl, and $R^2$ is H, $R^3$ is oxo and n is 1.

18. The method as defined in claim 1 where the compound employed has the structure

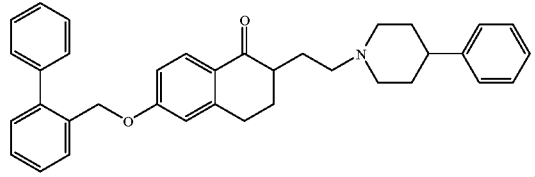

* * * * *